United States Patent
Eida et al.

(10) Patent No.: US 9,425,402 B2
(45) Date of Patent: Aug. 23, 2016

(54) POLYMERIZABLE MONOMER, AND MATERIAL FOR ORGANIC DEVICE, HOLE INJECTION/TRANSPORT MATERIAL, MATERIAL FOR ORGANIC ELECTROLUMINESCENCE ELEMENT AND ORGANIC ELECTROLUMINESCENT ELEMENT EACH COMPRISING POLYMER (POLYMERIC COMPOUND) OF THE POLYMERIZABLE MONOMER

(71) Applicant: IDEMITSU KOSAN CO., LTD., Tokyo (JP)

(72) Inventors: Mitsuru Eida, Sodegaura (JP); Nobuhiro Yabunouchi, Sodegaura (JP); Yumiko Mizuki, Sodegaura (JP); Masami Watanabe, Sodegaura (JP); Akinori Yomogita, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 14/557,946

(22) Filed: Dec. 2, 2014

(65) Prior Publication Data

US 2015/0084031 A1    Mar. 26, 2015

Related U.S. Application Data

(62) Division of application No. 13/138,603, filed as application No. PCT/JP2010/001541 on Mar. 5, 2010, now abandoned.

(30) Foreign Application Priority Data

Mar. 11, 2009  (JP) ................................. 2009-058097

(51) Int. Cl.
| | |
|---|---|
| *H01L 51/50* | (2006.01) |
| *H01L 51/00* | (2006.01) |
| *C07D 207/452* | (2006.01) |
| *C07D 209/86* | (2006.01) |
| *C07D 209/88* | (2006.01) |
| *C07D 307/91* | (2006.01) |
| *C07D 333/76* | (2006.01) |
| *C07D 403/14* | (2006.01) |
| *C07D 405/12* | (2006.01) |
| *C07D 405/14* | (2006.01) |
| *C07D 409/12* | (2006.01) |
| *C08F 12/22* | (2006.01) |
| *C08F 12/26* | (2006.01) |

(Continued)

(52) U.S. Cl.
CPC ......... *H01L 51/0035* (2013.01); *C07C 211/61* (2013.01); *C07C 219/34* (2013.01); *C07C 233/44* (2013.01); *C07D 207/452* (2013.01); *C07D 209/86* (2013.01); *C07D 209/88* (2013.01); *C07D 307/91* (2013.01); *C07D 333/76* (2013.01); *C07D 403/14* (2013.01); *C07D 405/12* (2013.01); *C07D 405/14* (2013.01); *C07D 409/12* (2013.01); *C08F 12/22* (2013.01); *C08F 12/26* (2013.01); *C08F 12/30* (2013.01); *C08F 12/32* (2013.01); *C08F 20/34* (2013.01); *C08F 22/38* (2013.01); *C08F 22/40* (2013.01); *C09B 57/00* (2013.01); *C09B 57/008* (2013.01); *H01L 51/004* (2013.01); *C07C 2102/42* (2013.01); *C07C 2103/18* (2013.01); *H01L 51/0059* (2013.01); *H01L 51/0072* (2013.01); *H01L 51/0073* (2013.01); *H01L 51/5012* (2013.01); *H01L 51/5048* (2013.01); *H01L 51/5056* (2013.01); *H01L 51/5088* (2013.01)

(58) Field of Classification Search
None
See application file for complete search history.

(56) References Cited

U.S. PATENT DOCUMENTS

| | | |
|---|---|---|
| 6,387,545 B1 | 5/2002 | Liu et al. |
| 2001/0017155 A1 | 8/2001 | Bellmann et al. |

(Continued)

FOREIGN PATENT DOCUMENTS

| | | |
|---|---|---|
| JP | 01-105954 A | 4/1989 |
| JP | 07-090255 A | 4/1995 |

(Continued)

OTHER PUBLICATIONS

Tang et al., "Organic electroluminescent diodes," Appl. Phys. Lett., Sep. 21, 1987, 51(12):913-915.

(Continued)

*Primary Examiner* — Gregory Clark
(74) *Attorney, Agent, or Firm* — Foley & Lardner LLP

(57) ABSTRACT

A polymerizable monomer represented by the following formula (1) wherein at least one of $Ar^1$ to $Ar^3$ is substituted by a group represented by the following formula (2) and which is substituted by one or more groups comprising a polymerizable functional group.
$Ar^1$ to $Ar^3$ are a substituted or unsubstituted aryl group having 6 to 40 ring carbon atoms, $Ar^6$ is a substituted or unsubstituted aryl group having 6 to 40 ring carbon atoms and $Ar^4$ and $Ar^5$ are a substituted or unsubstituted arylene group having 6 to 40 ring carbon atoms.

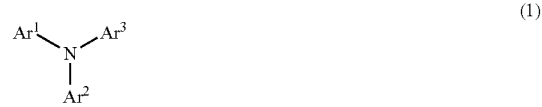

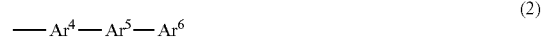

26 Claims, No Drawings

(51) Int. Cl.

| | | |
|---|---|---|
| *C08F 12/30* | (2006.01) | |
| *C08F 12/32* | (2006.01) | |
| *C08F 20/34* | (2006.01) | |
| *C08F 22/38* | (2006.01) | |
| *C08F 22/40* | (2006.01) | |
| *C09B 57/00* | (2006.01) | |
| *C07C 211/61* | (2006.01) | |
| *C07C 219/34* | (2006.01) | |
| *C07C 233/44* | (2006.01) | |

(56) References Cited

U.S. PATENT DOCUMENTS

| | | |
|---|---|---|
| 2003/0111666 A1 | 6/2003 | Nishi et al. |
| 2003/0164678 A1 | 9/2003 | Shirota et al. |
| 2004/0199016 A1 | 10/2004 | Shirota et al. |
| 2006/0049750 A1 | 3/2006 | Shirota et al. |
| 2006/0238110 A1 | 10/2006 | Shirai et al. |
| 2008/0154005 A1 | 6/2008 | Suzuki et al. |

FOREIGN PATENT DOCUMENTS

| | | | |
|---|---|---|---|
| JP | 08-054833 A | 2/1996 | |
| JP | 08-269133 A | 10/1996 | |
| JP | 2001-098023 A | 4/2001 | |
| JP | 2002-110359 A | 4/2002 | |
| JP | 2003-313240 A | 11/2003 | |
| JP | 2004-059743 A | 2/2004 | |
| JP | 2004-303488 A | 10/2004 | |
| JP | 2006-237592 A | 9/2006 | |
| JP | 2008-179790 A | 8/2008 | |
| JP | 2008-198989 A | 8/2008 | |
| JP | 2008-218983 A | 9/2008 | |
| WO | WO 2006/101018 | * 9/2006 | ............. H01L 51/50 |

OTHER PUBLICATIONS

U.S. Office Action dated Jan. 24, 2014 received in U.S. Appl. No. 13/138,603.

U.S. Office Action dated Jun. 16, 2014 received in U.S. Appl. No. 13/138,603.

U.S. Office Action dated Oct. 22, 2013 received in U.S. Appl. No. 13/138,603.

* cited by examiner

POLYMERIZABLE MONOMER, AND MATERIAL FOR ORGANIC DEVICE, HOLE INJECTION/TRANSPORT MATERIAL, MATERIAL FOR ORGANIC ELECTROLUMINESCENCE ELEMENT AND ORGANIC ELECTROLUMINESCENT ELEMENT EACH COMPRISING POLYMER (POLYMERIC COMPOUND) OF THE POLYMERIZABLE MONOMER

CROSS-REFERENCE TO RELATED APPLICATIONS

This application is a Divisional of U.S. application Ser. No. 13/138,603, filed Sep. 9, 2011, which is a U.S. National Stage of International Patent Application PCT/JP2010/001541, filed Mar. 5, 2010 which claims priority to Japanese Patent Application 2009-058097, filed Mar. 11, 2009 the disclosures of which are hereby incorporated by reference in their entirety.

TECHNICAL FIELD

The invention relates to a novel polymerizable monomer having a polymerizable functional group (a functional group which causes a chemical reaction in which two or more molecules of one unit compound are bonded to form a compound of which the molecular weight is an integral multiple of the unit compound), a polymer having it as a repeating unit, a material for an organic device, a hole-injecting/transporting material and an organic electroluminescence device (organic EL device) and an organic EL device each comprising the polymer.

An organic EL device is a self-emission device utilizing the principle that a fluorescent compound emits light by the recombination energy of holes injected from an anode and electrons injected from a cathode when an electric field is impressed. Since C. W. Tang et al. of Eastman Kodak Co. reported a low-voltage driven organic EL device in the form of a stacked type device (Non-Patent Document 1), studies on organic EL devices wherein organic materials are used as the constituent materials have actively been conducted. Tang et al. use tris(8-quinolinolato)aluminum in an emitting layer and a triphenyldiamine derivative in a hole-transporting layer. The advantages of the stack structure are to increase injection efficiency of holes to the emitting layer, to increase generation efficiency of excitons generated by recombination by blocking electrons injected from the cathode, to confine the generated excitons in the emitting layer, and so on. Like this example, as the structure of the organic EL device, a two-layered type of a hole-transporting (injecting) layer and an electron-transporting emitting layer, and a three-layered type of a hole-transporting (injecting) layer, an emitting layer and an electron-transporting (injecting) layer are widely known. In such stack structure devices, their device structures and fabrication methods have been contrived to increase recombination efficiency of injected holes and electrons.

In recent years, practical application of a display or an illumination device using such organic EL device has been actively studied. A reduction in cost and an increase in screen size can be mentioned as important subjects for realizing such practical application. Under such circumstances, as compared with conventional vacuum deposition type organic EL devices, there is an increasing demand for a coating (solution) type organic EL device. A coating type organic EL device is expected to have such advantages that untilization efficiency of raw materials is high, film formation for attaining a large screen is facilitated, and costs incurred for apparatuses are decreased since no vacuum system is required.

As organic EL materials for a coating type organic device, low-molecular materials and high-molecular materials can be mentioned. In order to attain solubility, uniform coating and to obtain a device with a stacked structure, high-molecular materials are preferable. In particular, development of a material for a high-molecular hole-transporting (injecting) layer which can function as the common layer of a display or an illumination device has been desired.

As the material for the high-molecular hole-transporting (injecting) layer, a polymer having a repeating unit obtained by substituting a low-molecular hole-transporting material with a vinyl group is known (Documents 1 to 11)

However, in an organic EL device having the above-mentioned polymer in a hole-transporting (injecting) layer, device performance such as life (half life) and luminous efficiency is not necessarily sufficient. In particular, there is a problem that, if such organic EL devices are subjected to high-luminance or high-temperature driving, which is practical in applications such as a display and an illuminator, the life thereof is significantly shortened.

RELATED ART DOCUMENTS

Patent Documents

Patent Document 1: JP-A-H01-105954
Patent Document 2: JP-A-H07-90255
Patent Document 3: JP-A-H08-54833
Patent Document 4: JP-A-H08-269133
Patent Document 5 JP-A-2001-098023
Patent Document 6: JP-A-2002-110359
Patent Document 7: JP-A-2003-313240
Patent Document 8: JP-A-2004-059743
Patent Document 9: JP-A-2006-237592
Patent Document 10: JP-A-2008-198989
Patent Document 11: JP-A-2008-218983

Non-Patent Document

Non-Patent Document 1: C. W. Tang, S. A. Vanslyke, Applied Physics Letters, Vol. 51, Page 913, 1987

SUMMARY OF THE INVENTION

An object of the invention is to provide a novel polymerizable monomer and a polymer having it as a repeating unit which is useful as a material for a coating type organic device, in particular as a hole-injecting/transporting material, as well as to provide an organic EL device which is improved in device performance such as life and luminous efficiency and hence is suited for practical application.

That is, the invention provides the following polymerizable monomer, a polymer having it as a repeating unit, a material for an organic device, a hole-injecting/transporting material, a material for an organic electroluminescence device (organic EL device) and an organic EL device each comprising the polymer.

1. A polymerizable monomer represented by the following formula (1) wherein at least one of $Ar^1$ to $Ar^3$ is a group represented by the following formula (2) and which is substituted by one or more groups comprising a polymerizable functional group:

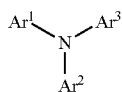   (1)

wherein $Ar^1$ to $Ar^3$ are independently a substituted or unsubstituted aryl group having 6 to 40 carbon atoms that form a ring (hereinafter referred to as "ring carbon atoms"),

   (2)

wherein $Ar^6$ is a substituted or unsubstituted aryl group having 6 to 40 ring carbon atoms and $Ar^4$ and $Ar^5$ are independently a substituted or unsubstituted arylene group having 6 to 40 ring carbon atoms, the substituents of $Ar^1$ to $Ar^6$ when they are substituted are independently one or more groups selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 atoms that form a ring (hereinafter referred to as "ring atoms"), a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 ring carbon atoms, an alkylarylamino group having 8 to 30 carbon atoms wherein the aryl part has 6 to 20 ring carbon atoms, a halogen atom, a nitro group, a cyano group and a hydroxyl group.

2. A polymerizable monomer represented by the formula (1) wherein at least one of $Ar^1$ to $Ar^3$ is a group represented by the following formula (3) and which is substituted by one or more groups comprising a polymerizable functional group:

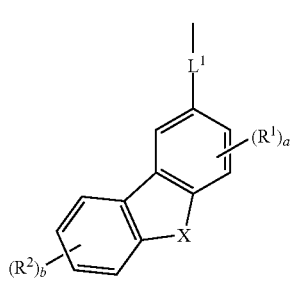   (3)

wherein $L^1$ is a single bond or a substituted or unsubstituted arylene group having 6 to 50 ring carbon atoms;

the substituents of $L^1$ when it is substituted are one or more groups selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring atoms, a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 ring carbon atoms, an alkylarylamino group having 8 to 30 carbon atoms wherein the aryl part has 6 to 20 ring carbon atoms, a halogen atom, a nitro group, a cyano group and a hydroxyl group;

X is a substituted or unsubstituted hetero atom;

the substituents of X when it is substituted are one or more groups selected from the group consisting of a hydrogen atom, an alkyl group having 1 to 20 carbon atoms, a cycloalkyl group having 3 to 10 carbon atoms, an aryl group having 6 to 30 ring carbon atoms, an aralkyl group having 7 to 31 carbon atoms wherein the aryl part has 6 to 30 ring carbon atoms and a heterocyclic group having 3 to 30 ring atoms;

$R^1$ and $R^2$ are independently a group selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring atoms, a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 ring carbon atoms, an alkylarylamino group having 8 to 30 carbon atoms wherein the aryl part has 6 to 20 ring carbon atoms, a halogen atom, a nitro group, a cyano group and a hydroxyl group;

a is an integer of 0 to 3; and b is an integer of 0 to 4.

3. The polymerizable monomer according to 2 wherein the group represented by the formula (3) is a group selected from the group consisting of groups represented by the following formulas (4) to (6):

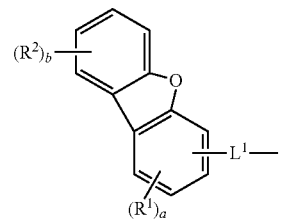   (4)

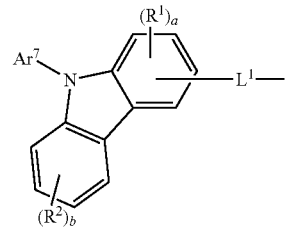   (5)

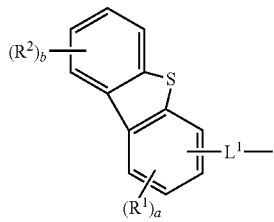

wherein $L^1$, $R^1$, $R^2$, a and b are as defined in claim 2; and $Ar^7$ is a group selected from the group consisting of a hydrogen atom, an alkyl group having 1 to 20 carbon atoms, a cycloalkyl group having 3 to 10 carbon atoms, an aryl group having 6 to 30 ring carbon atoms, an aralkyl group having 7 to 31 carbon atoms wherein the aryl part has 6 to 30 ring carbon atoms and a heterocyclic group having 3 to 30 ring atoms.

4. A polymerizable monomer represented by the formula (1) wherein at least one of $Ar^1$ to $Ar^3$ is a group represented by the following formula (7) and which is further substituted by one or more groups comprising a polymerizable functional group:

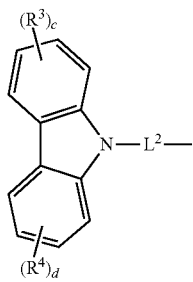

wherein $R^3$ and $R^4$ are independently a group selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring atoms, a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 ring carbon atoms, an alkylarylamino group having 8 to 30 carbon atoms wherein the aryl part has 6 to 20 ring carbon atoms, a halogen atom, a nitro group, a cyano group and a hydroxyl group;

c and d are independently an integer of 0 to 4;

$L^2$ is a substituted or unsubstituted arylene group having 10 to 50 ring carbon atoms; and the substituents of $L^2$ when it is substituted are one or more groups selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring atoms, a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 ring carbon atoms, an alkylarylamino group having 8 to 30 carbon atoms wherein the aryl part has 6 to 20 ring carbon atoms, a halogen atom, a nitro group, a cyano group and a hydroxyl group.

5. The polymerizable monomer according to 1 wherein, in the formula (1), at least one of the groups of $Ar^1$ to $Ar^3$ is a group represented by the formula (2) and at least one of the remaining groups of $Ar^1$ to $Ar^3$ is a group represented by the formula (3).

6. The polymerizable monomer according to 5, wherein the group represented by the formula (3) is a group selected from the groups represented by the formulas (4) to (6).

7. The polymerizable monomer according to 1, wherein, in the formula (1), at least one of the groups of $Ar^1$ to $Ar^3$ is a group represented by the formula (2) and at least one of the remaining groups of $Ar^1$ to $Ar^3$ is a group represented by the formula (7).

8. The polymerizable monomer according to 2, wherein, in the formula (1), at least one of the groups of $Ar^1$ to $Ar^3$ is a group represented by the formula (3) and at least one of the remaining groups of $Ar^1$ to $Ar^3$ is a group represented by the formula (7).

9. The polymerizable monomer according to 8, wherein the group represented by the formula (3) is a group selected from the group consisting of the groups represented by the formulas (4) to (6).

10. The polymerizable monomer according to one of 2, 3 and 5 to 9, wherein $L^1$ is selected from the group consisting of a phenylene group, a naphthylene group, a biphenylene group, a terphenylene group and a fluorenylene group.

11. The polymerizable monomer according to one of 4 and 7 to 9, wherein $L^2$ is selected from the group consisting of a naphthylene group, a biphenylene group, a terphenylene group and a fluorenylene group.

12. The polymerizable monomer according to one of 1 to 11, wherein the number of the at least one group comprising a polymerizable functional group is one.

13. The polymerizable monomer according to one of 1 to 12 wherein the group comprising a polymerizable functional group is substituted by at least one aryl group selected from the group consisting of $Ar^1$ to $Ar^3$ in the formula (1), $Ar^6$ in the formula (2) and $Ar^7$ in the formula (5).

14. The polymerizable monomer according to 13, wherein an aromatic group at the terminal is substituted by the group comprising a polymerizable functional group and the polymerizable functional group and the part other than the terminal aromatic group are bonded to the terminal aromatic group at the para position.

15. The polymerizable monomer according to one of 1 to 14, wherein the group comprising a polymerizable functional group is a group selected from the groups of the following formulas (i) to (v):

(i) a group comprising a vinyl group or a vinylidene group shown below:

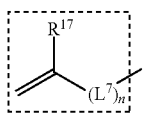

wherein $R^{17}$ is a hydrogen atom, an alkyl group having 1 to 50 carbon atoms or a substituted or unsubstituted aryl group having 6 to 40 ring carbon atoms; $L^7$ is a divalent linking group; and n is an integer of 0 or 1:
(ii) a group comprising a N-maleimide group shown below:

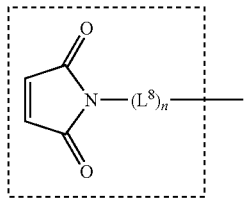

wherein $L^8$ is a divalent linking group and n is an integer of 0 or 1:
(iii) a group comprising a norbornenyl group shown below:

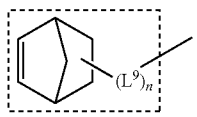

wherein $L^9$ is a divalent linking group and n is an integer of 0 or 1:
(iv) a group comprising an acetylenyl group shown below:

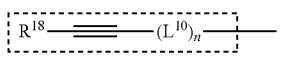

wherein $R^{18}$ is a hydrogen atom, an alkyl group having 1 to 50 carbon atoms or a substituted or unsubstituted aryl group having 6 to 40 ring carbon atoms; $L^{10}$ is a divalent linking group; and n is an integer of 0 or 1: and
(v) a group comprising a cyclopolymerizable or ring-opening polymerizable functional group selected from the group consisting of a group having a substituted or unsubstituted norbornene skeleton other than the group (iii), a group having a substituted or unsubstituted epoxy group or a substituted or unsubstituted oxetane group; a functional group having a lactone structure or a lactum structure; a cyclooctatetraene group or a 1,5-cyclooctadiene group; and 1,ω-diene group, an o-divinylbenzene group and a 1,ω-diyne group.
16. The polymerizable monomer according to 15, wherein $L^7$ to $L^{10}$ comprise one linking group or a linking group formed by bonding, in an arbitral order, of two or more linking groups, the linking group being selected from the following divalent linking groups:
-$L^{11}$-, —O—, —C(=O)—, —C(=O)O—, —OC(=O)—, —C(=O)NR$^{19}$—, —NR$^{20}$C(=O)—, —NR$^{21}$—, —S—, —C(=S)— wherein $L^{11}$ is one group or a group formed by bonding, in an arbitral order, of two or more groups, the group being selected from the group consisting of a substituted or unsubstituted arylene group having 6 to 40 ring carbon atoms, a substituted or unsubstituted divalent heterocyclic group having 3 to 40 ring atoms, a substituted or unsubstituted alkylene group having 1 to 50 carbon atoms, a substituted or unsubstituted vinylene group, a substituted or unsubstituted vinylidene group and an ethynylene group; and
$R^{19}$ to $R^{21}$ are independently selected from the group consisting of a hydrogen atom, an alkyl group having 1 to 50 carbon atoms and a substituted or unsubstituted aryl group having 6 to 40 ring carbon atoms.
17. A polymer comprising a repeating unit derived from one or two or more selected from the group consisting of the polymerizable monomers according to one of 1 to 16.
18. The polymer according to 17 which has a number average molecular weight (Mn) or a weight average molecular weight (Mw) of $1.0 \times 10^3$ to $5.0 \times 10^3$.
19. A material for an organic device comprising the polymer according to 17 or 18.
20. A hole-injecting/transporting material comprising the polymer according to 17 or 18.
21. A material for an organic electroluminescence EL device comprising the polymer according to 17 or 18.
22. An organic electroluminescence device comprising one or a plurality of organic thin film layers comprising an emitting layer between a cathode and an anode and at least one layer of the organic thin film layers comprising the polymer according to 17 or 18.
23. The organic electroluminescence device according to 22 wherein the organic thin film layers comprise one or both of a hole-transporting layer and a hole-injecting layer, and one or both of the hole-transporting layer and the hole-injecting layer comprises the polymer according to 17 or 18.
24. The organic electroluminescence device according to 23 wherein one or both of the hole-transporting layer and the hole-injecting layer comprises the polymer according to 17 or 18 as a main component.
25. The organic electroluminescence device according to one of 22 to 24 wherein the emitting layer comprises one or both of a styrylamine compound and an arylamine compound.
26. The organic electroluminescence device according to one of 23 to 25 wherein the organic thin film layers comprise one or both of the hole-injecting layer and the hole-transporting layer and one or both of the hole-injecting layer and the hole-transporting layer comprises an acceptor material.
27. The organic electroluminescence device according to one of 22 to 26 which can emit blue light.

According to the invention, it is possible to provide a novel polymerizable monomer which gives a polymer which is useful as a hole-injecting/transporting material of an organic device, in particular, an organic EL device or the like, and is improved in device performance such as life and luminous efficiency, as well as a polymer having it as a repeating unit.

According to the invention, it is possible to provide an organic EL device which suffers only slight deterioration even when it is subjected to high-temperature driving which is particularly practical in applications of a display or illumination, and hence is suited for practical use.

Further, since a hole-injecting/transporting layer can be formed homogenously by a coating method which was difficult to be applied to a low-molecular hole-injecting material, the invention is effective for a reduction in cost and an increase in screen size in applications such as a display and illumination.

MODE FOR CARRYING OUT THE INVENTION

Hole-transporting units having a structure represented by the following formula (1) in which at least one of the aryl groups is a group represented by the formulas (2) to (7) are improved in hole mobility and heat resistance. However, these units have poor solubility in a solvent as they are, and hence, they could not ensure the viscosity required of a coating liquid and homogeneity of a coating film (pinholeless). Therefore, only a deposition process can be applied, and hence, an increase in screen size and a reduction in cost of a display or an illumination device in the future were difficult to be realized.

According to the invention, as for hole-transporting units having a structure represented by the following formula (1) in which at least one of the aryl groups is a group represented by the formulas (2) to (7), to hole-transporting units which are improved in hole mobility and heat resistance, by further adding a polymerizable functional group, solubility of the monomer in a polymerization solvent is enhanced, whereby a polymer can be synthesized at a high yield. Further, the resulting polymer has high solubility in a solvent, and hence, the viscosity required of a coating liquid and homogeneity of a coating film (pinholeless) can be ensured, whereby an increase in size and a reduction in cost of a display or illumination in the future become possible.

Further, the resulting polymer is effective as a hole-injecting/transporting material of an organic device, in particular, an organic EL device or the like. By using such a material, it has become possible to provide an organic EL device which is improved in device performance such as life and luminous efficiency and hence, useful in applications of a display or illumination. In particular, it has become possible to provide a practical organic EL device which suffers only a slight degree of deterioration even if it is subjected to practical high-temperature driving.

The invention will be explained in detail according to the following embodiments.
Embodiment 1: Novel polymerizable monomer (hereinafter referred to as polymerizable monomers (I) to (III)
Embodiment 2: Polymer
Embodiment 3: Material comprising the polymer (a material for an organic device, a hole-injecting/transporting material, a material for an organic electroluminescence device)
Embodiment 4: Organic electroluminescence device Embodiment 1

Novel Polymerizable Monomer

Polymerizable Monomer (I)
A polymerizable monomer represented by the following formula (1) in which at least one of $Ar^1$ to $Ar^3$ is a group represented by the following formula (2), and which is further substituted by one or more groups comprising a polymerizable functional group:

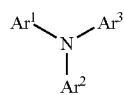
(1)

In the formula (1), $Ar^1$ to $Ar^3$ are independently a substituted or unsubstituted aryl group having 6 to 40 ring carbon atoms;

(2)

In the formula (2), $Ar^6$ is a substituted or unsubstituted aryl group having 6 to 40 ring carbon atoms and $Ar^4$ and $Ar^5$ are independently a substituted or unsubstituted arylene group having 6 to 40 ring carbon atoms.

The substituents of $Ar^1$ to $Ar^6$ when they are substituted are independently one or more groups selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring atoms, a mono- or dialkylamino group having an alkly group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 ring carbon atoms, an alkylarylamino group having 8 to 30 carbon atoms wherein the aryl part has 6 to 20 ring carbon atoms, a halogen atom, a nitro group, a cyano group and a hydroxyl group.

The polymerizable monomer represented by the formula (I) is characterized in $-Ar^4-Ar^5-A^6$ represented by the formula (2), in particular. Due to the incorporation of an arylene group having at least three aromatic rings, the resulting polymer has improved solubility in a solvent, whereby homogeneity of a coating film is improved, and high temperature resistance of an organic device, in particular, an organic EL device is improved.

As examples of this $-Ar^4-Ar^5-A^6$, a p-terphenyl-4-yl group, a p-terphenyl-3-yl group and a p-terphenyl-2-yl group are preferable, with a p-terphenyl-4-yl group being more preferable. The reason therefor is as follows. Interaction between side chains is suppressed to reduce the amount of an excimer or an exciplex generated. As a result, device performance such as hole-transporting properties of the polymer is improved, and the polymerization reaction ratio is improved to decrease the amount of monomers remaining unreacted, whereby durability and life of an organic device, in particular, an organic EL device, are improved.

Polymerizable Functional Group:
A polymerizable functional group is a functional group which causes a chemical reaction in which two or more molecules of one unit compound are bonded to form a compound of which the molecular weight is an integral multiple of the unit compound.

Examples of the polymerizable functional group include a group containing a double bond such as a substituted or unsubstituted vinyl group, a group which causes an addition reaction such as a substituted or unsubstituted acetylene group (ethynyl group), a group which causes a ring-openinging polymerization such as a substituted or unsubstituted norbornene skeleton-containing group (norbornenyl group), a group having a cyclic ether such as a substituted or unsubstituted epoxy group or a substituted or unsubstituted oxetane group, a group which causes a ring-openinging polymerization such as a functional group having a lactone structure or a lactum structure, and a group which causes a cyclopolymerization such as 1,ω-diene.

It is essential that the polymerizable monomer represented by the formula (1) or the group represented by the formula (2) be substituted by one or more groups comprising a polymerizable functional group. It is preferred that the monomer represented by the formula (1) or the group represented by the formula (2) be substituted by only one group comprising a polymerizable functional group. The reason therefor is as follows. If the polymerizable monomer is substituted by only one group comprising a polymerizable functional group, it is possible to conduct a polymerization reaction without causing a cross-linking reaction. Therefore, after the formation of a polymer, the polymer can be subjected to a purification treatment such as reprecipitation, and as a result, there is no monomer remaining unreacted or other impurities, exerting only small adverse effects on durability and life of an organic device, in particular, an organic EL device.

It is preferred that at least one aryl group selected from the group consisting of $Ar^1$ to $Ar^3$ in the formula (1) and $Ar^6$ in the formula (2) be substituted by the group comprising a polymerizable functional group. It is more preferred that $Ar^6$ be substituted by the group comprising a polymerizable functional group. Further, it is more preferred that a terminal aromatic ring contained in $Ar^6$ be substituted by the group comprising a polymerizable functional group. The reason therefor is as follows. Due to such substitution, solubility of the monomer or the resulting polymer in a solvent is improved, and as a result, not only homogeneity of a coating film of the polymer is improved but also the polymerization reaction ratio becomes high to decrease the amount of a monomer remaining unreacted, whereby durability and life of an organic device, in particular, an organic EL device, are improved.

Further, it is preferred that the polymerizable functional group and the part other than the terminal aromatic group contained in the aryl groups ($Ar^1$ to $Ar^3$ and $Ar^6$) be bonded to the terminal aromatic group at the para position (for example, if the terminal aromatic group is a phenylene group, at the $1^{st}$ and $4^{th}$ positions). The reason therefor is as follows. Due to such bonding, interaction between side chains is suppressed to reduce the amount of an excimer or an exciplex generated. As a result, device performance such as hole-transporting properties of the polymer is improved, and the polymerization reaction ratio is improved to decrease the amount of monomers remaining unreacted, whereby durability and life of an organic device, in particular, an organic EL device, are improved.

It is preferred that the group comprising a polymerizable functional group be selected from the following groups of (i) to (v).

Such polymerizable functional group has high reactivity, and hence, exhibits a high polymerization ratio. As a result, the amount of a monomer remaining unreacted is decreased, whereby durability and life of an organic device, in particular, an organic EL device, are improved.

(i) A group comprising a vinyl group or a vinylidene group shown below:

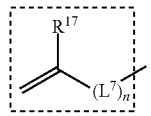

wherein $R^{17}$ is a hydrogen atom, an alkyl group having 1 to 50 carbon atoms or a substituted or unsubstituted aryl group having 6 to 40 ring carbon atoms; $L^7$ is a divalent linking group; and n is an integer of 0 or 1.

(ii) A group comprising an N-maleimide group shown below:

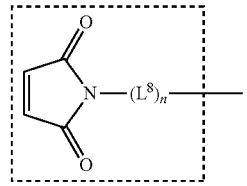

wherein $L^8$ is a divalent linking group and n is an integer of 0 or 1.

(iii) A group comprising a norbornenyl group shown below:

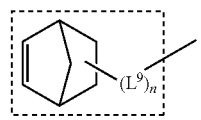

wherein $L^9$ is a divalent linking group and n is an integer of 0 or 1.

(iv) a group comprising an acetylenyl group shown below:

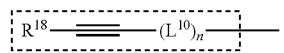

wherein $R^{18}$ is a hydrogen atom, an alkyl group having 1 to 50 carbon atoms or a substituted or unsubstituted aryl group having 6 to 40 ring carbon atoms; $L^{10}$ is a divalent linking group; and n is an integer of 0 or 1.

(v) A group comprising a cyclopolymerizable or ring-opening polymerizable functional group For example, a group having a substituted or unsubstituted norbornene skeleton other than the group (iii) (norbornenyl group), a group having a cyclic ether such as a group having a substituted or unsubstituted epoxy group or a substituted or unsubstituted oxetane group; a functional group having a lactone structure or a lactum structure; a group which causes ring-opening polymerization such as cyclooctatetraene group or a 1,5-cyclooctadiene group; and a group which causes cyclopolymerization such as a 1,ω-diene group, an o-divinylbenzene group and a 1,ω-diyne group can be mentioned.

In the group comprising the polymerizable functional group of the above formulas (i) to (iv), it is preferred that $L^7$ to $L^{10}$ be independently one linking group or a linking group formed by bonding, in an arbitral order, of two or more linking groups, the linking group being selected from the group consisting of the following divalent linking groups:
-$L^{11}$-, —O—, —C(=O)—, —C(=O)O—, —OC(=O)—, —C(=O)NR$^{19}$—, —NR$^{20}$C(=O)—, —NR$^{21}$—, —S—, —C(=S)—

$L^{11}$ is one group or a group formed by bonding, in an arbitral order, of two or more groups, the group being selected from the group consisting of a substituted or unsubstituted arylene group having 6 to 40 ring carbon atoms, a substituted or unsubstituted divalent heterocyclic group having 3 to 40 ring atoms, a substituted or unsubstituted alkylene group having 1 to 50 carbon atoms, a substituted or unsubstituted vinylene group, a substituted or unsubstituted vinylidene group and an ethynylene group; and $R^{19}$ to $R^{21}$ are independently selected from the group consisting of a hydrogen atom, an alkyl group having 1 to 50 carbon atoms and a substituted or unsubstituted aryl group having 6 to 40 ring carbon atoms.

—C(=O)— denotes a carbonyl bond and —C(=S)— denotes a thiocarbonyl bond.

By selecting such a linking group, solubility of the monomer in a polymerization solvent is improved, the polymerization reaction ratio is improved to decrease the amount of monomers remaining unreacted, whereby durability and life of an organic device, in particular, an organic EL device, are improved. Further, since solubility of the polymer in a coating solvent is improved to enable a homogenous coating film to be obtained, such linking group is suited to film formation for obtaining a large-size screen.

Specific examples of the groups relating to the formulas (1) and (2) and the groups comprising a polymerizable functional group represented by the formulas (i) to (iv) and the substituents are given below. Example of an aryl group:

Specific examples of the aryl groups include a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, biphenyl-2-yl group, biphenyl-3-yl group, biphenyl-4-yl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbipheny-4-yl group, 4"-t-butyl-p-terphenyl-4-yl group, fluorene-1-yl group, fluorene-2-yl group, fluorene-3-yl group and fluorene-4-yl group.

Of these, a phenyl group, 1-naphthyl group, 2-naphthyl group, 1-anthryl group, 2-anthryl group, 9-anthryl group, biphenyl-2-yl group, biphenyl-3-yl group, biphenyl-4-yl group, p-terphenyl-4-yl group, p-terphenyl-3-yl group, a p-terphenyl-2-yl group, o-tolyl group, m-tolyl group, p-tolyl group, fluorene-2-yl group and fluorene-3-yl group are preferable, with a phenyl group, 1-naphthyl group, 2-naphthyl group, m-tolyl group, p-tolyl group, fluorene-2-yl group and fluorene-3-yl group being more preferable.

Examples of an Arylene Group:

Specific examples of an arylene group are selected from divalent groups obtained by removing one aromatic hydrogen from the aryl group mentioned above.

Of these, a 1,4-phenylene group, a 1,3-phenylene group, a 1,4-naphthylene group, a 1,10-anthrylene group, a 4,4'-biphenylylene group, a 3,4'-biphenylylene group, a 4,3'-biphenylylene group, a 4,4"-p-terphenylylene group, a 3,4"-p-terphenylylene group, a 4,3"-p-terphenylylene group, a 1,4-tolylene group, a 4,4"-fluorenylene group and a 3,3"-fluorenylene group are preferable, with a 1,4-phenylene group, a 1,4-naphthylene group, a 1,10-anthrylene group, a 4,4'-biphenylylene group, a 3,4'-biphenylylene group, a 4,4"-p-terphenylylene group, a 2,7-fluorenylene group and a 3,6-fluorenylene group being more preferable.

Examples of the substituent when the aryl group and the arylene group, etc. mentioned above are substituted and examples of other groups are given below. The same groups as those mentioned above are omitted.

Specific examples of an alkyl group include a methyl group, an ethyl group, a propyl group, an isopropyl group, an n-butyl group, an isobutyl group, a sec-butyl group, a tert-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group and a 1,2,3-trihydroxypropyl group. A methyl group, an ethyl group, a propyl group, an isopropyl group, an n-butyl group, an isobutyl group, a sec-butyl group and a tert-butyl group are preferable.

Of these, a methyl group, an ethyl group, a propyl group, an isopropyl group, an n-butyl group, an s-butyl group and a t-butyl group are preferable.

Specific examples of a cycloalkyl group include a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a 1-adamantyl group, 2-adamantyl group, a 1-norbornyl group and a 2-norbornyl group. A cyclopentyl group and a cyclohexyl group are preferable.

The alkoxy group, the cycloalkoxy group and the aryloxy group are a group in which an oxygen atom intervenes at the substitution position of the alkyl group, the cycloalkyl group and the aryl group which are mentioned above.

The aralkyl group is a group in which the above-mentioned alkyl group is substituted by the above-mentioned aryl group.

Specific examples of the trialkylsilyl group include a trimethylsilyl group, a vinyldimethylsilyl group, a triethylsilyl group, a tripropylsilyl group, a propyldimethylsilyl group, a tributylsilyl group, a t-butyldimethylsilyl group, a tripentylsilyl group, a triheptylsilyl group and a trihexylsilyl group. A trimethylsilyl group and a triethylsilyl group are preferable. The silyl group may be substituted by the same or different alkyl groups.

Specific examples of the triarylsilyl group include a triphenylsilyl group and a trinaphthylsilyl group. A triphenylsilyl group is preferable. The silyl group may be substituted by the same or different aryl groups.

Specific examples of the dialkylarylsilyl group include a dimethylphenylsilyl group, a diethylphenylsilyl group, a dipropylphenylsilyl group, a dibutylphenylsilyl group, a dipentylphenylsilyl group, a diheptylphenylsilyl group, a dihexylphenylsilyl group, a dimethylnaphthylsilyl group, a dipropylnaphthylsilyl group, a dibutylnaphthylsilyl group, a dipentylnaphthylsilyl group, a diheptylnaphthylsilyl group, a dihexylnaphthylsilyl group, a dimethyl anthrylsilyl group, a diethylanthrylsilyl group, a dipropylanthrylsilyl group, a dibutylanthrylsiyl group, a dipentylanthrylsilyl group, a diheptylanthrylsilyl group, a dihexylanthrylsilyl group and a diphenylmethyl group. A dimethylphenylsilyl group and a diethylphenylsilyl group are preferable.

Specific examples of the alkyldiarylsilyl group include a methyldiphenylsilyl group, an ethyldiphenylsilyl group, a propyldiphenylsilyl group, a butyldiphenylsilyl group, a pentyldiphenylsilyl group and a heptyldipheny silyl group. A methyldiphenylsilyl group and an ethyldiphenylsilyl group are preferable.

Examples of the heterocyclic group include a 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiadinyl group, 2-phenothiadinyl group, 3-phenothiadinyl group, 4-phenothiadinyl group, 10-phenothiadinyl group, 1-phenoxadinyl group, 2-phenoxadinyl group, 3-phenoxadinyl group, 4-phenoxadinyl group, 10-phenoxadinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group and 4-t-butyl-3-indolyl group.

Of these, a 1-pyrrolyl group, 2-pyrrolyl group, 3-pyrrolyl group, 1-carbazolyl group, 2-carbazolyl group, 3-carbazolyl group, 4-carbazolyl group and 9-carbazolyl group are preferable.

As the mono- or dialkylamino group, an amino group which is substituted by the above-mentioned alkyl group is mentioned.

As the mono- or diarylamino group, an amino group which is substituted by the above-mentioned aryl group is mentioned.

As the alkylarylamino group, an amino group which is substituted by the above-mentioned alkyl group and the above-mentioned aryl group is mentioned.

Specific examples of a halogen atom include fluorine, chlorine and bromine.

Of these, fluorine is preferable. The reason therefor is that, since fluorine allows the surface tension of the resulting polymer to be lowered, a more homogeneous coating film can be formed.

Further, in the alkyl group, the cycloalkyl group, the aryl group, the alkoxy group, the cycloalkoxy group, the aryloxy group having 6 to 30 ring carbon atoms, the aralkyl group, the heterocyclic group, the mono- or dialkylamino group, the mono- or diarylamino group, the alkylarylamino group, the trialkylsilyl group, the triarylsilyl group, the dialkylarylsilyl group or the alkyldiarylsilyl group as mentioned above, the hydrogen atom may be substituted by a halogen atom. Of the halogen atoms, a fluorine atom is preferable. The reason therefor is that, since fluorine allows the surface tension of the resulting polymer to be lowered, a more homogeneous coating film can be formed.

Polymerizable Monomer (II):

A polymerizable monomer represented by the following formula (1) wherein at least one of $Ar^1$ to $Ar^3$ is a group represented by the formula (3) and which is substituted by one or more groups comprising a polymerizable functional group.

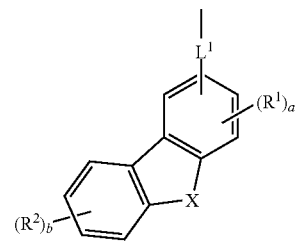

(3)

wherein $L^1$ is a single bond or a substituted or unsubstituted arylene group having 6 to 50 ring carbon atoms;

the substituents of $L^1$ when it is substituted are one or more groups selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring atoms, a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 ring carbon atoms, an alkylarylamino group having 8 to 30 carbon atoms wherein the aryl part has 6 to 20 ring carbon atoms, a halogen atom, a nitro group, a cyano group and a hydroxyl group;

X is a substituted or unsubstituted hetero atom;

the substituents of X when it is substituted are one or more groups selected from the group consisting of a hydrogen atom, an alkyl group having 1 to 20 carbon atoms, a cycloalkyl group having 3 to 10 carbon atoms, an aryl group having 6 to 30 ring carbon atoms, an aralkyl group having 7 to 31 carbon atoms wherein the aryl part has 6 to 30 ring carbon atoms and a heterocyclic group having 3 to 30 ring atoms;

$R^1$ and $R^2$ are independently a group selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring atoms, a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 ring carbon atoms, an alkylarylamino group having 8 to 30 carbon atoms wherein the aryl part has 6 to 20 ring carbon atoms, a halogen atom, a nitro group, a cyano group and a hydroxyl group;

a is an integer of 0 to 3; and b is an integer of 0 to 4.

By allowing at least one of $Ar^1$ to $Ar^3$ in the formula (1) to be a group represented by the formula (3), not only performance required of a device such as hole-transporting properties but also reduction resistance (resistance to electrons) of the resulting polymer is improved, whereby durability and life of an organic device, in particular, an organic EL device, are improved.

In the formula (3), X is a substituted or unsubstituted hetero atom. The hetero atom means an atom other than hydrogen and oxygen, and is preferably N, O, S, P, As, Sb, Bi, O, S, Se, Te, Po, Si, Ge, Sn and B. More preferably, the hetero atom is N, O and S. When the hetero atom is N, $NAr^7$ in which the following $Ar^7$ is substituted is preferable.

In the polymerizable monomer (II), it is preferred that the group represented by the above formula (3) be selected from groups represented by the following formulas (4) to (6).

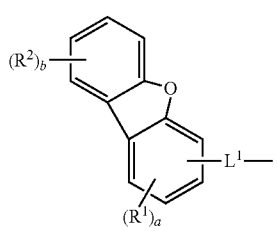

(4)

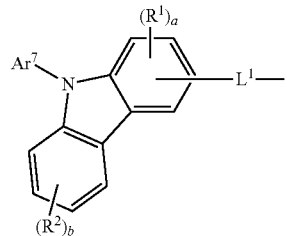

(5)

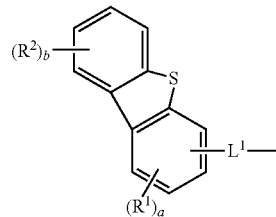

(6)

$L^1$, $R^1$, $R^2$, a and b are as defined in the above formula (3).

$Ar^7$ is a group selected from the group consisting of a hydrogen atom, an alkyl group having 1 to 20 carbon atoms, a cycloalkyl group having 3 to 10 carbon atoms, an aryl group having 6 to 30 ring carbon atoms, an aralkyl group having 7 to 31 carbon atoms wherein the aryl part has 6 to 30 ring carbon atoms and a heterocyclic group having 3 to 30 ring atoms.

By selecting the group represented by the formula (3) from groups represented by the formulas (4) to (6), not only performance required of a device such as hole-transporting properties but also reduction resistance (resistance to electrons) of the resulting polymer is improved, whereby durability and life of an organic device, in particular, an organic EL device, are improved.

The polymerizable functional group and the group comprising a polymerizable functional group are explained above referring to the polymerizable monomer (I). Therefore, a detailed explanation thereof is omitted.

It is essential that the polymerizable monomer represented by the formula (1) or the groups represented by the formulas (3) and (4) to (6) be substituted by one or more groups comprising a polymerizable functional group.

It is preferred that the polymerizable monomer or the group be substituted by only one group comprising a polymerizable functional group. The reason therefor is as follows. If the polymerizable monomer is substituted by only one group comprising a polymerizable functional group, it is possible to conduct a polymerization reaction without causing a cross-linking reaction. Therefore, after the formation of a polymer, the polymer can be subjected to a purification treatment such as reprecipitation, and as a result, there is no monomer remaining unreacted or other impurities, exerting only small adverse effects on durability and life of an organic device, in particular, an organic EL device.

It is preferred that, in the polymerizable monomer (II), at least one aryl group selected from the group consisting of $Ar^1$ to $Ar^3$ in the formula (1) and $Ar^7$ in the formula (5) be substituted by the group comprising a polymerizable functional group.

The benzene ring represented by the formula (3) may be substituted by the group comprising a polymerizable functional group. However, in order to further improve reduction resistance (resistance to electrons), it is preferred that the benzene ring be not substituted. The benzene rings represented by the formulas (4) to (6) be substituted by the group comprising a polymerizable functional group. However, In order to further improve reduction resistance (resistance to electrons), it is more preferred that the benzene rings represented by the formulas (4) to (6) be not substituted by the group comprising a polymerizable functional group and that only $Ar^7$ in the formula (5) be substituted.

Further, it is preferred that the group comprising a polymerizable functional group and the part other than the terminal aromatic group contained in the above-mentioned aryl groups ($Ar^1$ to $Ar^3$ and $Ar^7$) be bonded to the terminal aromatic group at the para position (for example, if the terminal aromatic group is a phenylene group, at the $1^{st}$ and $4^{th}$ positions). The reason therefor is as follows. Due to such bonding, interaction between side chains is suppressed to reduce the amount of an excimer or an exciplex generated. As a result, device performance such as hole-transporting properties of the polymer is improved, and the polymerization reaction ratio is improved to decrease the amount of monomers remaining unreacted, whereby durability and life of an organic device, in particular, an organic EL device are improved.

$L^1$ is substituted at an arbitral position of the $1^{st}$ to the $4^{th}$ positions of the dibenzofuran skeleton in the formula (4) or the dibenzothiophene skeleton in the formula (6). Of these positions, the $2^{nd}$ and $4^{th}$ positions are preferable, with the $4^{th}$ position being more preferable.

$L^1$ is substituted at an arbitral position of the $1^{st}$ to the $4^{th}$ positions of the carbazole skeleton in the formula (5), and the $2^{nd}$ and the $3^{rd}$ positions are preferable, with the $3^{rd}$ position being further preferable. The reasons therefor are as follows. Synthesis is easy, and due to easiness in purification, a high degree of purity can be attained easily, and as a result, durability and life of an organic device, in particular, an organic EL device, are improved.

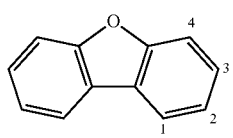

Dibenzofuran Substitution Position

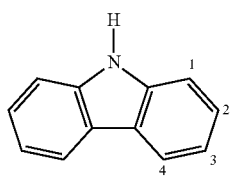

Carbazole Substitution Position

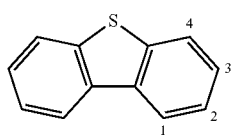

Dibenzothiophene Substitution Position

It is preferred that $L^1$ be selected from the group consisting of a phenylene group, a naphthylene group, a biphenylylene group, a terphenylylene group and a fluorenylene group.

By selecting these groups, the resistance to high temperatures of the polymer is improved, whereby durability and life of an organic device, in particular, an organic EL device, are further improved.

Examples of the aryl group, the arylene group, the substituents or the like in the formulas (3) to (6) are the same as those in the polymerizable monomer (I).

Polymerizable Monomer (III)

A polymerizable monomer represented by the formula (1) wherein at least one of $Ar^1$ to $Ar^3$ is a group represented by the following formula (7) and which is further substituted by one or more groups comprising a polymerizable functional group:

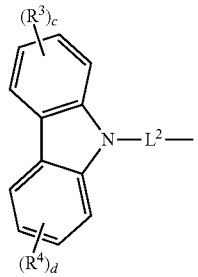

(7)

wherein $R^3$ and $R^4$ are independently a group selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring atoms, a mono- or dialkylamino group having an alkyl group having 1 to 20 carbon atoms, a mono- or diarylamino group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 ring carbon atoms, an alkylarylamino group having 8 to 30 carbon atoms wherein the aryl part has 6 to 20 ring carbon atoms, a halogen atom, a nitro group, a cyano group and a hydroxyl group;

c and d are independently an integer of 0 to 4;

$L^2$ is a substituted or unsubstituted arylene group having 10 to 50 ring carbon atoms; and the substituents of $L^2$ when it is substituted are one or more groups selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring atoms, a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 ring carbon atoms, an alkylarylamino group having 8 to 30 carbon atoms wherein the aryl part has 6 to 20 ring carbon atoms, a halogen atom, a nitro group, a cyano group and a hydroxyl group.

In the polymerizable monomer (III), by allowing at least one of $Ar^1$ to $Ar^3$ in the formula (1) to be a group represented by the formula (7), synthesis of the monomer becomes easy, and not only performance required of a device such as hole-transporting properties but also reduction resistance (resistance to electrons) of the resulting polymer is improved, whereby durability and life of an organic device, in particular, an organic EL device, are improved.

The group comprising a polymerizable functional group and the polymerizable functional group are explained above referring to the polymerizable monomer (I). Therefore, a detailed explanation thereof is omitted.

It is essential that the polymerizable monomer represented by the formula (1) or the group represented by the formula (7) be substituted by one or more groups comprising a polymerizable functional group. It is preferred that the monomer or the group be substituted by only one group comprising a polymerizable functional group. The reason therefor is as follows. If the polymerizable monomer or the group is substituted by only one group comprising a polymerizable functional group, it is possible to conduct a polymerization reaction without causing a cross-linking reaction. Therefore, after the formation of a polymer, the polymer can be subjected to a purification treatment such as reprecipitation, and as a result, there is no monomer remaining unreacted or other impurities, exerting only small adverse effects on durability and life of an organic device, in particular, an organic EL device.

It is preferred that, in the polymerizable monomer (III), at least one aryl group selected from the group consisting of $Ar^1$ to $Ar^3$ in the formula (1) be substituted by the group comprising a polymerizable functional group. The group represented by the formula (7) may be substituted by the group comprising a polymerizable functional group. However, in order to further improve reduction resistance (resistance to electrons), it is preferred that the group represented by the formula (7) be not substituted.

Further, it is preferred that the group comprising a polymerizable functional group and the part other than the terminal aromatic group contained in the above-mentioned aryl groups ($Ar^1$ to $Ar^3$) be bonded to the terminal aromatic group at the para position (for example, if the terminal aromatic group is a phenylene group, at the $1^{st}$ and $4^{th}$ positions). The reason therefor is as follows. Due to such bonding, interaction between side chains is suppressed to reduce the amount of an excimer or an exciplex generated. As a result, device performance such as hole-transporting properties of the polymer is improved, and the polymerization reaction ratio is improved to decrease the amount of monomers remaining unreacted, whereby durability and life of an organic device, in particular, an organic EL device, are improved.

Examples of the aryl group, the arylene group, the substituent and other groups in the polymerizable monomer (III) are the same as those for the polymerizable monomer (I).

It is preferred that $L^2$ be selected from the group consisting of a naphthylene group, a biphenylene group, a terphenylene group and a fluorenylene group.

By selecting such a functional group, the resistance to high temperatures of the polymer is improved, whereby durability and life of an organic device, in particular, an organic EL device, will be further improved.

The polymerizable monomer of the invention includes the following embodiments in which the polymerizable monomers (I) to (III) are combined.

In the formula (1), it is preferred that at least one of the groups of $Ar^1$ to $Ar^3$ be the group represented by the formula (2) and at least one of the remaining groups of $Ar^1$ to $Ar^3$ be the group represented by the formula (3). In particular, in the formula (1), it is more preferred that the group represented by the formula (3) be selected from the group consisting of the groups represented by the formulas (4) to (6).

Due to such a configuration, solubility of the resulting polymer in a solvent is improved, and as a result, not only homogeneity of a coating film of the polymer is improved but also resistance to high temperatures of an organic device, in particular, an organic EL device, is improved. Further, since not only device performance, such as hole-injecting properties, but also reduction resistance (resistance to electrons) of the resulting polymer is improved, durability and life of an organic device, in particular, an organic EL device, are improved.

It is preferred that the polymerizable monomer represented by the formula (1) be a polymerizable monomer in which at least one of the groups of $Ar^1$ to $Ar^3$ be the group represented by the formula (2) and at least one of the remaining groups of $Ar^1$ to $Ar^3$ be the group represented by the formula (7).

Due to such a configuration, solubility of the resulting polymer in a solvent is improved, and as a result, not only homogeneity of a coating film of the polymer is improved but also resistance to high temperatures of an organic device, in particular, an organic EL device, is improved. Further, synthesis of the monomer becomes easy, and since not only device performance, such as hole-injecting properties, but also reduction resistance (resistance to electrons) of the resulting polymer is improved, durability and life of an organic device, in particular, an organic EL device, are improved.

In the formula (1), it is preferred that at least one of the groups of $Ar^1$ to $Ar^3$ be the group represented by the formula (3) and at least one of the remaining groups of $Ar^1$ to $Ar^3$ be the group represented by the formula (7). In particular, it is further preferred that the group represented by the formula (3) be selected from the group consisting of the groups represented by the formulas (4) to (6) and at least one of the remaining groups of $Ar^1$ to $Ar^3$ be the group represented by the formula (7).

Due to such a configuration, synthesis of the monomer becomes easy, and since not only device performance, such as hole-injecting properties, but also reduction resistance of the resulting polymer is improved, durability and life of an organic device, in particular, an organic EL device, are improved.

Examples of the polymerizable monomers (I) to (III) of the invention will be given below:

23
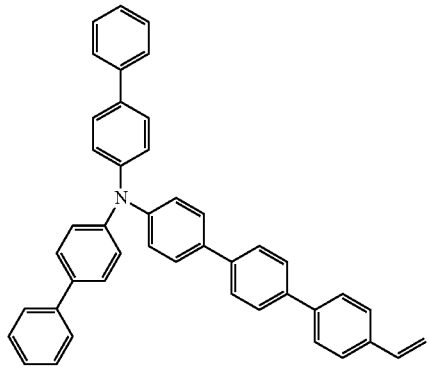
24
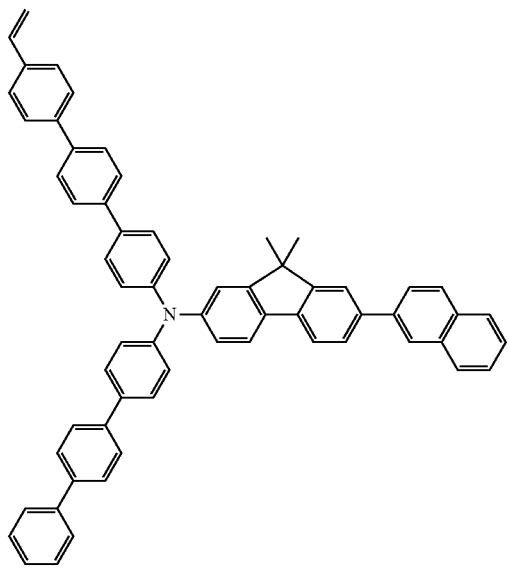 [SMILES: C=Cc1ccc(-c2ccc(-c3ccc(N(c4ccc(-c5ccc(-c6ccccc6)cc5)cc4)c4ccc5c(c4)C(C)(C)c4cc(-c6ccc7ccccc7c6)ccc4-5)cc3)cc2)cc1]
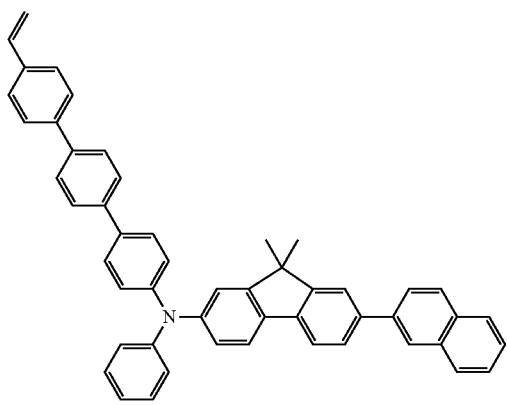
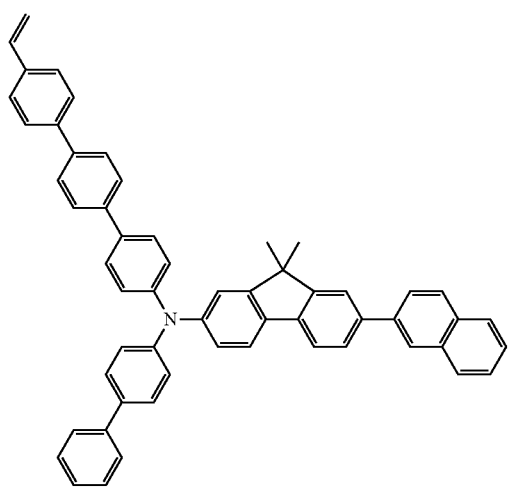
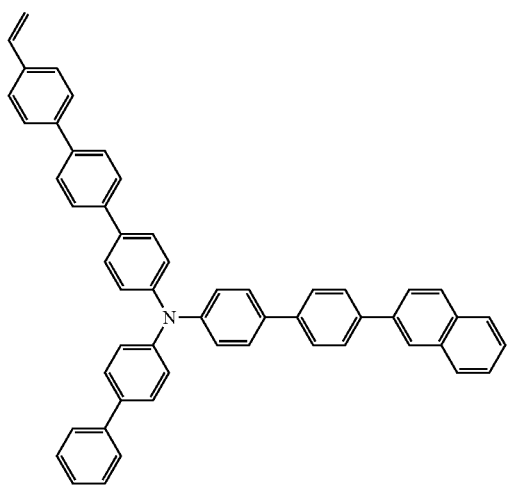
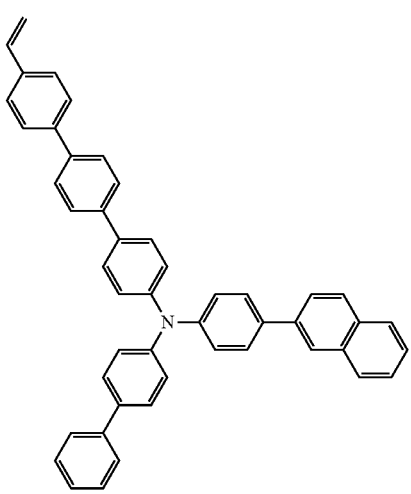

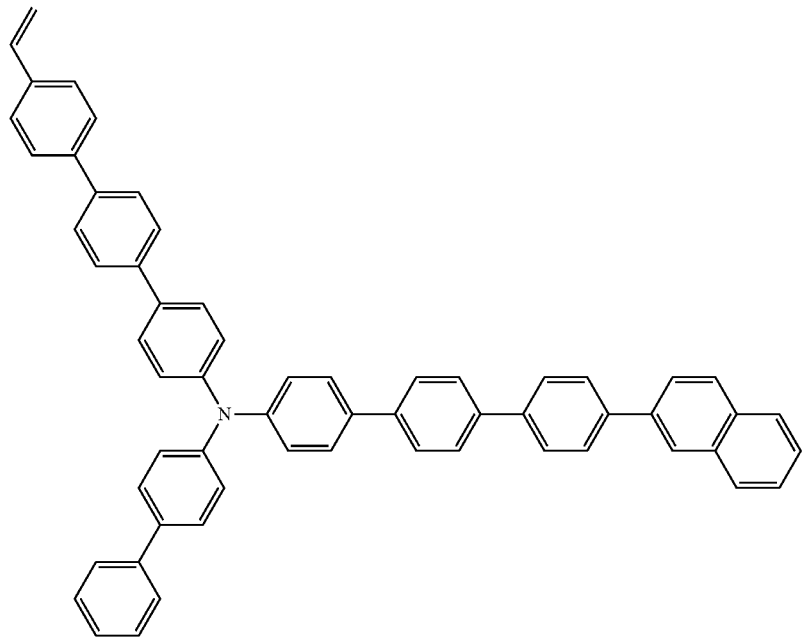
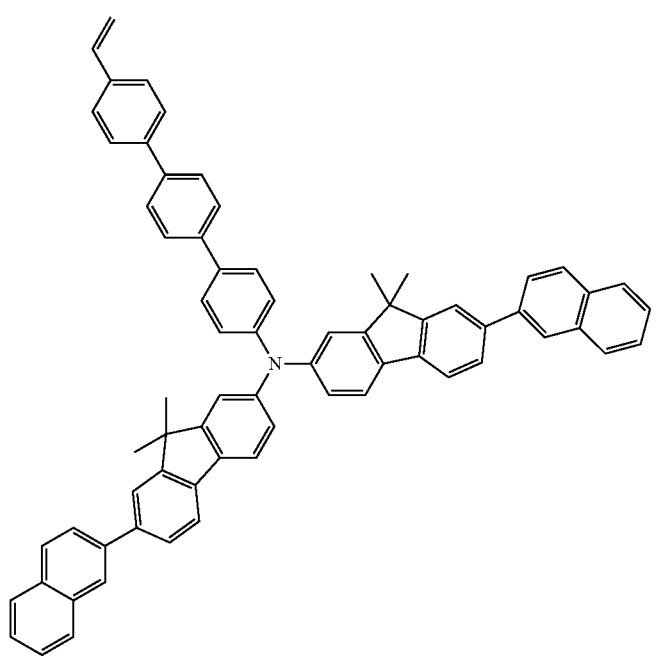

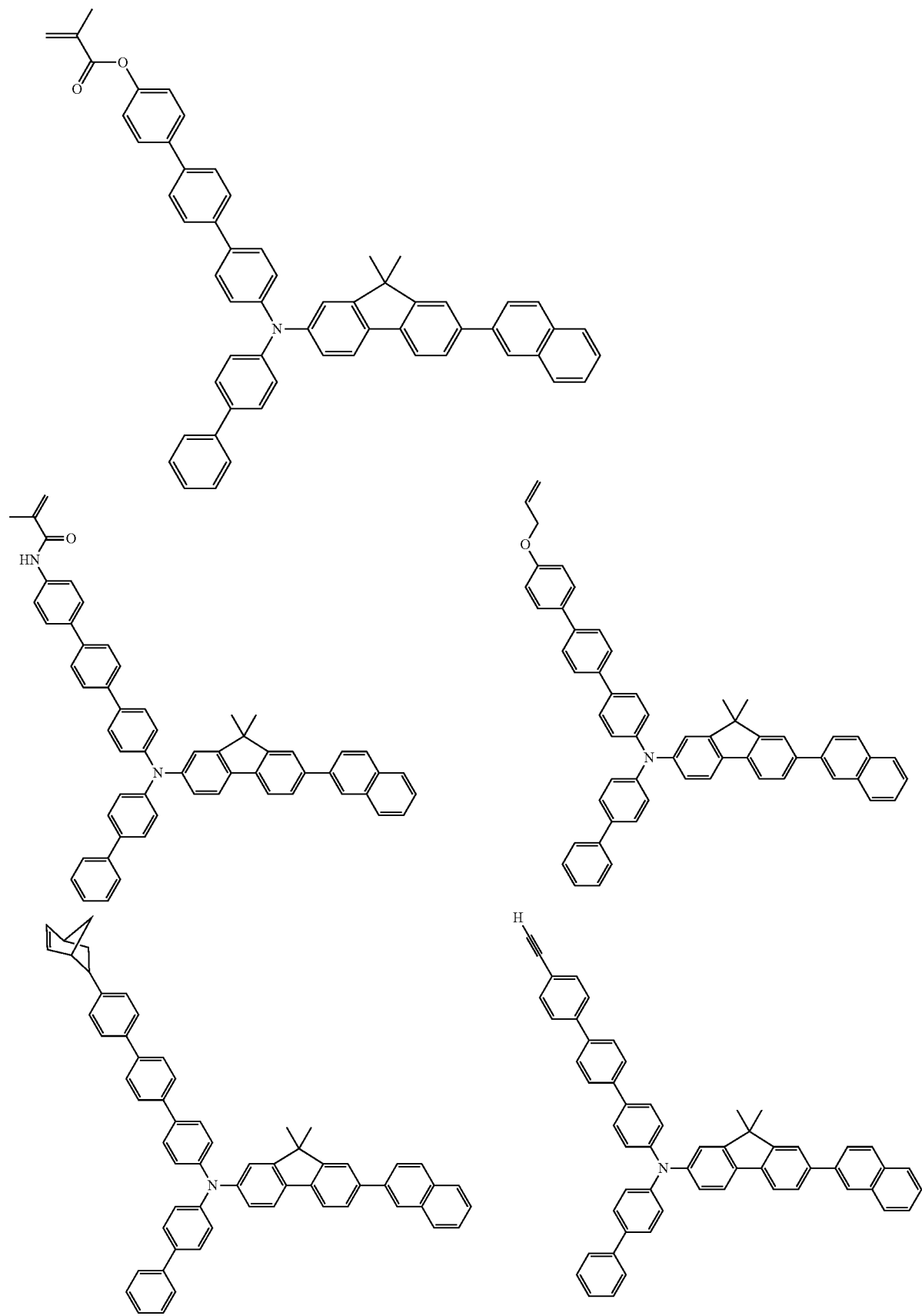

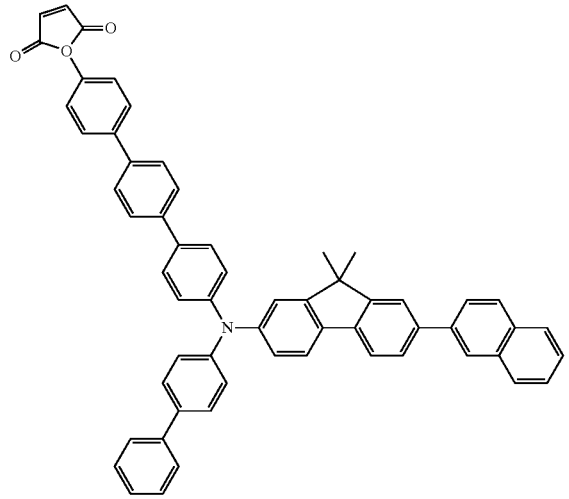
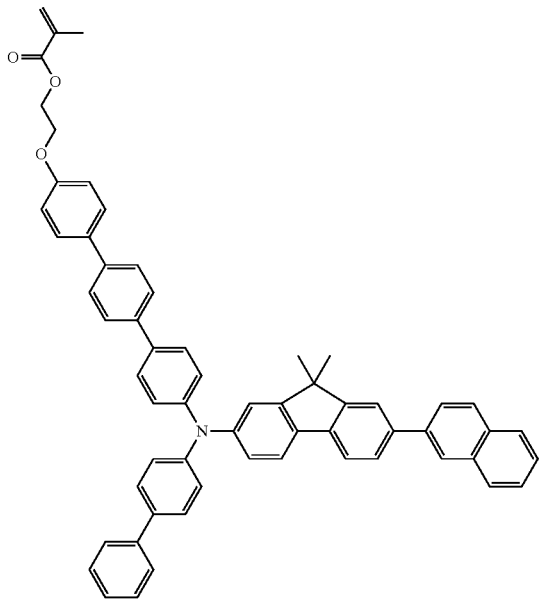
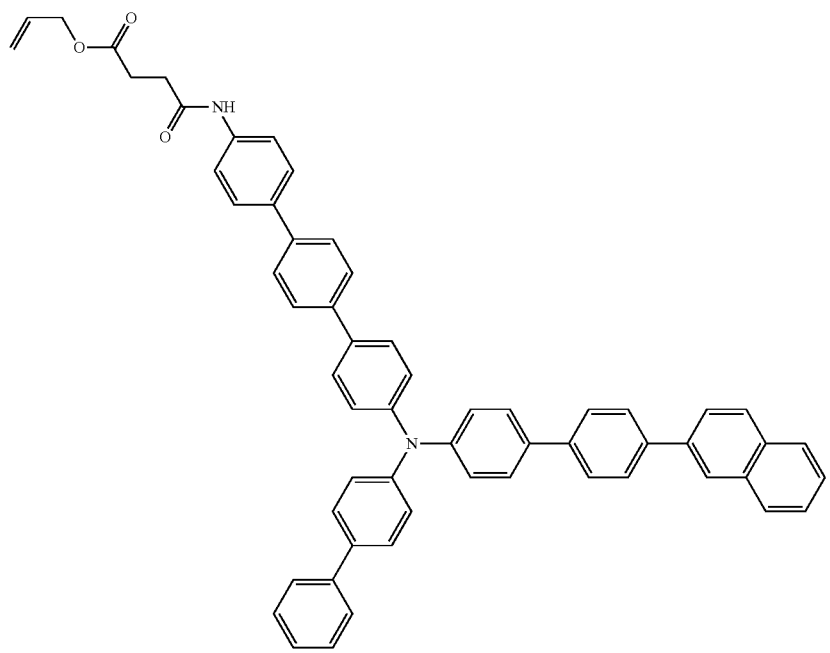
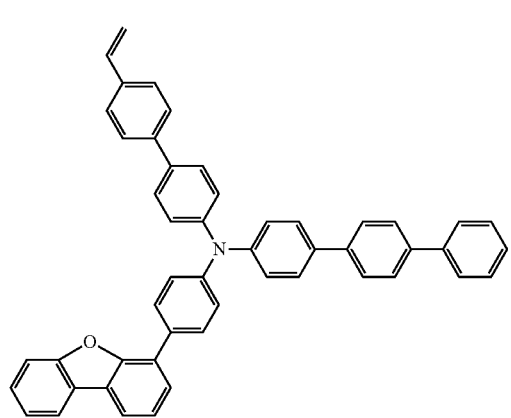
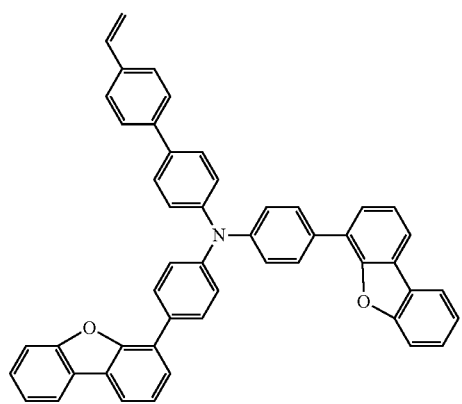 [SMILES: C=Cc1ccc(-c2ccc(N(c3ccc(-c4cccc5c4oc4ccccc45)cc3)c3ccc(-c4cccc5c4oc4ccccc45)cc3)cc2)cc1]

-continued
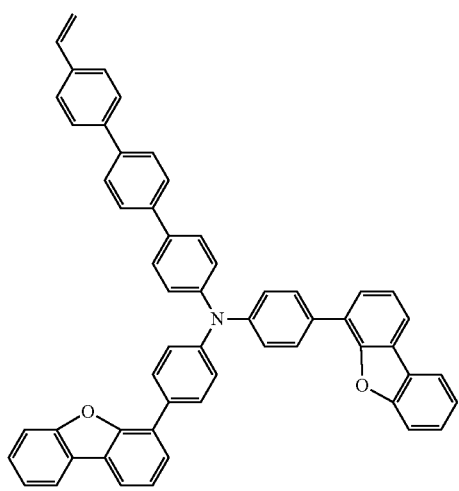 [SMILES: C=Cc1ccc(-c2ccc(-c3ccc(N(c4ccc(-c5cccc6c5oc5ccccc56)cc4)c4ccc(-c5cccc6c5oc5ccccc56)cc4)cc3)cc2)cc1]
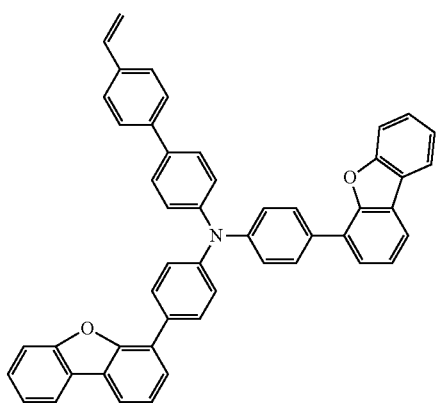
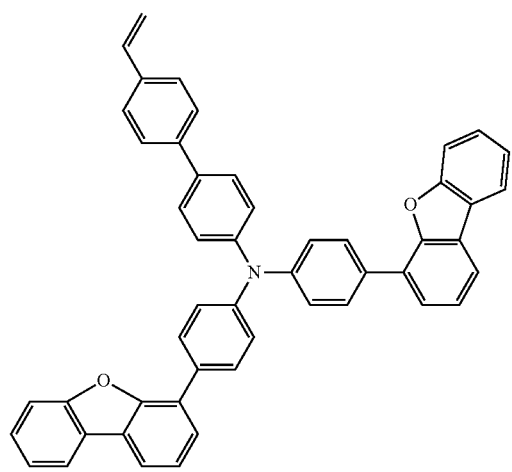
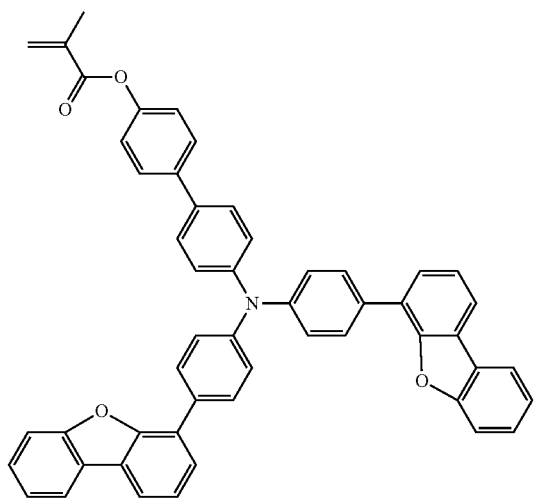
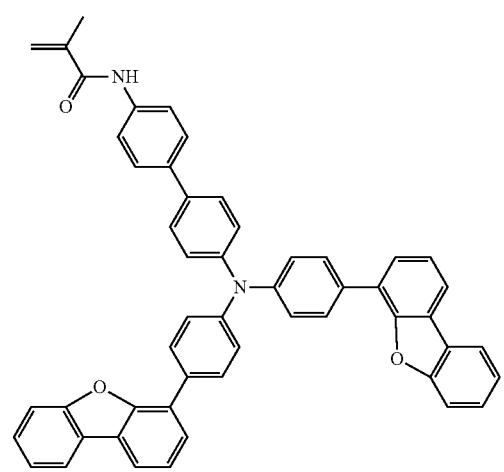 [SMILES: C=C(C)C(=O)Nc1ccc(-c2ccc(N(c3ccc(-c4cccc5c4oc4ccccc45)cc3)c3ccc(-c4cccc5c4oc4ccccc45)cc3)cc2)cc1]
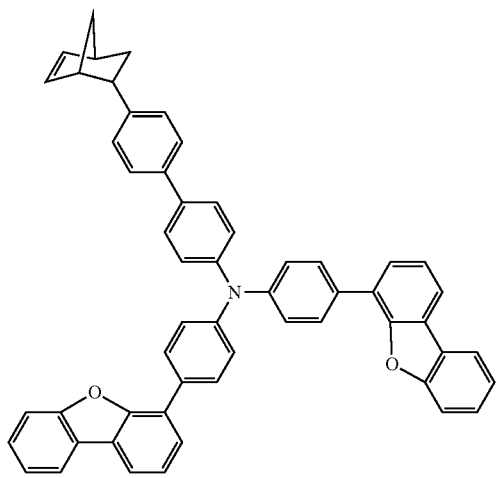

-continued
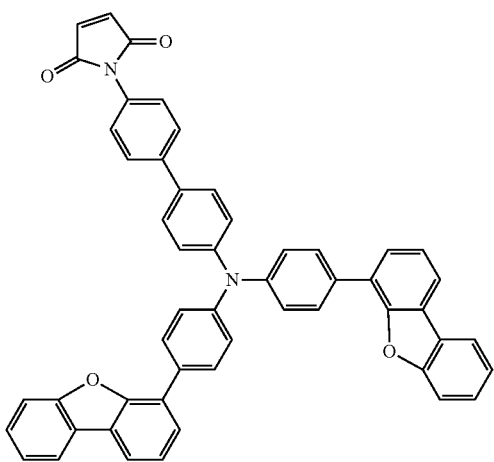 [SMILES: C1=CC2CC1CC2c1ccc(-c2ccc(N(c3ccc(-c4cccc5c4oc4ccccc45)cc3)c3ccc(-c4cccc5c4oc4ccccc45)cc3)cc2)cc1]
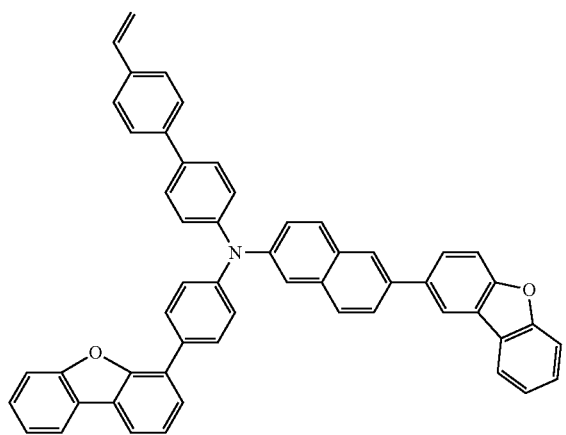
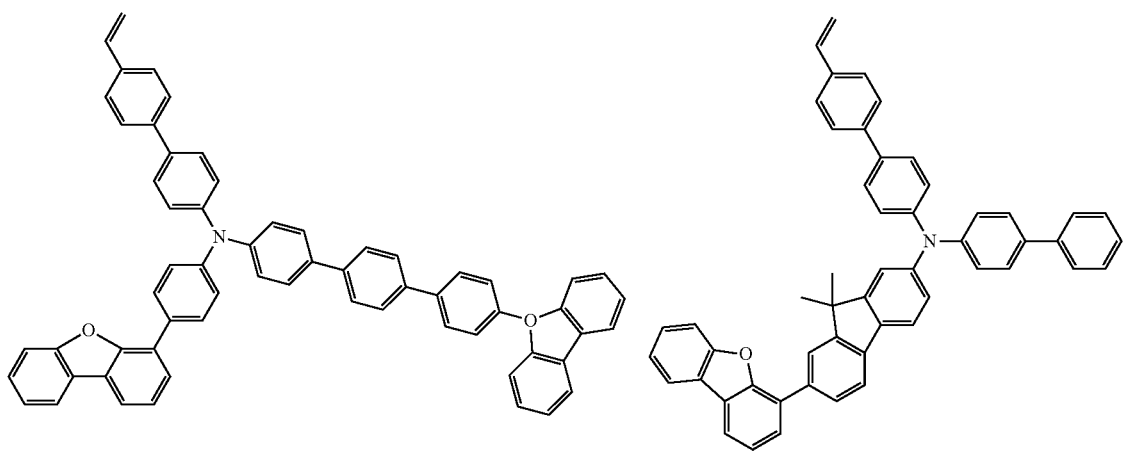
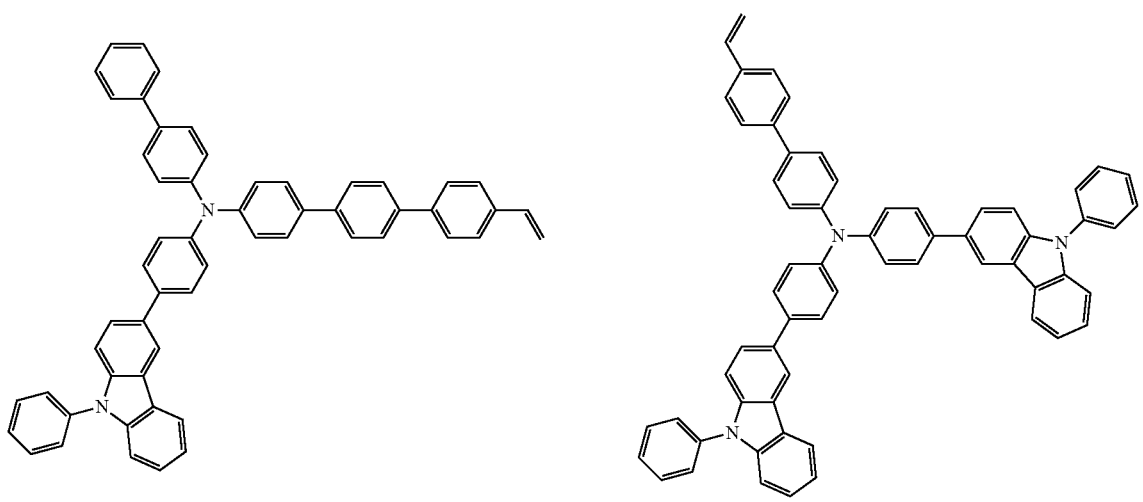

-continued
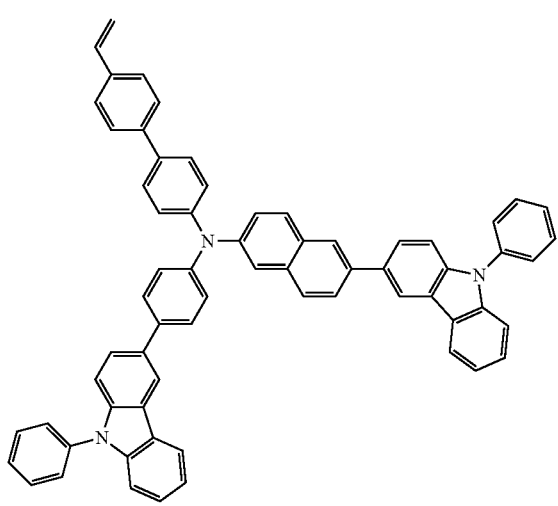
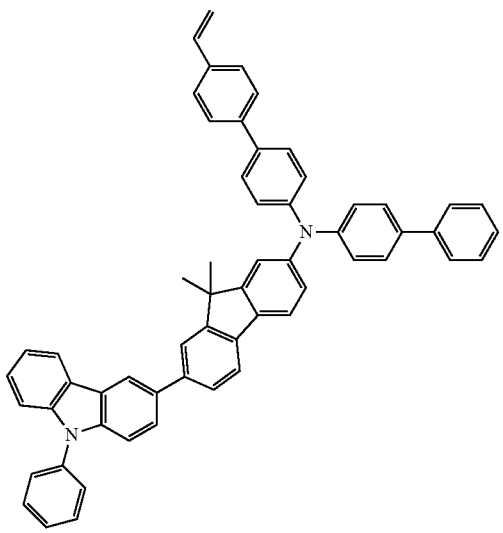
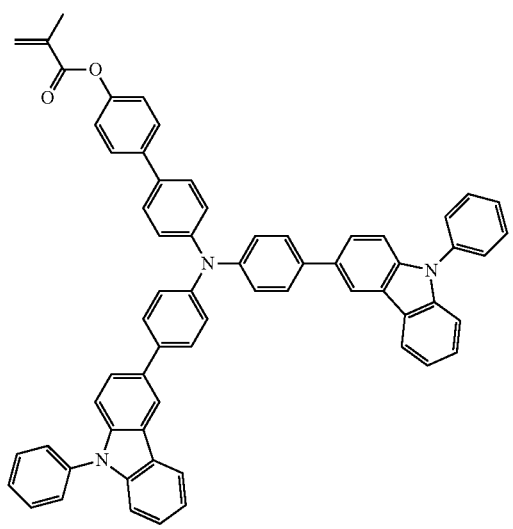 [SMILES: C=C(C)C(=O)Oc1ccc(-c2ccc(N(c3ccc(-c4ccc5c(c4)c4ccccc4n5-c4ccccc4)cc3)c3ccc(-c4ccc5c(c4)c4ccccc4n5-c4ccccc4)cc3)cc2)cc1]
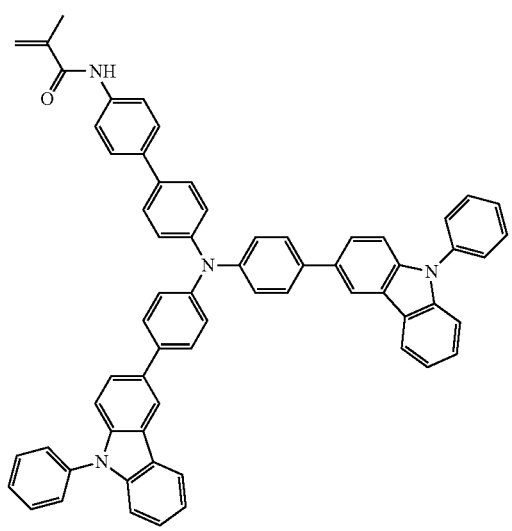 [SMILES: C=C(C)C(=O)Nc1ccc(-c2ccc(N(c3ccc(-c4ccc5c(c4)c4ccccc4n5-c4ccccc4)cc3)c3ccc(-c4ccc5c(c4)c4ccccc4n5-c4ccccc4)cc3)cc2)cc1]
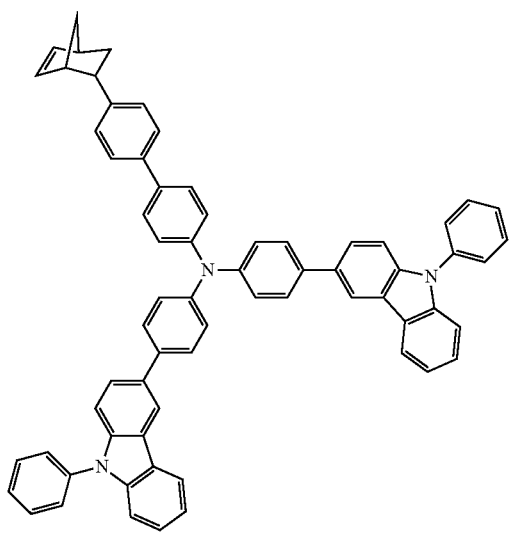
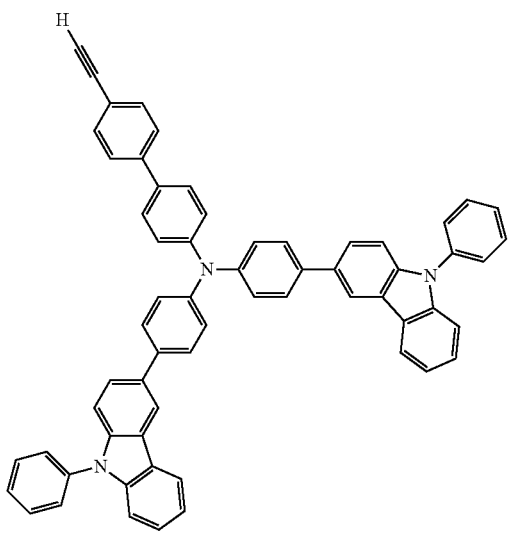

-continued
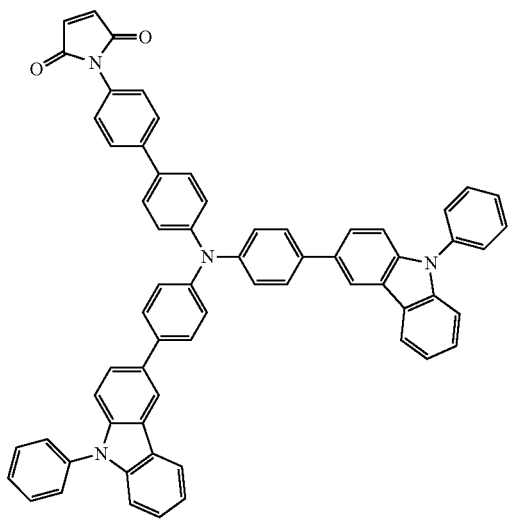 [SMILES: C1=CC2CC1CC2c1ccc(-c2ccc(N(c3ccc(-c4ccc5c(c4)c4ccccc4n5-c4ccccc4)cc3)c3ccc(-c4ccc5c(c4)c4ccccc4n5-c4ccccc4)cc3)cc2)cc1] 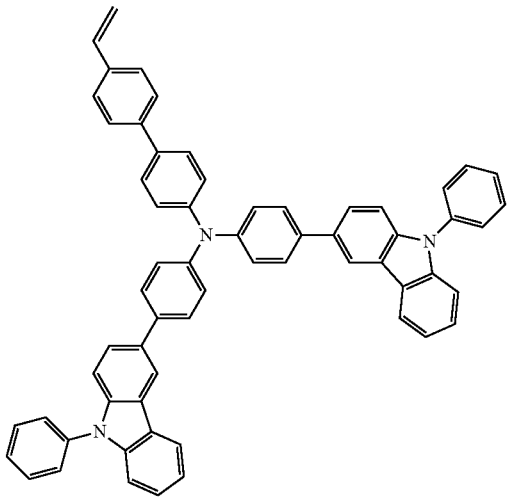
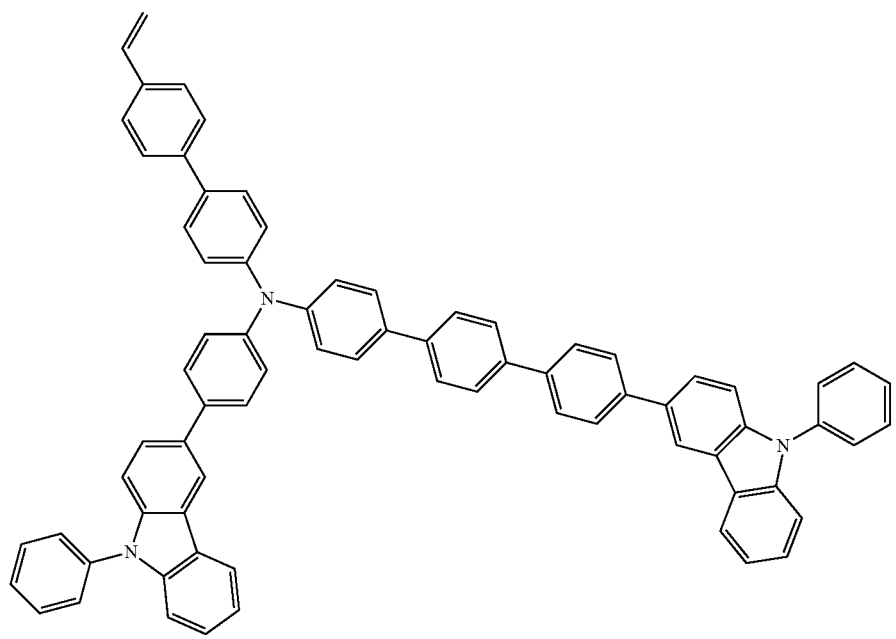
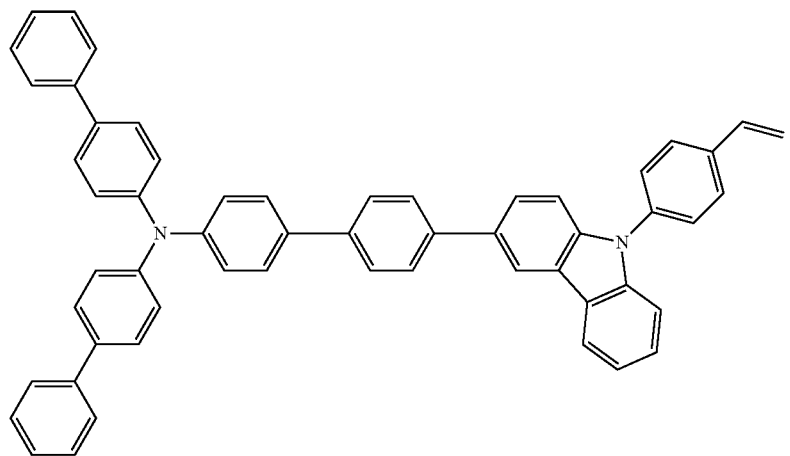

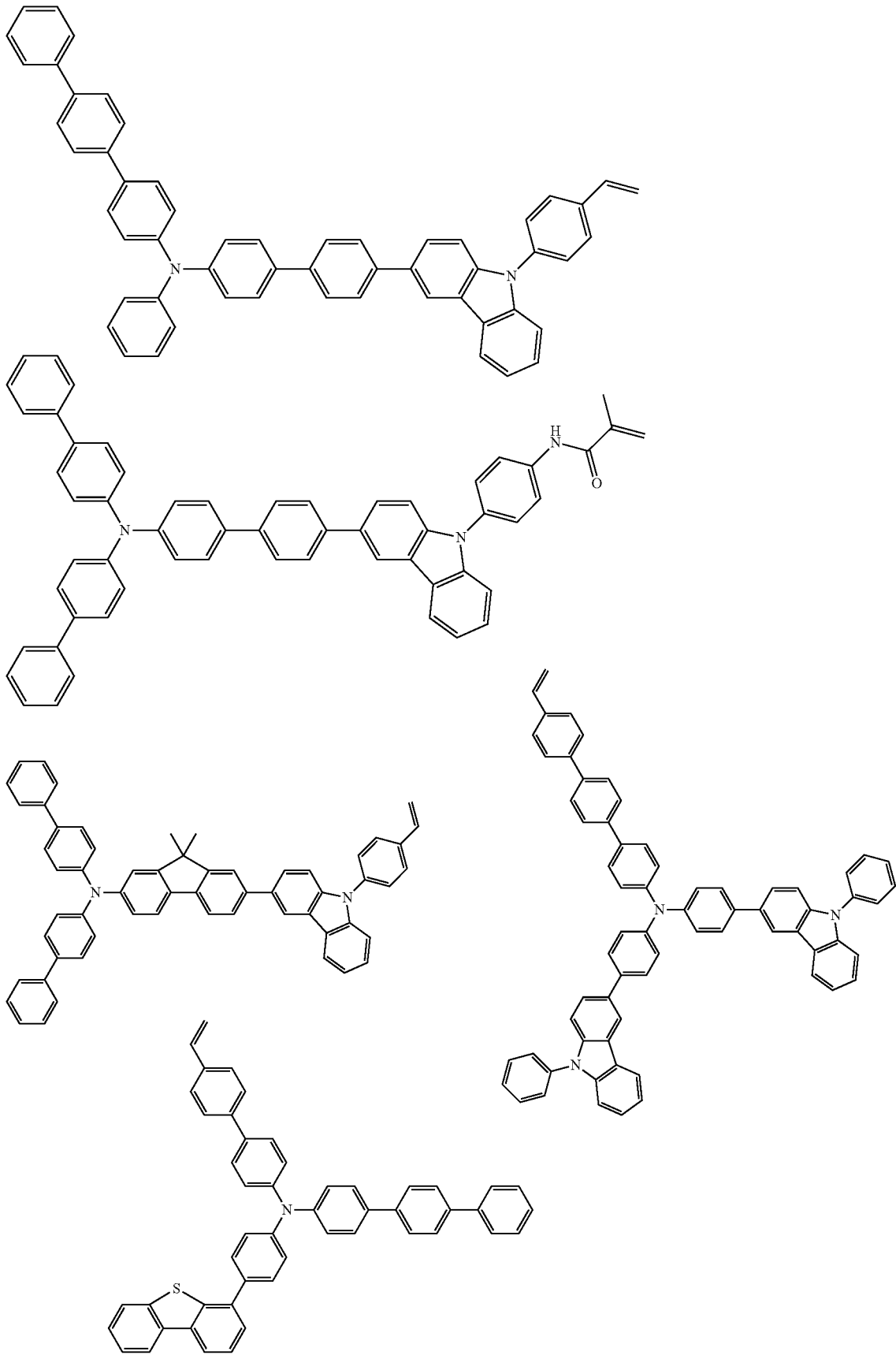

-continued
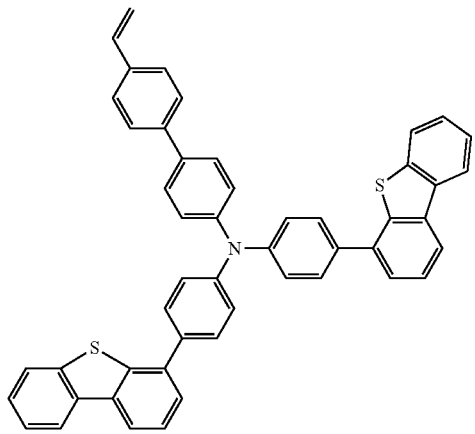 [SMILES: C=Cc1ccc(-c2ccc(N(c3ccc(-c4cccc5c4sc4ccccc45)cc3)c3ccc(-c4cccc5c4sc4ccccc45)cc3)cc2)cc1]
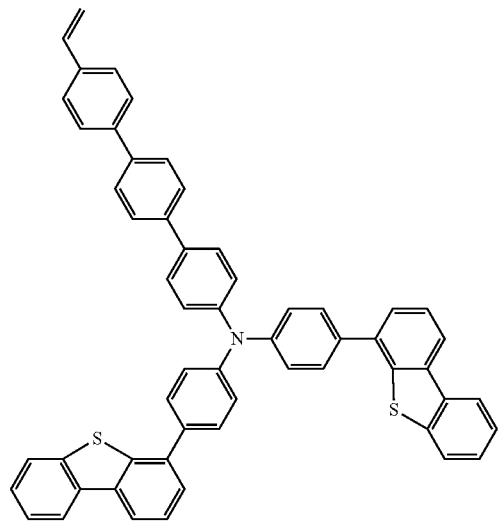
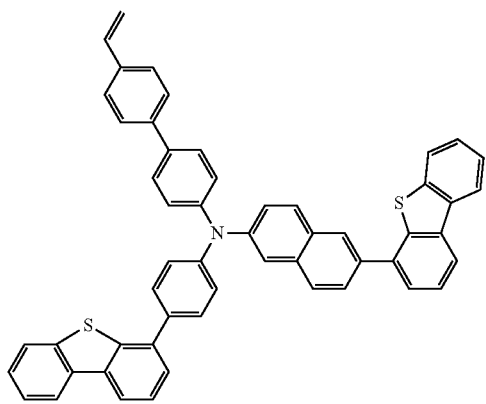
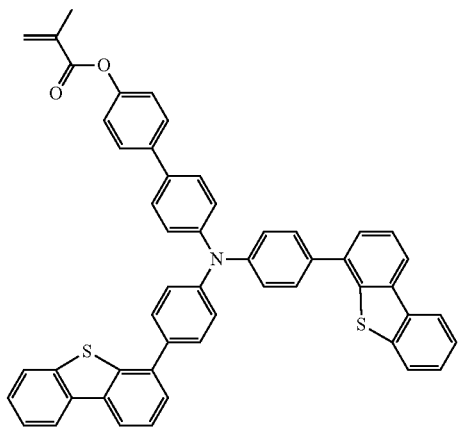
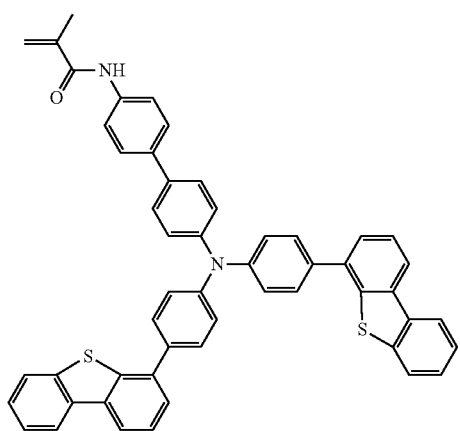
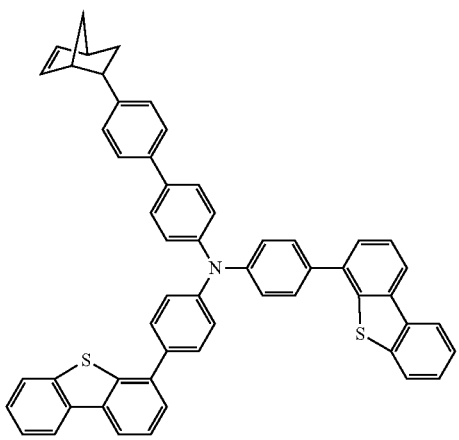

-continued
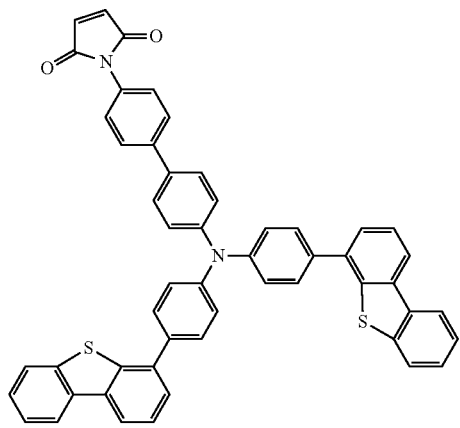
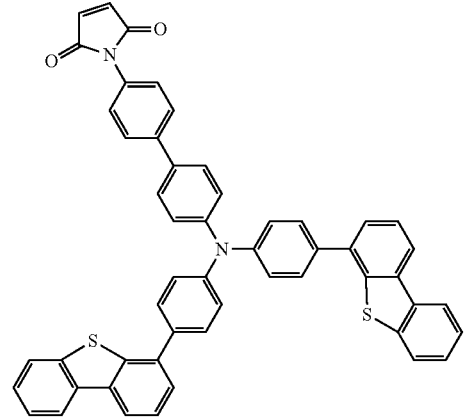
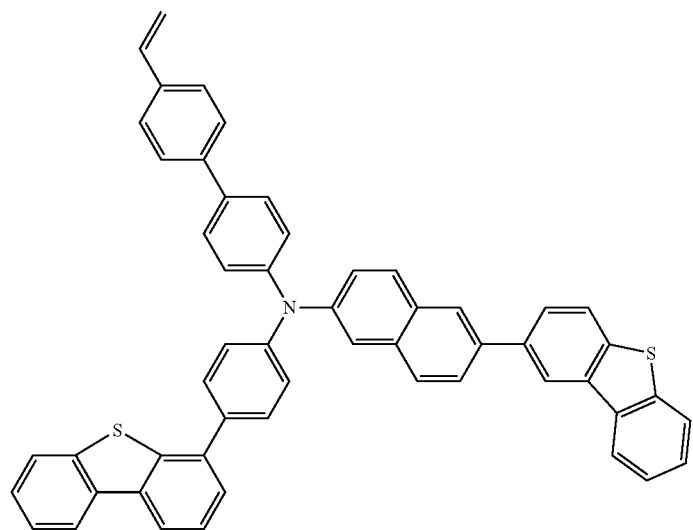
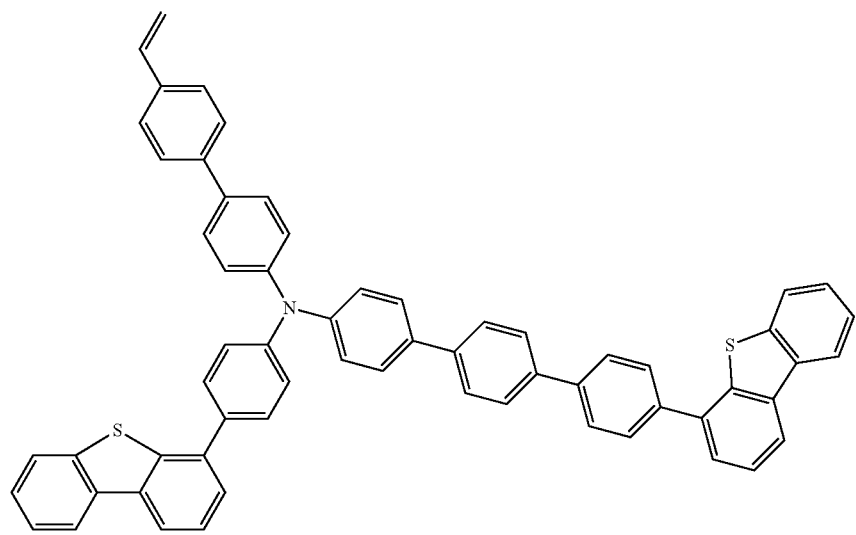

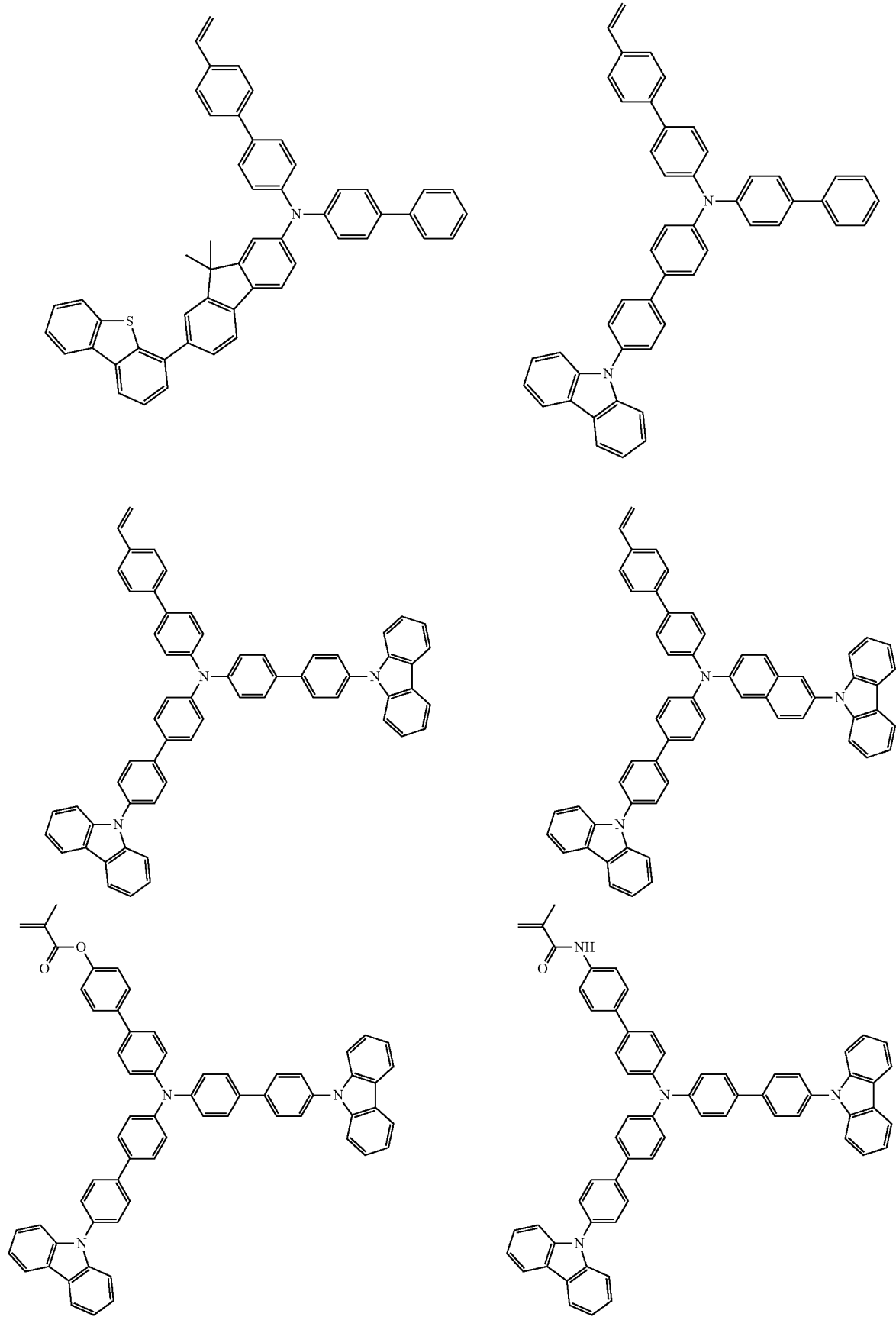

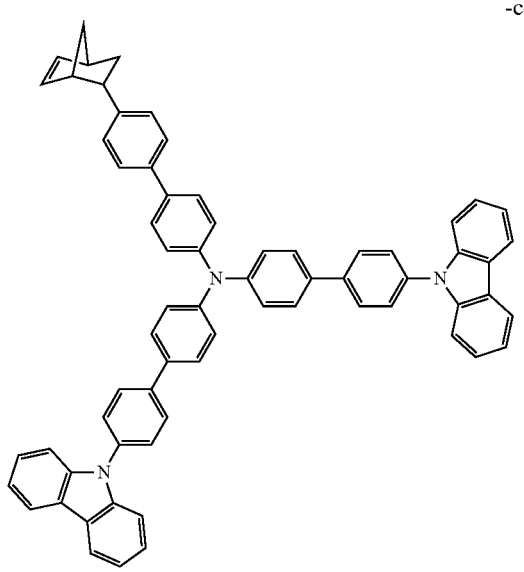
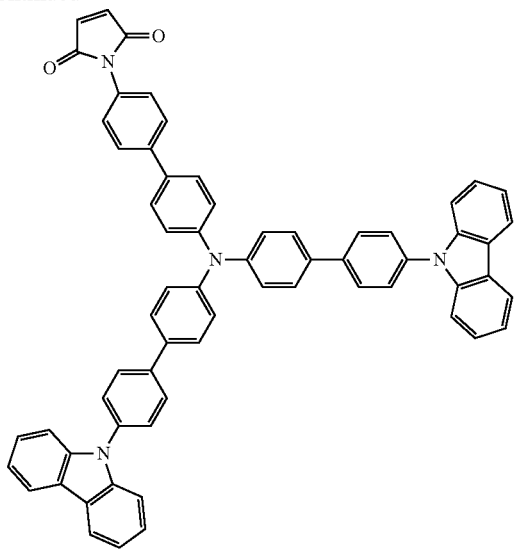
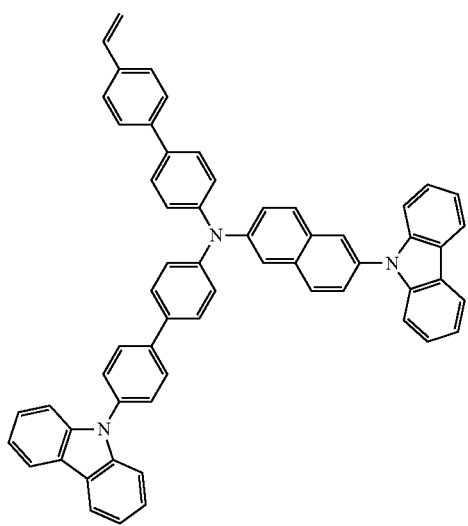
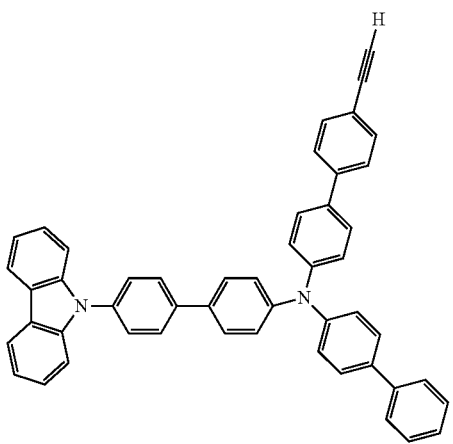
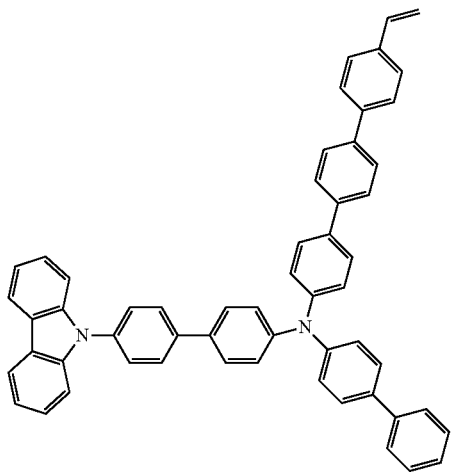
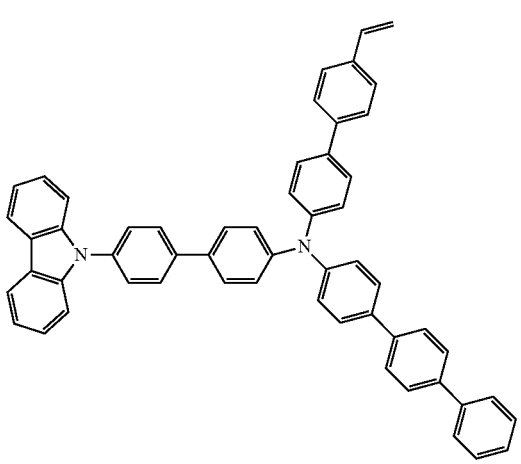

-continued
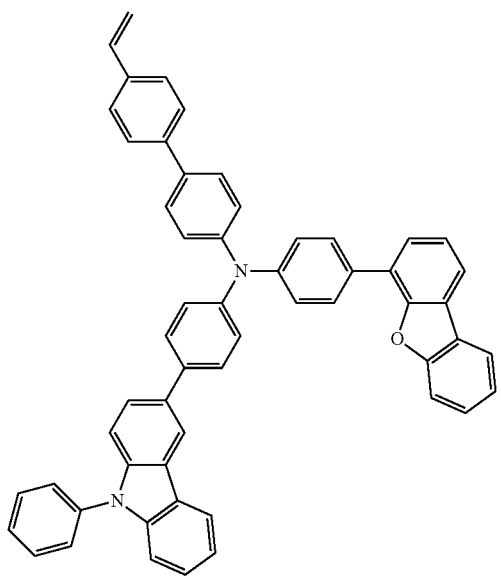 [SMILES: C=Cc1ccc(-c2ccc(N(c3ccc(-c4ccc5c(c4)c4ccccc4n5-c4ccccc4)cc3)c3ccc(-c4cccc5c4oc4ccccc45)cc3)cc2)cc1]
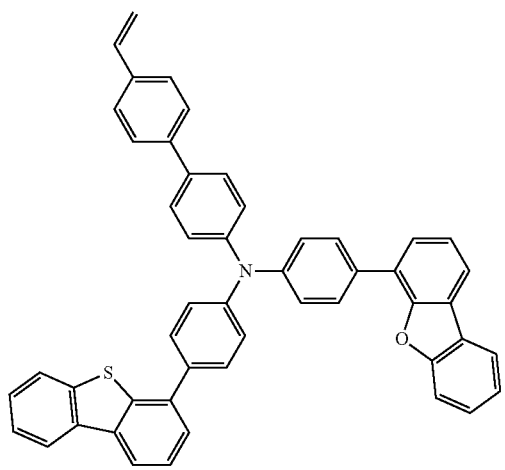 [SMILES: C=Cc1ccc(-c2ccc(N(c3ccc(-c4cccc5c4oc4ccccc45)cc3)c3ccc(-c4cccc5c4sc4ccccc45)cc3)cc2)cc1]
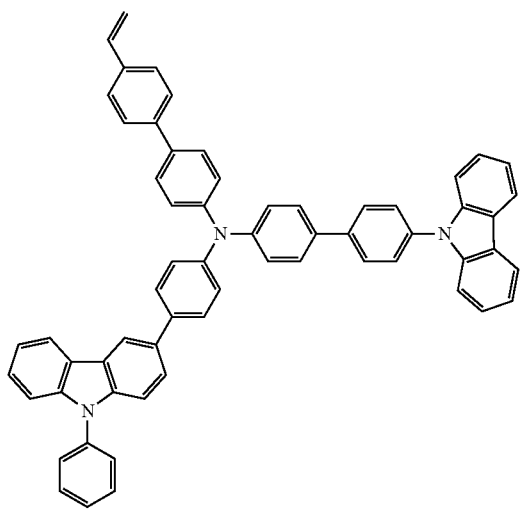
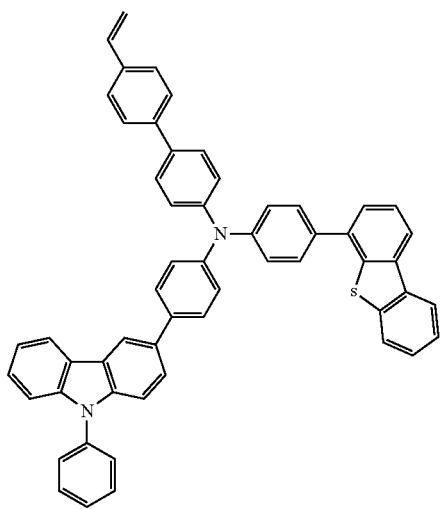
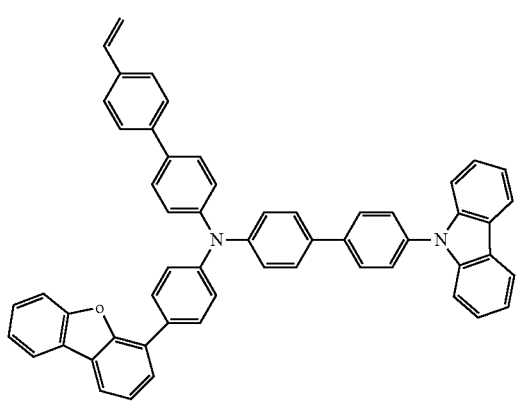
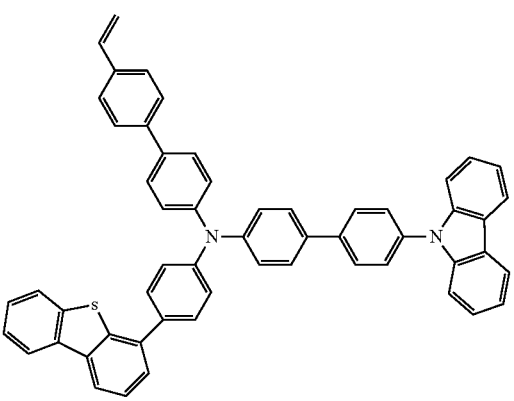

-continued
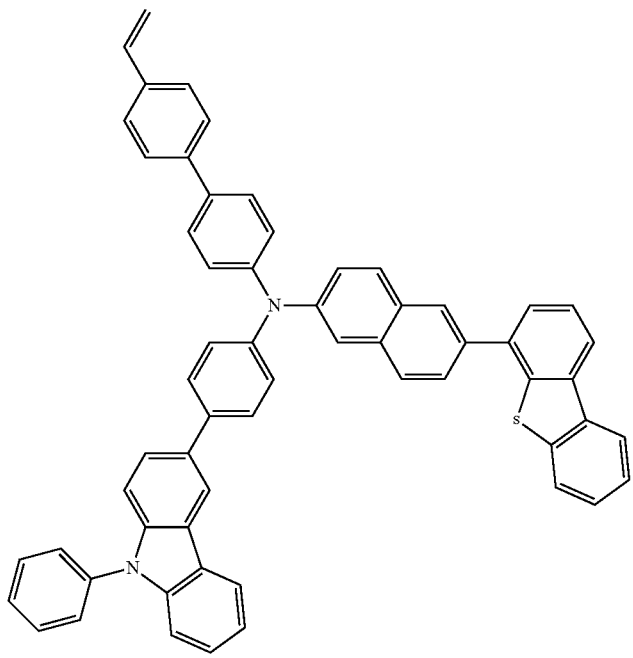
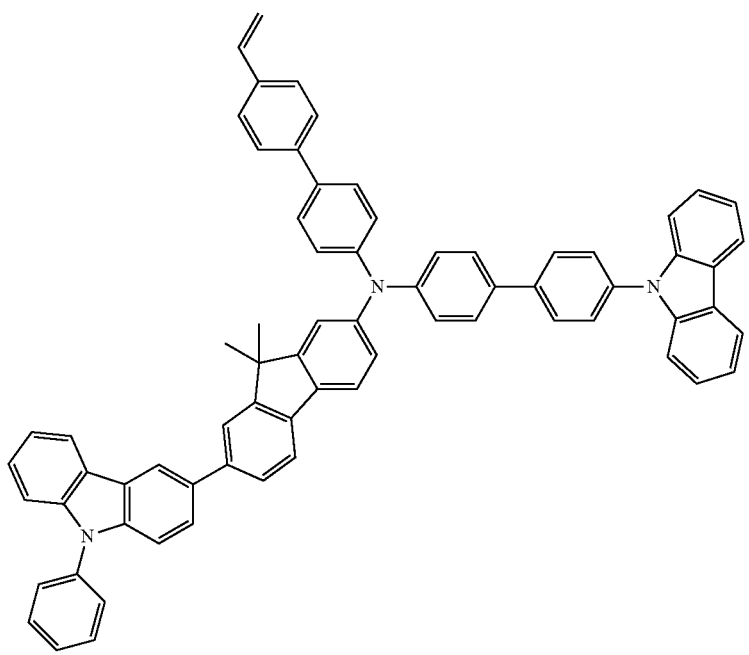

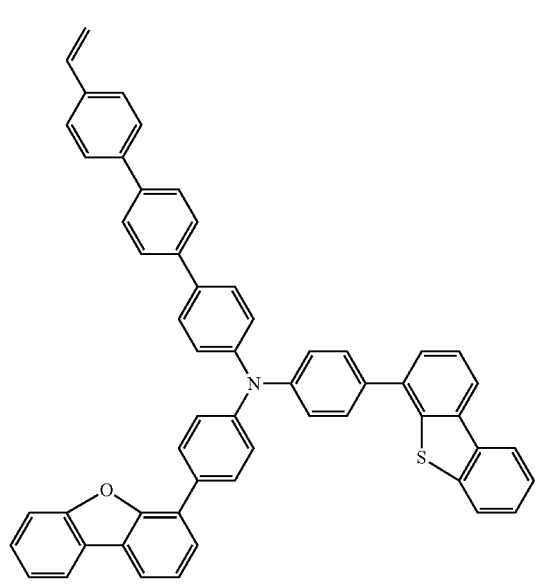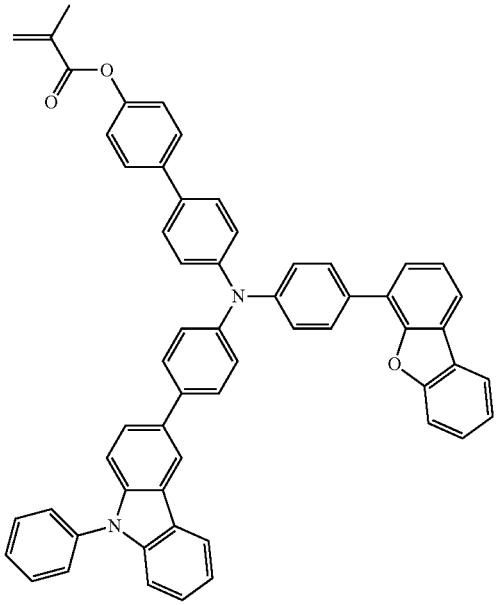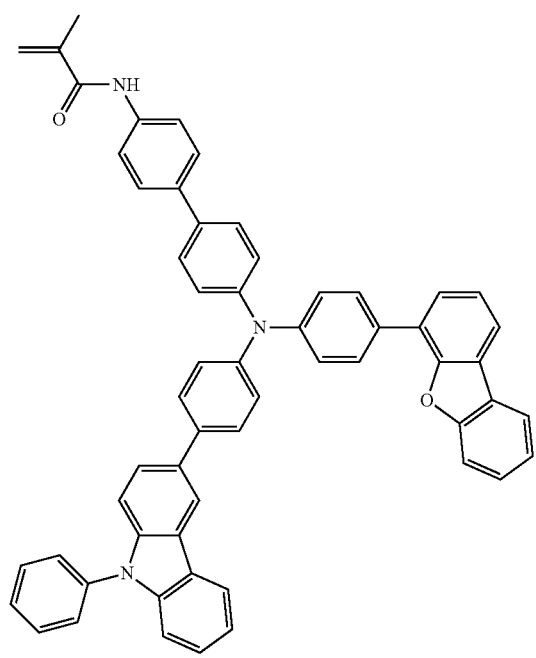

-continued
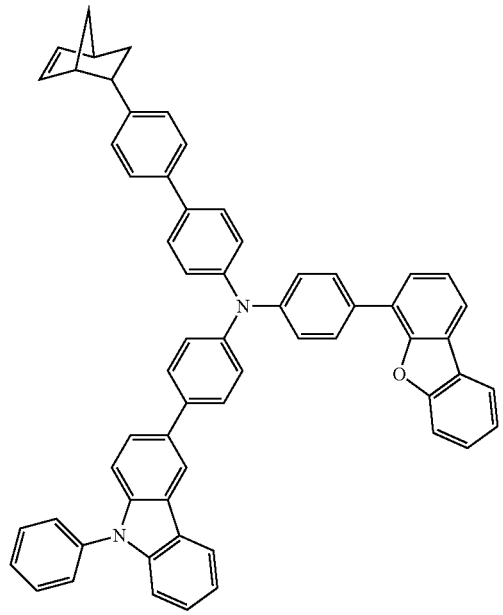
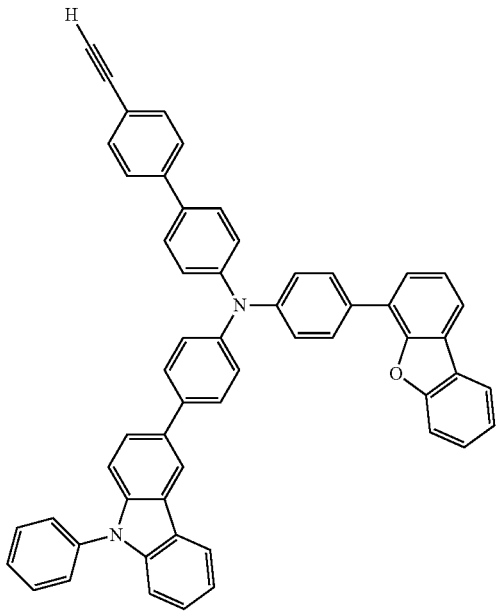
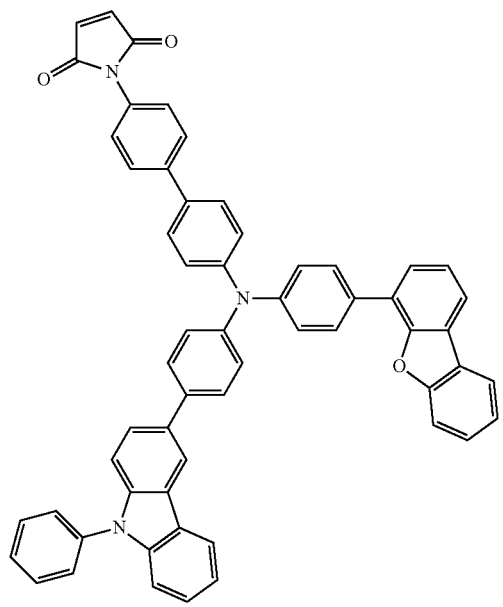
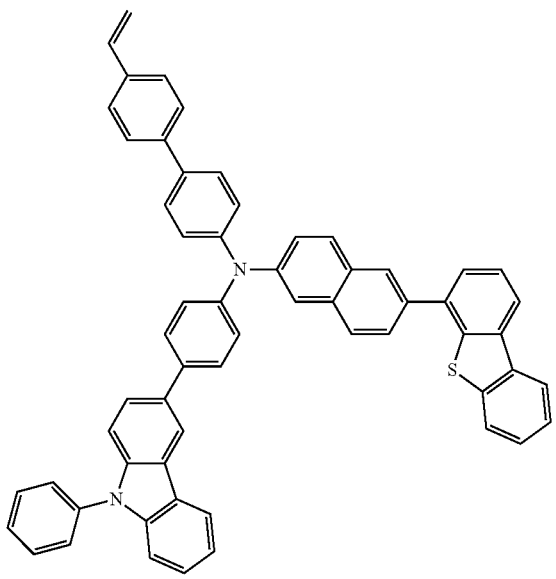

-continued
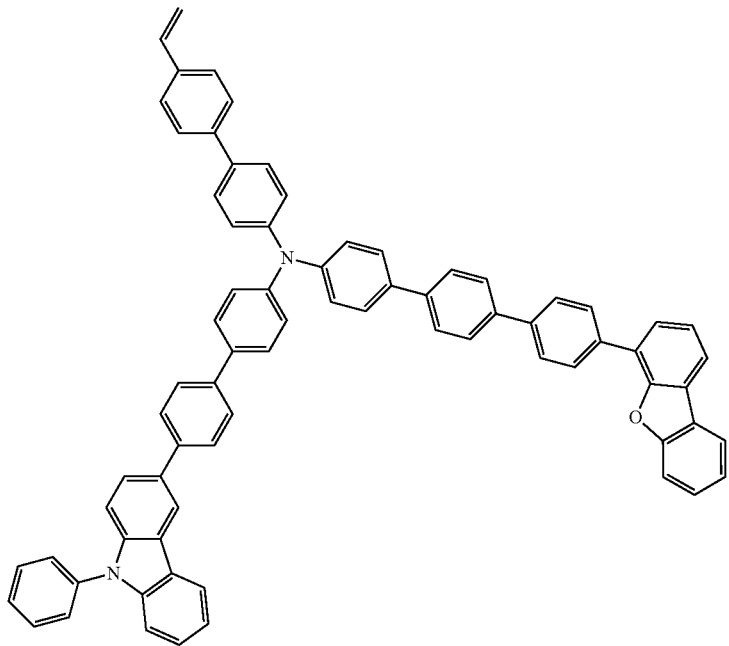
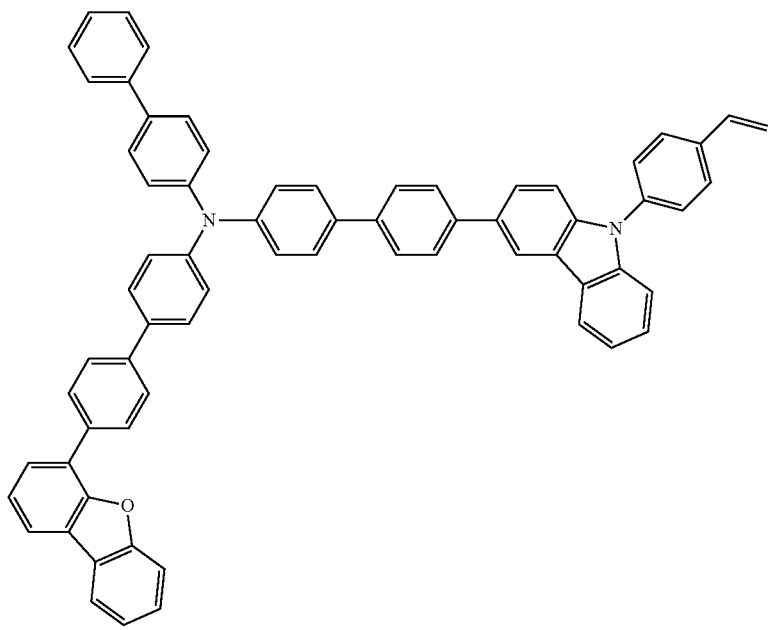

-continued
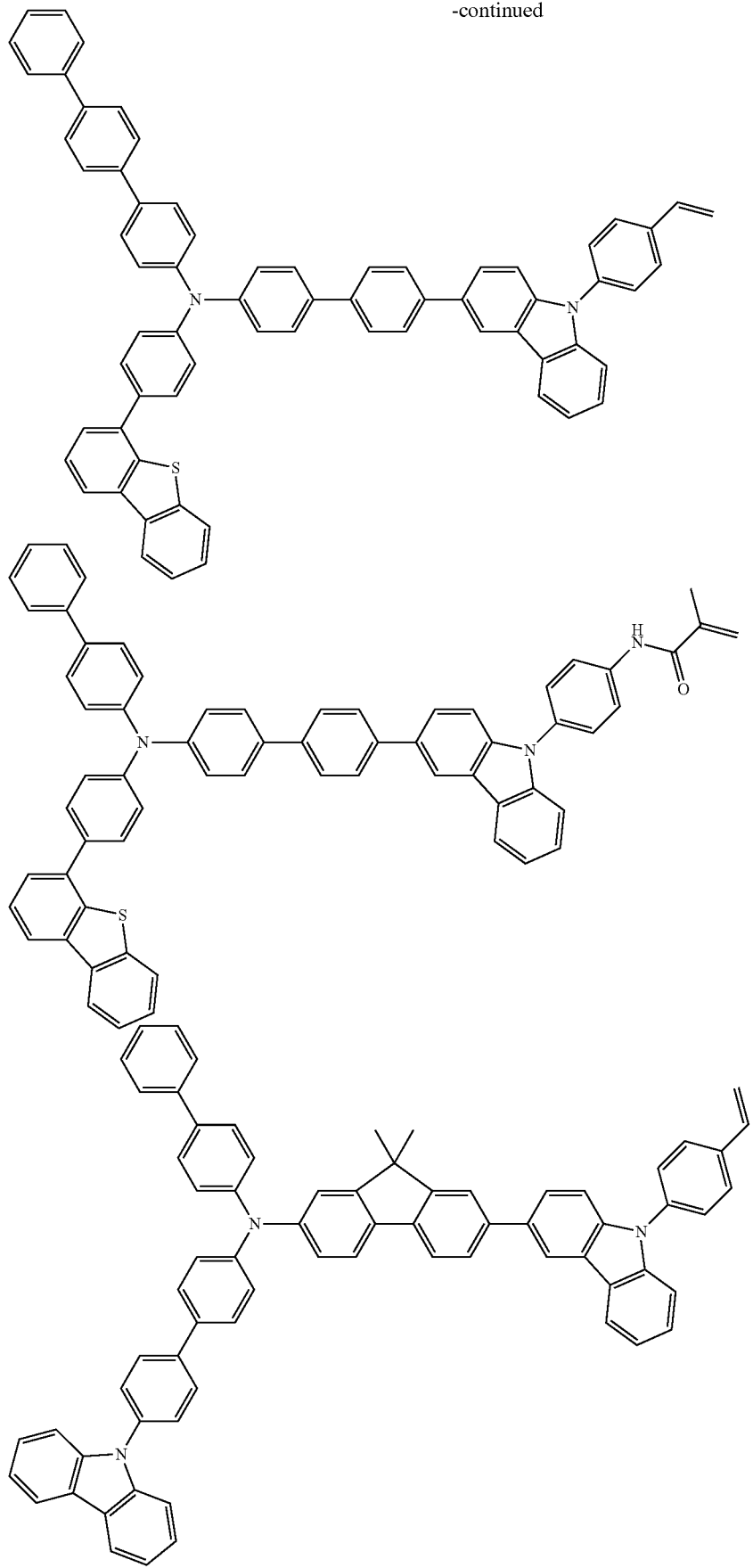

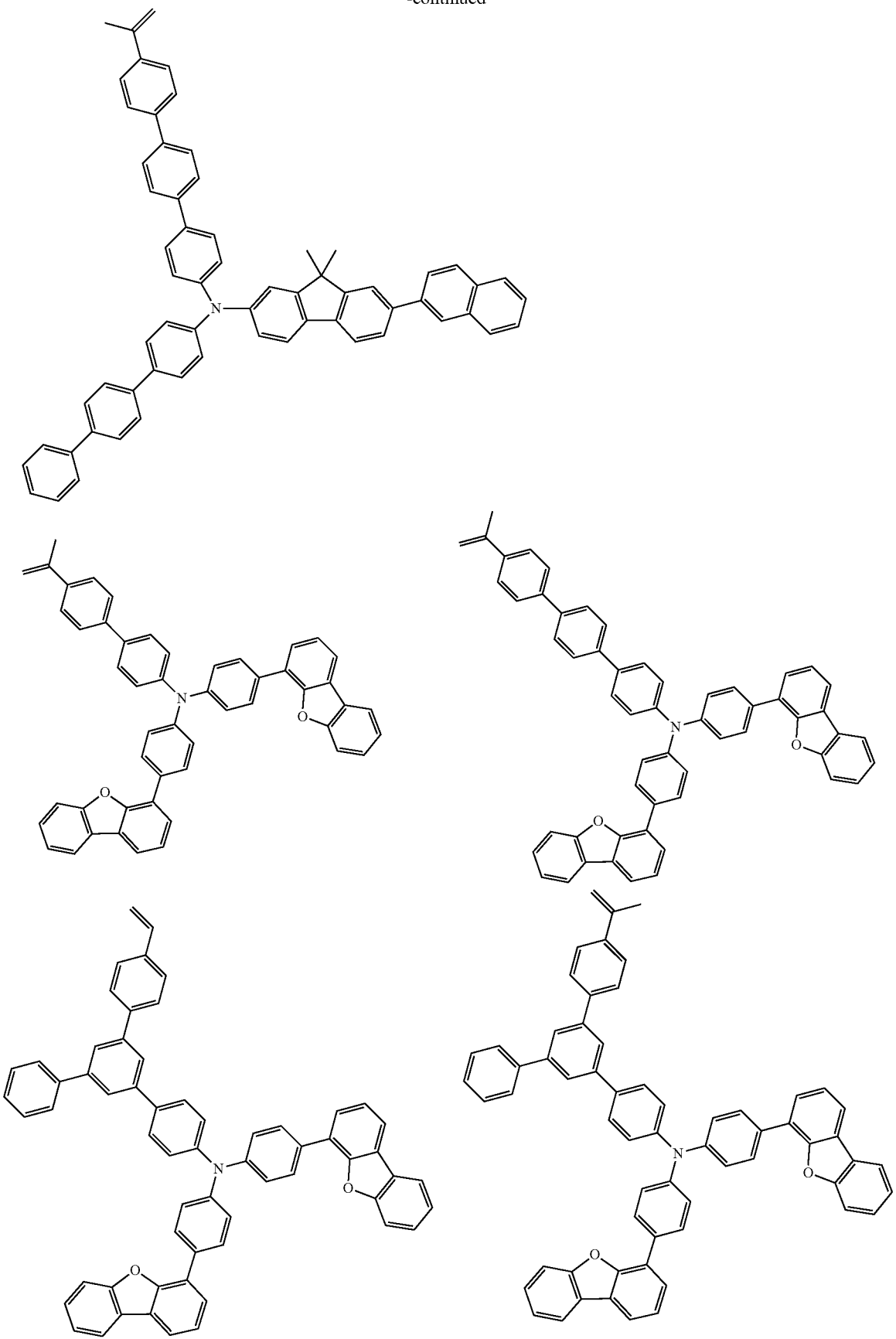

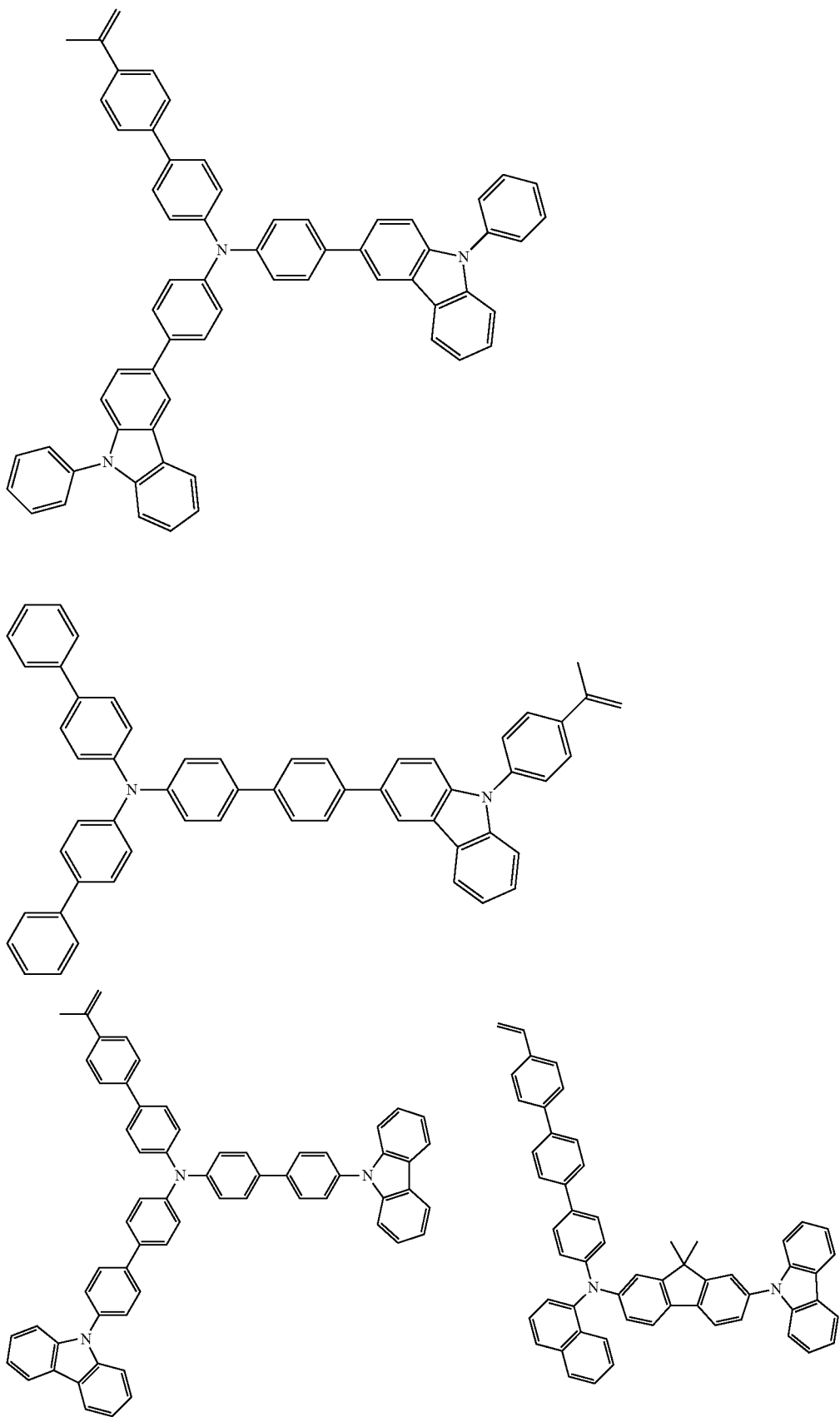

-continued
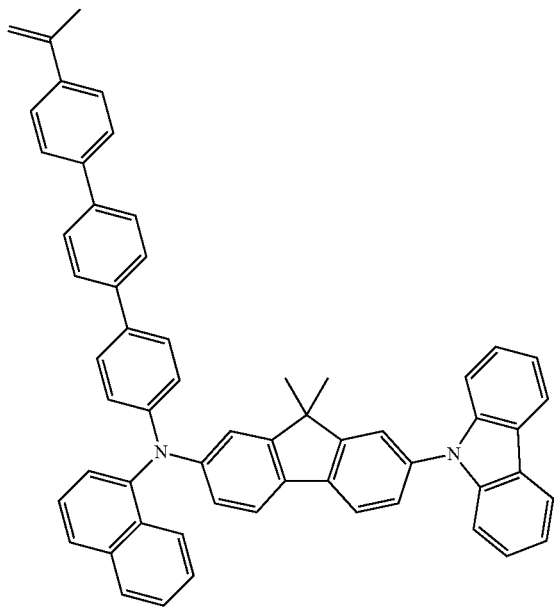
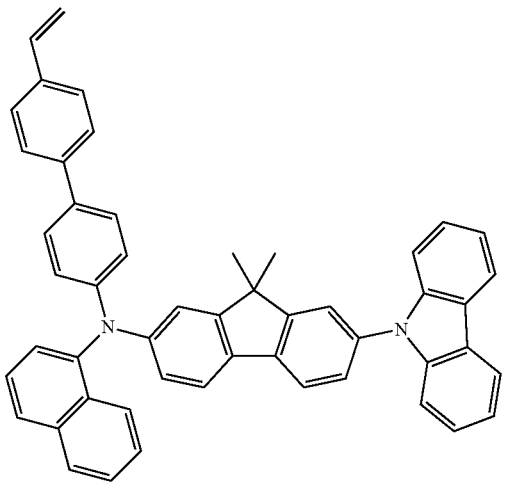
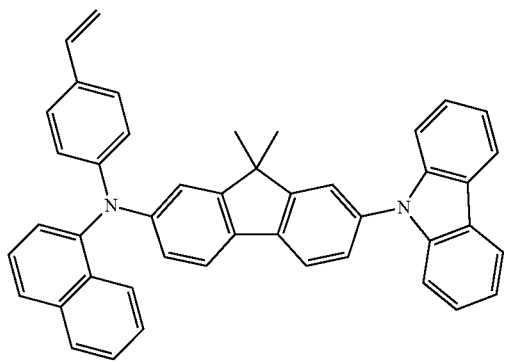
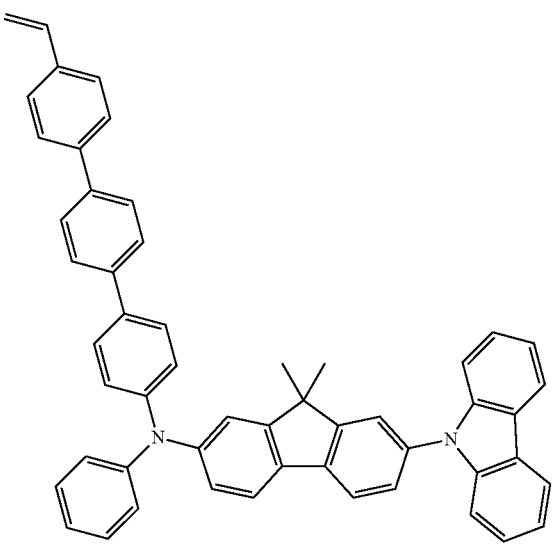
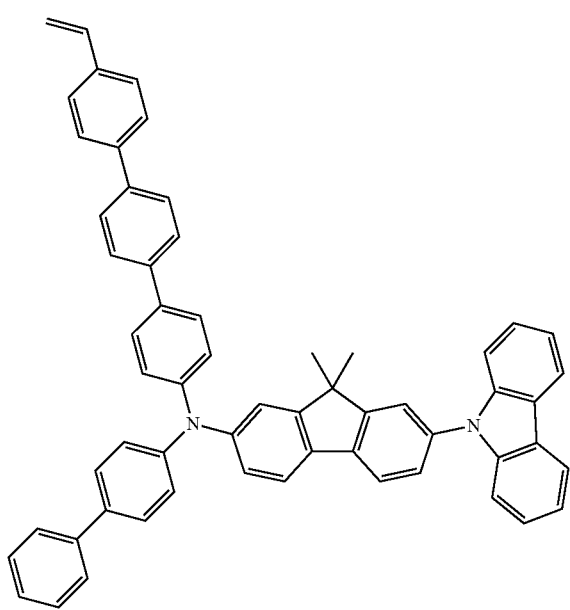
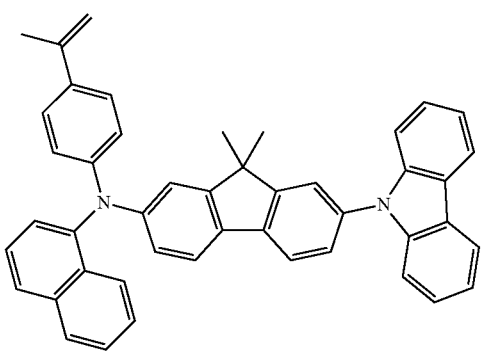

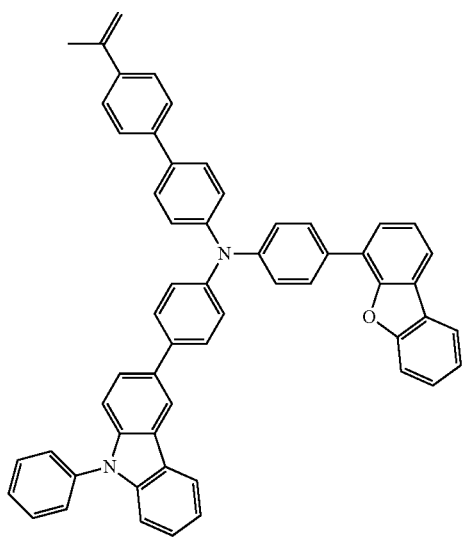
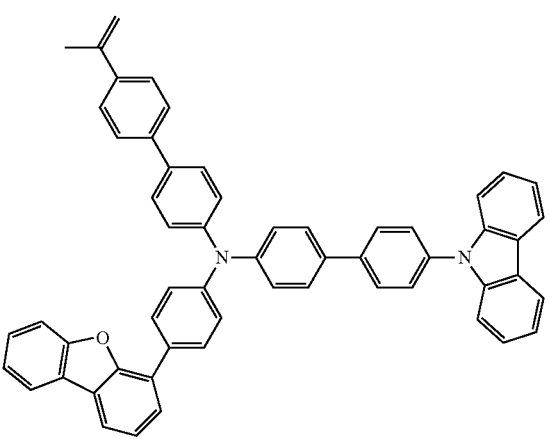
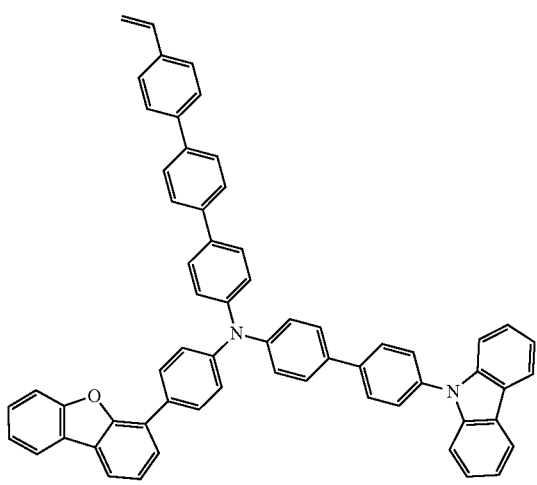
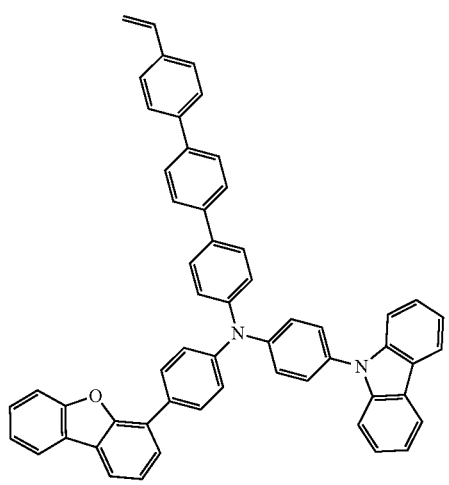
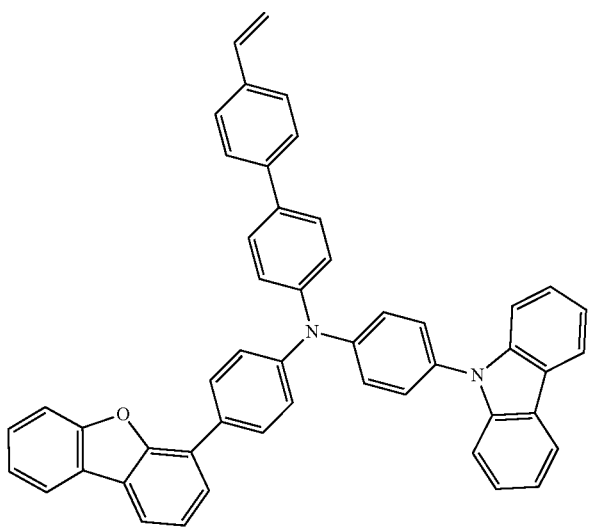

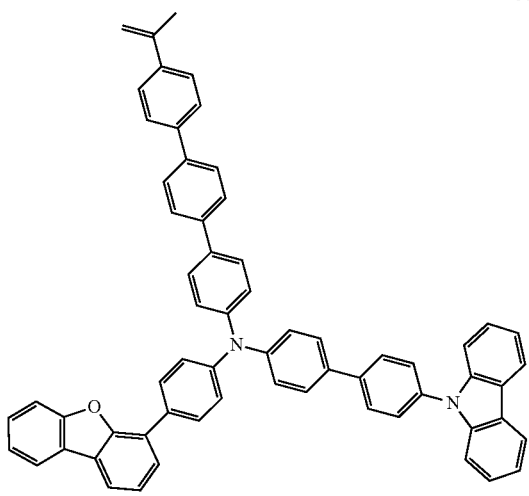
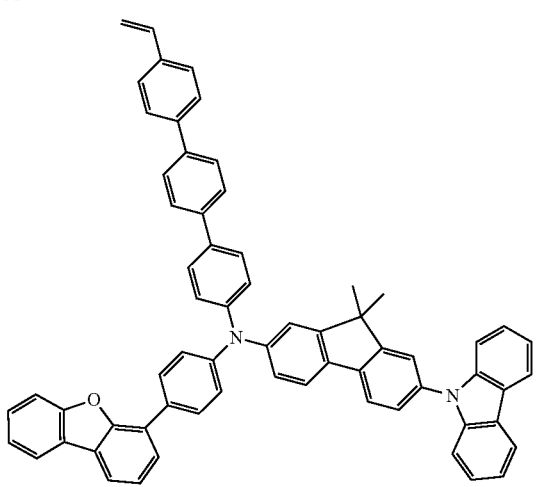
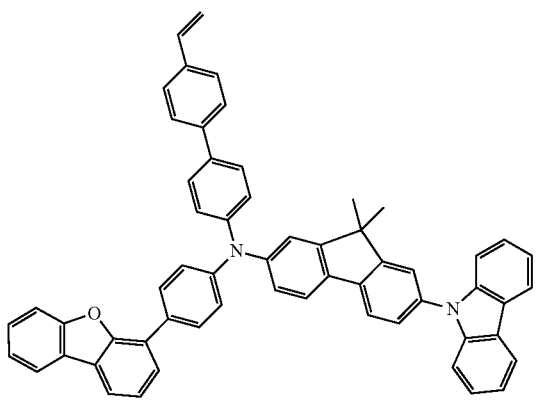
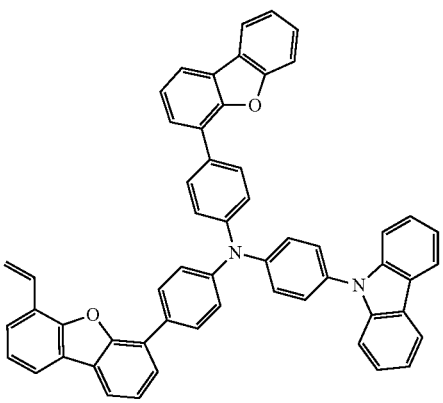
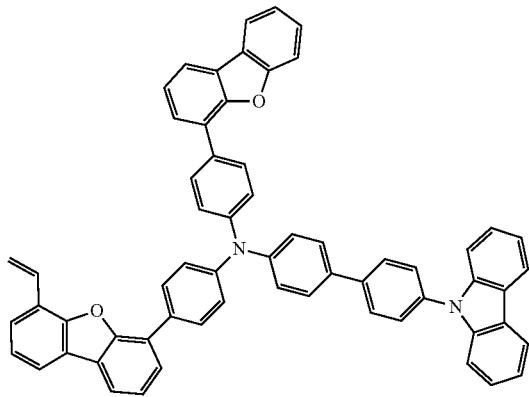
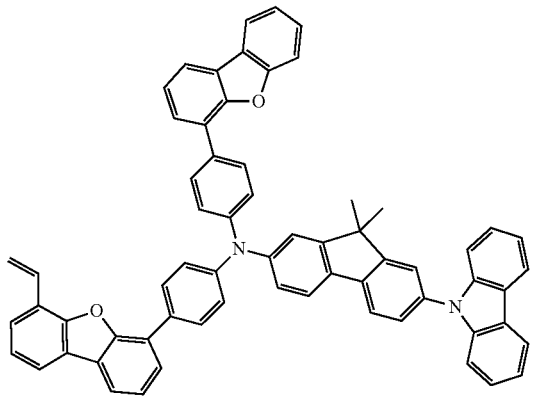

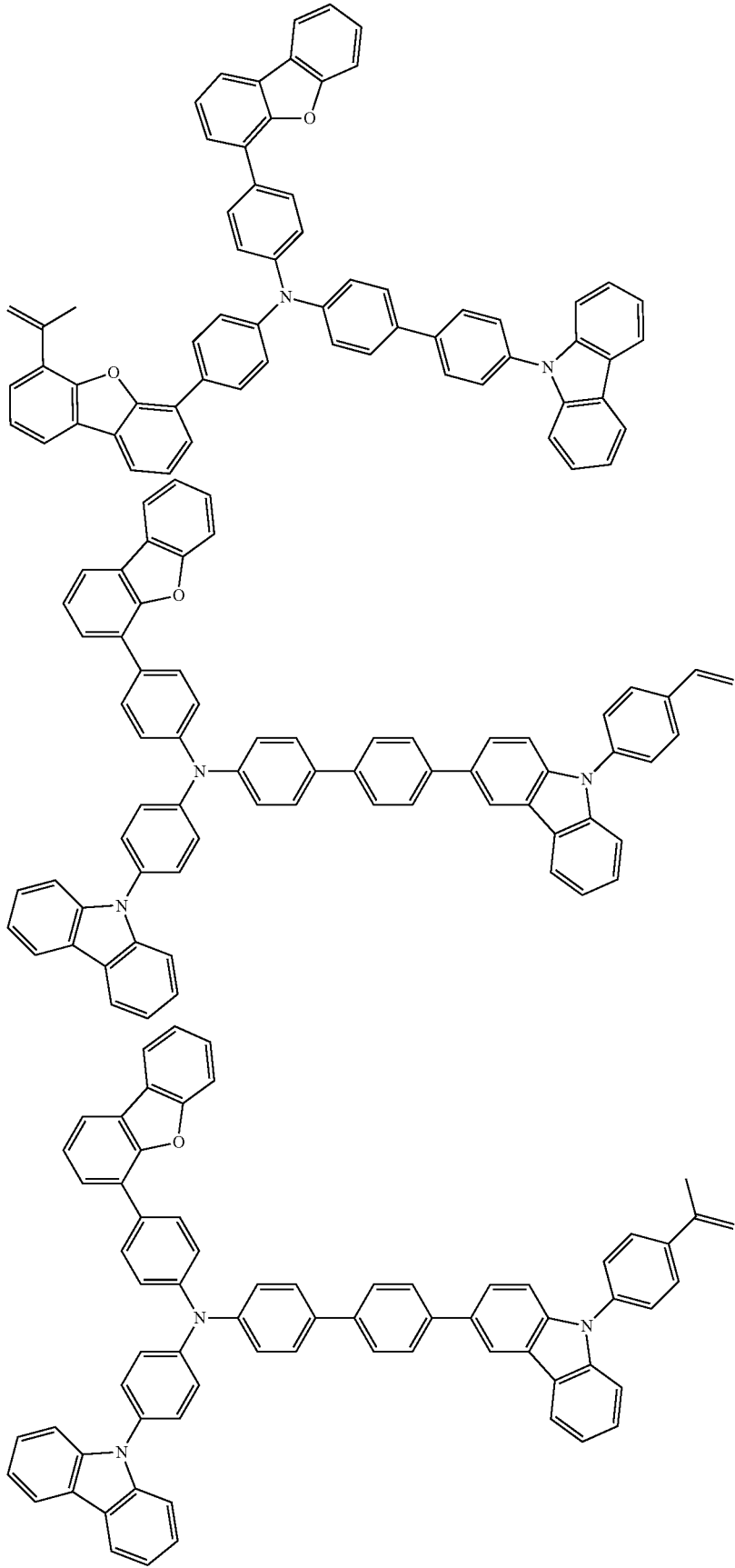

-continued
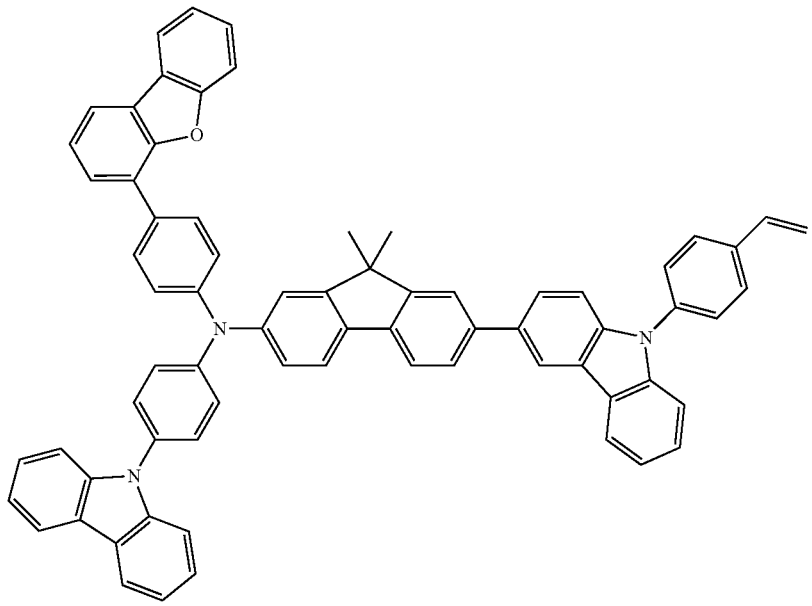
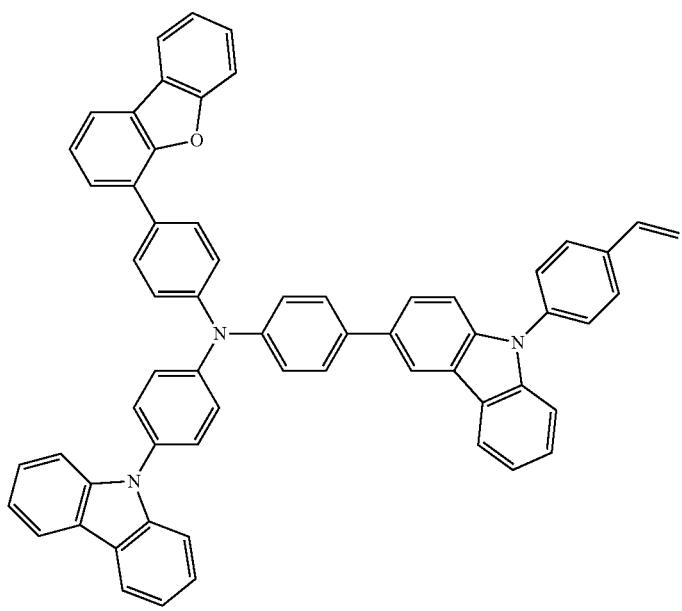

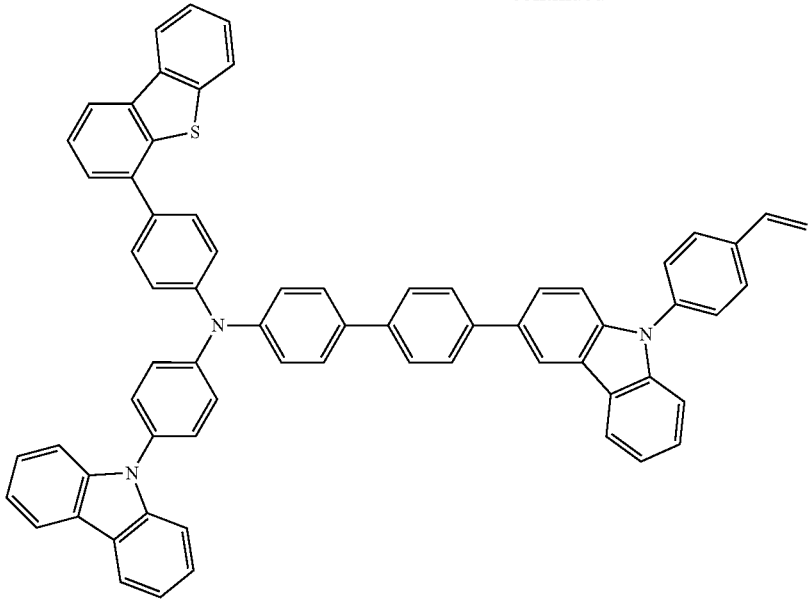

Embodiment 2

Polymer

A polymer having a repeating unit derived from one or two or more selected from the group consisting of the polymerizable monomers (I) to (III).

That is, the polymer of the invention comprises one of the followings:
(a) a homopolymer having a repeating unit derived from one monomer selected from the group consisting of the polymerizable monomers (I) to (III)
(b) a copolymer having a repeating unit derived from two or more monomers selected from the group consisting of the polymerizable monomers (I) to (III)
(c) a copolymer having a repeating unit derived from one or two ore more monomers selected from the group consisting of the polymerizable monomers (I) to (III) and a repeating unit derived from other monomers The copolymer (c) contains preferably 50 mol % or more, more preferably 70 mol % or more, of the monomer component of the polymerizable monomers (I) to (III). If the amount of the polymerizable monomer component of the invention is smaller than 50 mol %, advantageous effects brought about by the use of the polymerizable monomers (I) to (III) of the invention may not be fully exhibited.

No specific restrictions are imposed on the bonding manner of the copolymers (b) and (c), and they may be any of a random copolymer, an alternate copolymer, a block copolymer, a graft copolymer, a random block copolymer, a comb-like copolymer and a star-like copolymer. However, the polymer of the invention is more directed to a liner copolymer than a cross-linked or net-work polymer.

The copolymer (c) may be any of a random copolymer containing a repeating unit A (for example, the polymerizable monomers (I) to (III)) and a repeating unit B (other monomers) (-ABBABBBAAABA-), an alternate copolymer (-ABABABABABAB-), a block copolymer (-AAAAAABBBBBB-) and a graft copolymer (either the repeating unit A or the repeating unit B may be the main chain or the side chain).

As examples of other monomers of the copolymer (c), in particular, a polymerizable monomer in which a monoamine-, diamine- or triamine-based aromatic compound shown below is substituted by a group comprising a polymerizable functional group is preferable.

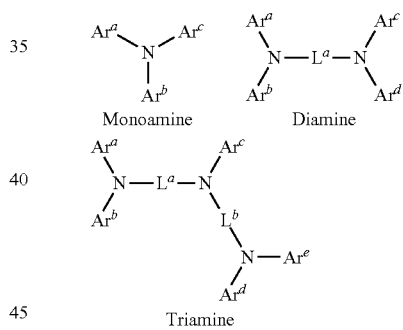

Monoamine    Diamine

Triamine

In the formula, $Ar^a$ to $Ar^e$ are independently a substituted or unsubstituted aryl group having 6 to 40 ring carbon atoms;

$L^a$ and $L^b$ are independently a substituted or unsubstituted arylene group having 6 to 40 ring carbon atoms.

Examples of the aryl group and the arylene group of $Ar^a$ to $Ar^e$ and $L^a$ and $L^b$ are the same as those mentioned above.

Substituents of $Ar^a$ to $Ar^e$ and $L^a$ and $L^b$ are independently one or more groups selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring atoms, a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 ring carbon atoms, an alkylarylamino group having 8 to 30 carbon atoms wherein the aryl part has 6 to 20 ring carbon atoms, a halogen atom, a nitro group, a cyano group and a hydroxyl group.

It is preferred that a terminal aromatic group of $Ar^a$ to $Ar^e$ in the above-mentioned amine-based aromatic compound be substituted by the group comprising a polymerizable functional group.

It is further preferred that the polymerizable functional group and the part other than the terminal aromatic group in the above formula be bonded to the terminal aromatic group at the para position (for example, if the terminal aromatic group is a phenylene group, at the $1^{st}$ and $4^{th}$ positions).

The reason therefor is as follows. Due to such bonding, interaction between side chains is suppressed to reduce the amount of an excimer or an exciplex generated. As a result, device performance such as hole-transporting properties of the polymer is improved, and the polymerization reaction ratio is improved to decrease the amount of monomers remaining unreacted, whereby durability and life of an organic device, in particular, an organic EL device, are improved.

By using such a copolymer (c), solubility of the resulting polymer in a coating solvent can be improved, whereby injection and transporting properties of holes can be improved.

No specific restrictions are imposed on the molecular weight of the polymer of the invention. The polymer of the invention includes polymers with various molecular weights ranging from an oligomer equals to or larger in size than a dimer to an ultra high molecular weight polymer. The polymer of the invention has a number average molecular weight (Mn) of preferably $10^3$ to $10^8$, more preferably $10^3$ to $10^6$. The weight average molecular weight (Mw) thereof is preferably $10^3$ to $10^8$, more preferably $10^3$ to $10^6$. Although there are no specific restrictions on the molecular weight distribution represented by Mw/Mn, an Mw/Mn of 10 or less is preferable, with 3 or less being further preferable. If the molecular weight is too large, gelation occurs to make formation of a homogeneous film impossible in the fabrication of a device. A too small molecular weight makes control of solubility difficult. The both molecular weights were obtained by using a size exclusion chromatography (SEC) and by calibrating with standard polystyrene.

In the blue-emitting organic electroluminescence device, although the reason is not clear, the blue-emitting organic electroluminescence device has an improved luminous efficiency, a prolonged life and improved thermal resistance when the polymer of the invention has a number average molecular weight (Mn) of $10^3$ to $5 \times 10^3$ or a weight average molecular weight (Mw) of $10^3$ to $5 \times 10^3$.

The polymer of the invention can be produced by subjecting a monomer to an addition polymerization, a cyclopolymerization or a ring-opening polymerization.

Although no specific restrictions are imposed on the polymerization method for the polymer of the invention, radical polymerization, ionic polymerization, living polymerization, radical living polymerization, coordination polymerization or the like can be used, for example. In particular, radical polymerization or cationic polymerization is preferable. As the initiator of radical polymerization, an azo compound and a peroxide can be mentioned, for example. Azobisisobutyronitrile (AIBN), an azobisisobutylic acid diester derivative and benzoyl peroxide (BPO) are preferable.

As the initiator of cationic polymerization, various strong acids (p-toluenesulfonic acid, trifluoromethanesulfonic acid, or the like) and lewis acid are preferable.

Although no specific restrictions are imposed on the polymerization solvent, an aromatic hydrocarbon solvent such as toluene and chlorobenzene, a halogenated hydrocarbon solvent such as methylene chloride, dichloromethane and chloroform, an ether solvent such as tetrahydrofuran and dioxane, an amide solvent such as dimethylformamide, an alcohol solvent such as methanol, an ester solvent such as ethyl acetate and a ketone solvent such as acetone, or the like can be given. By selecting a suitable solvent, it is possible to conduct solution polymerization in which polymerization is conducted in a homogeneous system and precipitation polymerization in which a generated polymer is precipitated.

These organic solvents may be used either singly or in combination of two or more. It is preferred that the organic solvent be used in an amount such that the concentration of the monomer be 0.1 to 90% by weight, more preferably 1 to 50% by weight.

The polymerization temperature is not particularly restricted insofar as a reaction medium keeps the liquid state. The polymerization temperature is preferably –100 to 200° C., with 0 to 120° C. being more preferable. The reaction time varies depending on reaction conditions such as the reaction temperature, but one hour or longer is preferable, with 2 to 500 hours being more preferable.

As for the polymerization product, according to a known method, a reaction solution is added to a lower alcohol such as methanol to allow precipitation, and precipitates thus deposited are filtered out and dried, whereby an intended polymer can be obtained, for example. If the purity of the polymer is low, purification may be conducted by a normal method such as re-precipitation, Soxhlet continuous extraction and column chromatography.

By conducting purification in this way, an unreacted monomer and impurities such as a polymerization catalyst are removed, whereby durability and life of an organic device, in particular, an organic EL device, are improved.

Embodiment 3

Material Comprising the Polymer

The polymer obtained by the above-mentioned method can be suitably used as a material for the following organic devices, a hole-injecting and transporting material and a material for an organic electroluminescence device. The polymer enables an organic device obtained, in particular, an organic EL device, to have improved device properties such as life and luminous efficiency. In addition, even when a device is subjected to high-temperature driving which is practical in applications of a display or illumination, the display suffers only a slight degree of deterioration, whereby an organic EL device suited to practical use can be provided.

Further, since a homogeneous hole-injecting/transporting layer can be formed by the coating method, a material comprising the polymer of the invention is suited for a reduction in cost or an increase in screen size in applications of a display or illumination.

Examples of the organic device include, in addition to an organic EL device, an organic TFT, a photoelectric conversion device such as organic solar cell and an image sensor.

Examples of the organic EL device include a planar emitting body such as a flat panel display of a wall-hanging television, general or special illumination devices, backlight of a copier, a printer, or a liquid crystal display, light sources for instruments, a display panel and a navigation light.

The polymer of the invention can also be used as an electrophotographic photoreceptor.

Embodiment 4

Organic Electroluminescence Device

The organic electroluminescence device of the invention (hereinafter often referred to as the organic EL device) comprises one or a plurality of organic thin film layers comprising an emitting layer between a cathode and an anode wherein at least one layer of the organic thin film layers comprises the polymer of the invention.

In the organic EL device of the invention, it is preferred that the organic thin film layers comprise one or both of a hole-transporting layer and a hole-injecting layer, and that one or both of the hole-transporting layer and the hole-injecting layer comprise the polymer of the invention.

Further, it is more preferred that the polymer of the invention be contained as the main component of one or both of the hole-transporting layer and the hole-injecting layer.

In the organic EL device of the invention, it is preferred that the emitting layer contain one or both of a styrylamine compound and an arylamine compound.

If one or both of the hole-transporting layer and the hole-injecting layer is included, it is preferred that an acceptor material be contained in one or both of the hole-injecting layer and the hole-transporting layer. It is particularly preferred that an acceptor material be contained in a layer which is adjacent to an anode.

By allowing an acceptor material to be contained, density of holes in the hole-injecting/transporting layer can be increased or hole transportability can be improved. As a result, the resulting organic EL device has a lowered driving voltage and a prolonged life due to improved carrier balance.

An acceptor material is preferably an organic compound which has an electron-attracting substituent or an electron deficient ring.

As the electron-attracting substituent, a halogen, CN—, a carbonyl group, an aryl boron group or the like can be given, for example.

Examples of the electron-deficient ring include, though not limited thereto, a compound selected from the group consisting of 2-pyridyl, 3-pyridyl, 4-pyridyl, 2-quinolyl, 3-quinolyl, 4-quinolyl, 2-imidazole, 4-imidazole, 3-pyrazole, 4-pyrazole, pyridazine, pyrimidine, pyrazine, cinnoline, phthalazine, quinazoline, quinoxaline, 3-(1,2,4-N)-triazolyl, 5-(1,2,4-N)-triazolyl, 5-tetrazolyl, 4-(1-O,3-N)-oxazole, 5-(1-O,3-N)-oxazole, 4-(1-S,3-N)-thiazole, 5-(1-S,3-N)-thiazole, 2-benzoxazole, 2-benzothiazole, 4-(1,2,3-N)-benzotriazole, and benzimidazole.

It is preferred that the above-mentioned acceptor be a quinoid derivative.

Compounds represented by the following formulas (1a) to (1i) can be given as a quinoid derivative. It is more preferred that the quinoid derivative be a compound represented by the formulas (1a) and (1b):

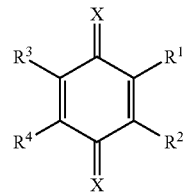
(1a)

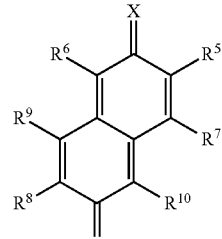
(1b)

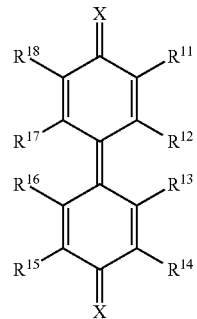
(1c)

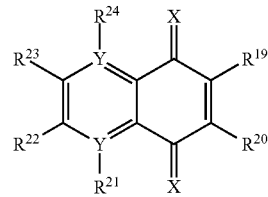
(1d)

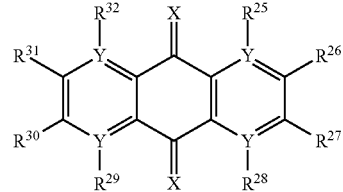
(1e)

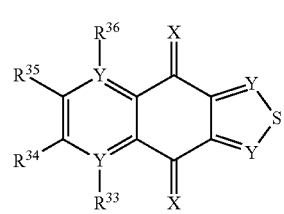
(1f)

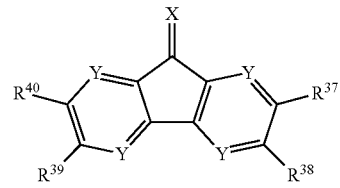
(1g)

-continued

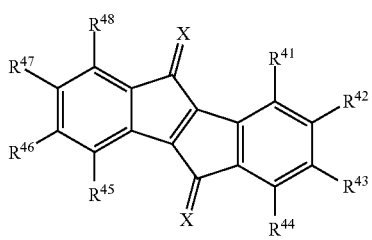
(1h)

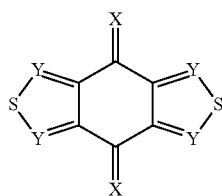
(1i)

In the formulas (1a) to (1i), $R^1$ to $R^{48}$ are independently a hydrogen atom, a halogen atom, a fluoroalkyl group, a cyano group, an alkoxy group, an alkyl group or an aryl group, with hydrogen and a cyano group being preferable.

In the formulas (1a) to (1i), X is an electron-attracting group which is formed of one of the following structures (j) to (p). The structures (j), (k) and (l) are preferable.

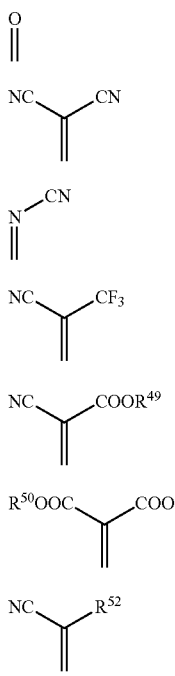

(j)
(k)
(l)
(m)
(n)
(o)
(p)

In the formula, $R^{49}$ to $R^{52}$ are independently hydrogen, a fluoroalkyl group, an alkyl group, an aryl group or a heterocyclic group. $R^{50}$ and $R^{51}$ may be bonded to form a ring.

In the formulas (1a) to (1i), Y is —N= or —CH=.

As the halogen represented by $R^1$ to $R^{48}$, fluorine and chlorine are preferable.

As the fluoroalkyl group represented by $R^1$ to $R^{48}$, a trifluoromethyl group and a pentafluoroethyl group are preferable.

As the alkoxyl group represented by $R^1$ to $R^{48}$, a methoxy group, an ethoxy group, an iso-propoxy group, and a tert-butoxy group are preferable.

As the alkyl group represented by $R^1$ to $R^{48}$, a methyl group, an ethyl group, a propyl group, an iso-propyl group, a tert-butyl group and a cyclohexyl group are preferable.

As the aryl group represented by $R^1$ to $R^{48}$, a phenyl group and a naphthyl group are preferable.

Examples of the fluoroalkyl group, the alkyl group and the aryl group represented by $R^{49}$ to $R^{52}$ are the same those represented by $R^1$ to $R^{48}$.

The heterocyclic ring represented by $R^{49}$ to $R^{52}$ is preferably a substituent represented by the following formulas:

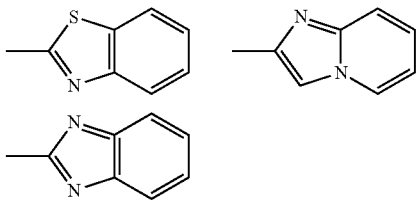

If $R^{50}$ and $R^{51}$ form a ring, X is preferably a substituent represented by the following formula:

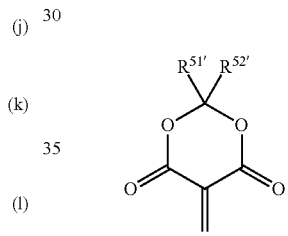

In the formula, $R^{51'}$ and $R^{52'}$ are independently a methyl group, an ethyl group, a propyl group and a tert-butyl group.

Specific examples of the quinoid derivative include the following compounds:

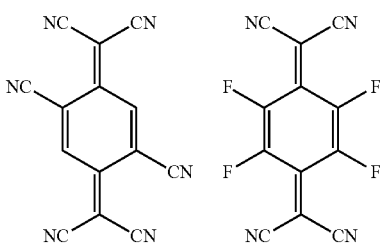

(CN)$_2$—TCNQ

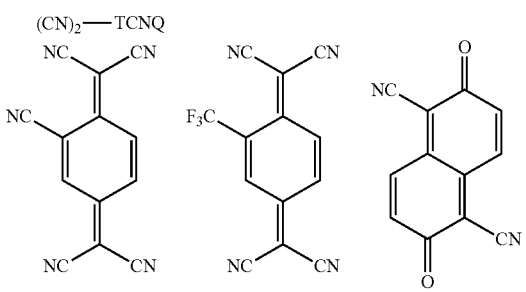

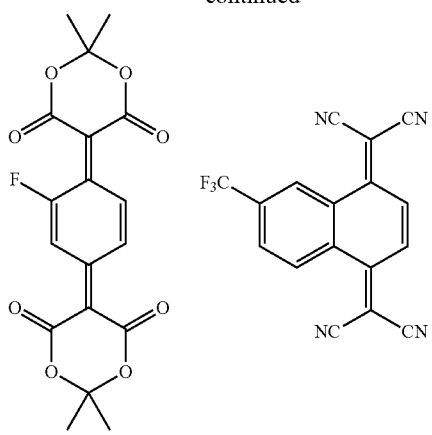
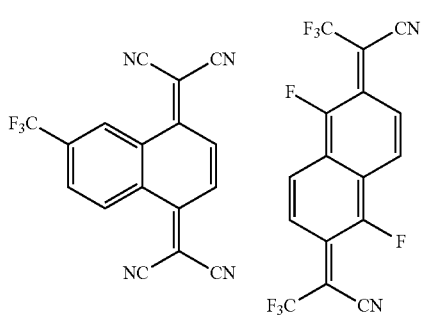
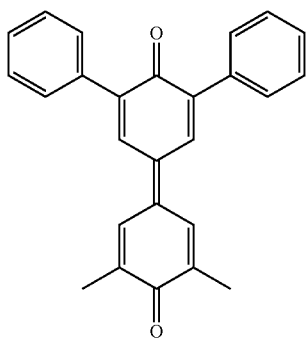
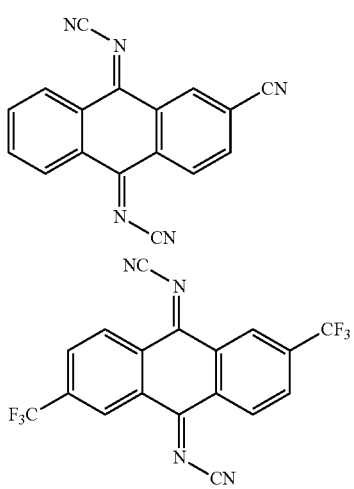
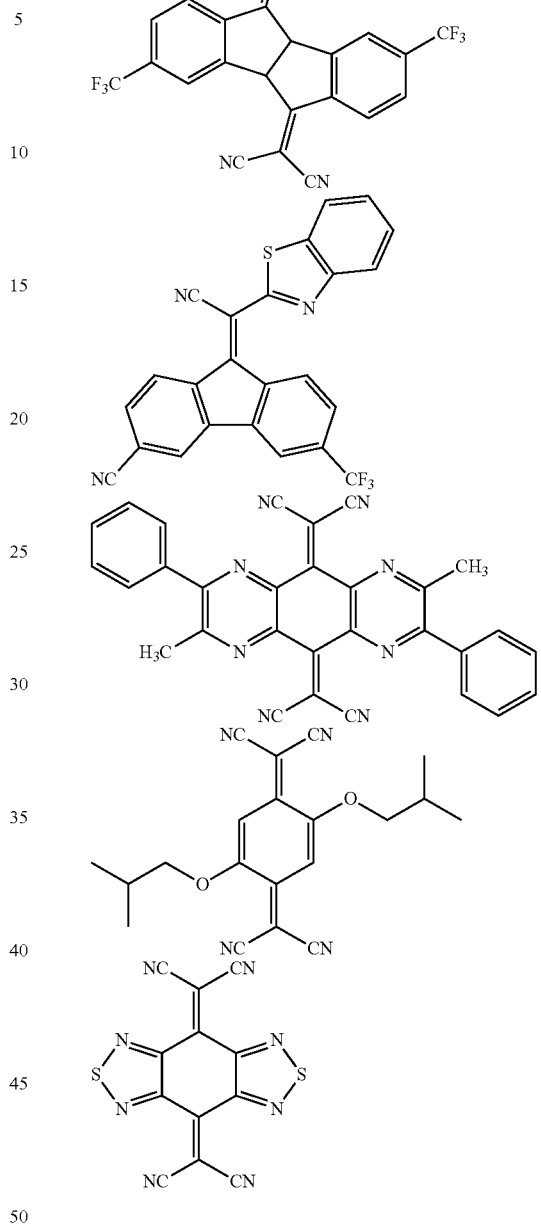

The content of an acceptor contained in the acceptor-containing layer is preferably 1 to 100 mol % relative to the entire layer, more preferably 50 to 100 mol %.

Further, the hole-injecting/transporting layer may contain fullerene. As examples of fullerene, a carbon cluster compound represented by C60 can be given. C70, C76, C78, C82, C84, C90, C96 or the like other than C60 may also be mentioned.

It is preferred that the organic EL device of the invention emit blue light. An organic EL device which emits blue light generally has a shorter device life. However, by using the polymer of the invention in the organic thin film layers, life of the device is hardly shortened even if it is subjected to practical high-luminance and high-temperature driving.

The representative device structures of the organic EL device of the invention are given below.

(1) Anode/emitting layer/cathode
(2) Anode/hole-injecting layer/emitting layer/cathode
(3) Anode/emitting layer/electron-injecting layer/cathode
(4) Anode/hole-injecting layer/emitting layer/electron-injecting layer/cathode
(5) Anode/organic semiconductor layer/emitting layer/cathode
(6) Anode/organic semiconductor layer/electron blocking layer/emitting layer/cathode
(7) Anode/organic semiconductor layer/emitting layer/adhesion-improving layer/cathode
(8) Anode/hole-injecting layer/hole-transporting layer/emitting layer/electron-injecting layer/cathode
(9) Anode/insulating layer/emitting layer/insulating layer/cathode
(10) Anode/inorganic semiconductor layer/insulating layer/emitting layer/insulating layer/cathode
(11) Anode/organic semiconductor layer/insulating layer/emitting layer/insulating layer/cathode
(12) Anode/insulating layer/hole-injecting layer/hole-transporting layer/emitting layer/insulating layer/cathode
(13) Anode/insulating layer/hole-injecting layer/hole-transporting layer/emitting layer/electron-injecting layer/cathode Of these, normally, the structure (8) is preferably used. The device structure is, however, not limited to those mentioned above.

<Transparent Substrate>

The organic EL device of the invention is fabricated by stacking on a transparent substrate a plurality of layers having the layer structures as mentioned above. The transparent substrate as referred to herein is a substrate for supporting the organic EL device, and is preferably a flat and smooth substrate having a 400-to-700-nm-visible-light transmittance of 50% or more.

Specific examples thereof include glass plates and polymer plates. Examples of the glass plate, in particular, include soda-lime glass, barium/strontium-containing glass, lead glass, aluminosilicate glass, borosilicate glass, barium borosilicate glass and quartz. Examples of the polymer plate include polycarbonate, acrylic polymer, polyethylene terephthalate, polyethersulfone and polysulfone.

<Anode>

As the conductive material used for the anode of the organic EL device of the invention, one having a work function larger than 4 eV is suitable, and carbon, aluminum, vanadium, iron, cobalt, nickel, tungsten, silver, gold, platinum and palladium, alloys thereof, oxidized metals such as tin oxide and indium oxide which are used for an ITO substrate and a NESA substrate and an organic conductive resin such as a polythiophene and polypyrrole are used.

<Cathode>

As the conductive material used for the cathode, one having a work function smaller than 4 eV is suitable, and magnesium, calcium, tin, lead, titanium, yttrium, lithium, ruthenium, manganese, aluminum, lithium fluoride and alloys thereof are used, but usable materials are not limited thereto. Representative examples of the alloy include, though not limited thereto, a magnesium/silver alloy, a magnesium/indium alloy and a lithium/aluminum alloy. The amount ratio of an alloy is controlled by the temperature of the deposition source, atmosphere, vacuum degree or the like, and a suitable ratio is selected. If necessary, the anode and the cathode each may be formed of two or more layers.

This cathode can be formed by making the electrode substances into a thin film by vapor deposition, sputtering or some other methods.

In the case where light is emitted from the emitting layer through the cathode, the cathode preferably has a light transmittance of larger than 10%.

The sheet resistance of the cathode is preferably several hundreds $\Omega/\square$ or less, and the film thickness thereof is usually from 10 nm to 1 μm, preferably from 50 to 200 nm.

<Insulating Layer>

In the organic EL device, pixel defects based on leakage or a short circuit are easily generated since an electric field is applied to a super thin film. In order to prevent this, it is preferable to insert an insulative thin layer between the pair of electrodes.

Examples of the material used in the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide and vanadium oxide. A mixture or a laminate of these materials may also be used.

<Emitting Layer>

The emitting layer of the organic EL device has the following functions (1), (2) and (3) in combination.

(1) Injection function: function of allowing injection of holes from the anode or hole-injecting layer and injection of electrons from the cathode or electron-injecting layer upon application of an electric field (2) Transporting function: function of moving injected carriers (electrons and holes) due to the force of an electric field (3) Emitting function: function of allowing electrons and holes to recombine to emit light Note that electrons and holes may be injected into the emitting layer with different degrees, or the transportation capabilities indicated by the mobility of holes and electrons may differ. It is preferable that the emitting layer move either electrons or holes.

The polymer of the invention may be used in the plurality of layers as mentioned above, if necessary. Further, an emitting material, a doping material, a hole-injecting material or an electron-injecting material which are known in the art can be used. It is also possible to use the polymer of the invention as the doping material. By allowing the organic thin film layers as mentioned above to be formed of a plurality of layers, the organic EL device can be prevented from a lowering of luminance or life by quenching. If necessary, an emitting material, a doping material, a hole-injecting material or an electron-injecting material may be used in combination. Further, by using a doping material, improvement in luminance or luminous efficiency can be attained, and red or blue emission can be obtained. Moreover, the hole-injecting layer, the emitting layer and the electron-injecting layer may respectively be formed of two or more layers. In this case, in the case of the hole-injecting layer, a layer which injects holes from the electrode is referred to as the hole-injecting layer and a layer which receives holes from the hole-injecting layer and transports the holes to the emitting layer is referred to as the hole-transporting layer. Similarly, in the case of the electron-injecting layer, a layer which injects electrons from the electrode is referred to as the electron-injecting layer and a layer which receives electrons from the electron-injecting layer and transports the electrons to the emitting layer is referred to as the electron-transporting layer. Each of these layers is selected and used according to the factors such as the energy level, heat resistance, adhesiveness to the organic layers or the metal electrode of the material.

Examples of the host material or the doping material which can be used in the emitting layer together with the polymer of the invention include, though not limited thereto, fused polymer aromatic compounds such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenenylanthracene, 9,10-bis(phenylethyl) anthracene and 1,4-bis(9'-ethynylanthracenyObenzene and derivatives thereof, organic metal complexes such as tris(8-quinolinolate)aluminum and bis-(2-methyl-8-quinolinolate)-4-(phenylphenolinate)aluminum, triarylamine derivatives, styrylamine derivatives, stilbene derivatives, coumarin derivatives, pyrane derivatives, oxazone derivatives, benzothiazole derivatives, benzoxazole derivatives, benzimidazole derivatives, pyrazine derivatives, cinnamate derivatives, diketo-pyrrolo-pyrrole derivatives, acrylidone derivatives, quinacrylidone derivatives and fluoranthene derivatives.

The hole-injecting/transporting layer is a layer which helps injection of holes to the emitting layer, and transports the holes to the emission range. It has a large hole mobility, and normally has a small ionization energy of 5.6 eV or less. As the material for such hole-injecting/transporting layer, a material which transports holes to the emitting layer at a lower electric field is preferable. Further, it is preferred that the mobility of holes be at least $10^{-4}$ cm$^2$/V·sec when applying an electric field of $10^4$ to $10^6$ V/cm.

As mentioned above, the polymer of the invention is particularly preferably used in the hole-injecting/transporting layer.

If the polymer of the invention is used in the hole-transporting region, the hole-injecting/transporting layer may be formed by using the hole-transporting material of the invention alone or in a mixture with other materials.

As the other material for forming the hole-injecting/transporting layer in a mixture with the polymer of the invention, any materials which have the above preferable properties can be used as without particular limitation. The material for forming the hole-injecting/transporting layer can be arbitrarily selected from materials which have been widely used as a material transporting carriers of holes in photoconductive materials and known materials used in a hole-injecting/transporting layer of organic EL devices. In the invention, a material which has a hole-transporting capability and can be used in the hole-transporting region is referred to as the hole-transporting material.

Specific examples of other materials than the polymer of the invention used in the hole-injecting/transporting layer include, though not limited thereto, a phthalocyanine derivative, a naphthalocyanine derivative, a porphyrin derivative, oxazole, oxadiazole, triazole, imidazole, imidazolone, imidazolethione, pyrazoline, pyrazolone, tetrahydroimidazole, oxazole, oxadiazole, hydrazone, acylhydrazone, polyarylalkane, stilbene, butadiene, benzidine-type triphenylamine, styrylamine-type triphenylamine, diamine-type triphenylamine, derivatives thereof, polymer materials such as polyvinyl carbazole, polysilane, conductive polymers (polyaniline and polythiophene) and a polymer of polymerizable monomers in which the above-mentioned monoamine-, diamine-, and triamine-based aromatic compounds are substituted by the group comprising a polymerizable functional group.

Of the hole-injecting materials which can be used in the organic EL device of the invention, a still further effective hole-injecting material is an aromatic tertiary amine derivative and a phthalocyanine derivative.

Examples of the aromatic tertiary amine derivatives include, though not limited thereto, triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cyclohexane or an oligomer or a polymer having these aromatic tertiary amine skeleton.

Examples of the phthalocyanine (Pc) derivative include, though not limited thereto, phthalocyanine derivatives and naphthalocyanine derivatives such as H$_2$Pc, CuPc, CoPc, NiPc, ZnPc, PdPc, FePc, MnPc, ClAlPc, ClGaPc, ClInPc, ClSnPc, Cl$_2$SiPc, (HO)AlPc, (HO)GaPc, VOPc, TiOPc, MoOPc and GaPc-O-GaPc. Further, it is preferred that the organic EL device of the invention comprise, between the emitting layer and the anode, a layer, a hole-transporting layer or a hole-injecting layer, for example, which contains the aromatic tertiary amine derivative and/or the phthalocyanine derivative as mentioned above.

Next, an explanation is made on the electron-injecting/transporting layer. The electron-injecting/transporting layer is a layer which helps injection of electrons to the emitting layer and transports the electrons to the emission region, and has a large electron mobility. The adhesion-improving layer is one of the electron-injecting layers which is formed of a material which has particularly good adhesion to the cathode.

Further, it is known that, in an organic EL device, since emitted light is reflected by an electrode (the cathode, in this case), light which is directly outcoupled from the anode interferes with light outcoupled after being reflected by the electrode. In order to utilize this interference effect efficiently, the film thickness of the electron-transporting layer is appropriately selected in a range of several nm to several µm. If the thickness is particularly large, in order to avoid an increase in voltage, it is preferred that the electron mobility be at least $10^{-5}$ cm$^2$/Vs or more when an electric field of $10^4$ to $10^6$ V/cm is applied.

Specific examples of the material used in the electron-injecting layer include, though not limited thereto, fluorenone, anthraquinodimethane, diphenoquinone, thiopyrane dioxide, oxazole, oxadiazole, triazole, imidazole, perylene tetracarboxylic acid, fluorenylidenemethane, anthraquinodimethane, anthrone, and derivatives thereof. Further, sensitization is possible by adding an electron-accepting material to a hole-injecting material and an electron-donating material to an electron-injecting material.

In the organic EL device of the invention, a still further effective electron-injecting material is a metal complex compound and a nitrogen-containing five-membered derivative.

Examples of the metal complex compound include, though not limited thereto, 8-hydroxyquinolinate lithium, bis(8-hydroxyquinolinate)zinc, bis(8-hydroxyquinolinolate)copper, bis(8-hydroxyquinolinate)manganese, tris(8-hydroxyquinolinate)aluminum, tris(2-methyl-8-hydroxyquinolinate)aluminum, tris(8-hydroxyquinolinate)gallium, bis(10-hydroxybenzo[h]quinolinate)beryllium, bis(10-hydroxybenzo[h]quinolinate)zinc, bis(2-methyl-8-quinolinate)chlorogallium, bis(2-methyl-8-quinolinate)(o-cresolate)gallium, bis(2-methyl-8-quinolinate)(1-naphtholate)aluminum and bis(2-methyl-8-quinolinate)(2-naphtholate)gallium.

As the nitrogen-containing five-membered derivative, oxazole, thiazole, oxadiazole, thiadiazole and triazole derivatives are preferable. Specific examples include, though not limited thereto, 2,5-bis(1-phenyl)-1,3,4-oxazole, dimethyl POPOP, 2,5-bis(1-phenyl)-1,3,4-thiazole, 2,5-bis (1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis [2-(5-phenyl oxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole and 1,4-bis[2-(5-phenyltriazolyl)]benzene.

In the organic EL device of the invention, the emitting layer may contain, in addition to the polymer of the invention, at least one of an emitting material, a doping material, a hole-injecting material and an electron-injecting material in the same layer. In order to improve stability to temperature, humidity, atmosphere or the like of the organic EL device of the invention, it is possible to provide a protective layer on the surface of the device, or to protect the entire device with silicone oil, a resin or the like.

In the organic EL device of the invention, in order to allow it to emit light efficiently, it is preferred that at least one of the surfaces be fully transparent in the emission wavelength region of the device. In addition, it is preferred that the substrate also be transparent. The transparent electrode is set such that predetermined transparency can be ensured by a method such as deposition or sputtering by using the above-mentioned conductive materials. It is preferred that the electrode on the emitting surface have a light transmittance of 10% or more. Although no specific restrictions are imposed on the substrate as long as it has mechanical and thermal strength and transparency, a glass substrate and a transparent resin film can be given. Examples of the transparent resin film include polyethylene, an ethylene-vinyl acetate copolymer, an ethylene-vinyl alcohol copolymer, polypropylene, polystyrene, polymethylmethacrylate, polyvinyl chloride, polyvinyl alcohol, polyvinyl butyral, nylon, polyetheretherketone, polysulfone, polyethersulfone, a tetrafluoroethylene-perfluoroalkylvinyl ether copolymer, polyvinyl fluoride, a tetrafluoroethylene-ethylene copolymer, a tetrafluoroethylene-hexafluoropropylene copolymer, polychlorotrifluoroethylene, polyvinylidene fluoride, polyester, polycarbonate, polyurethane, polyimide, polyether imide, polyimide and polypropylene.

Each layer of the organic EL device of the invention can be formed by a known method such as a dry film-forming method such as vacuum vapor deposition, sputtering, plasma, and ion plating and a wet film-forming method such as spin coating, dipping and flow coating. Although there are no particular restrictions on the film thickness of each layer, it is required to set it to a suitable film thickness. If the film thickness is too large, a large voltage is required to be applied in order to obtain a certain optical output, resulting in poor efficiency. If the film thickness is too small, pinholes or the like are generated, and hence, a sufficient luminance cannot be obtained even if an electric field is applied. The film thickness is normally in the range of 5 nm to 10 μm, with the range of 10 nm to 0.2 μm being further preferable.

As the method for forming a layer containing the polymer of the invention (the hole-injecting/transporting layer, in particular), forming a solution of the polymer into a film can be mentioned, for example. As the film-forming method, the spin coating method, the casting method, the microphotogravure coating method, the photogravure coating method, the bar coating method, the roll coating method, the slit coating method, the wire bar coating method, the dip coating method, the spray coating method, the screen printing method, the flexo printing method, the offset printing method, the ink-jet method, the nozzle printing method or the like can be mentioned. When a pattern is formed, the screen printing method, the flexo printing method, the offset printing method and the ink jet printing method are preferable. Film formation by these methods can be conducted under conditions which are well known by a person in the art, and hence the details thereof are omitted.

After the film formation, the film is heated (200° C. at most) under vacuum and dried to remove the solvent. No polymerization reaction by light or heating at high temperatures (200° C. or higher) is necessary. Therefore, deterioration of performance by light or heating at high temperatures can be suppressed.

It suffices that the solution for film formation contain at least one kind of the polymer of the invention. In addition to the above-mentioned materials, it may contain a hole-transporting material, an electron-transporting material, an emitting material, an acceptor material, a solvent and an additive such as a stabilizer. The content of the polymer in the solution for film formation is preferably 20 to 100 wt %, more preferably 40 to 100 wt % relative to the total weight of the composition excluding the solvent. The amount ratio of the solvent is preferably 1 to 99.9 wt % relative to the solution for film formation, with 80 to 99 wt % being more preferable.

The solution for film formation may contain an additive for controlling the viscosity and/or the surface tension, for example, a thickener (a high molecular compound, a poor solvent for the high-molecular compound of the invention, or the like), a viscosity reducing agent (a low-molecular compound or the like), a surfactant or the like. In order to improve storage stability, an antioxidant which does not affect the performance of the organic EL device, such as a phenol-based antioxidant and a phosphor-based antioxidant may be contained.

Examples of the usable high-molecular compounds include insulative resins such as polystyrene, polycarbonate, polyarylate, polyester, polyamide, polyurethane, polysulfone, polymethylmethacrylate, polymethylacrylate and cellulose, copolymers thereof, photoconductive resins such as poly-N-vinylcarbazole and polysilane and conductive resins such as polythiophene and polypyrrole.

Example of the solvent for the solution for film formation include chlorine-based solvents such as chloroform, methylene chloride, 1,2-dichloroethane, 1,1,2-trichloroethane, chlorobenzene and o-dichlorobenzene; ether-based solvents such as tetrahydrofuran, dioxane, dioxolane, and anisole; aromatic hydrocarbon solvents such as toluene and xylene; aliphatic hydrocarbon-based solvents such as cyclohexane, methylcyclohexane, n-pentane, n-hexane, n-heptane, n-octane, n-nonane and n-decane; ketone-based solvents such as acetone, methylethylketone, cyclohexanone, benzophenone and acetophenone; ester-based solvents such as ethyl acetate, butyl acetate, ethyl cellosolve acetate, methyl benzoate and phenyl acetate; polyvalent alcohols such as ethylene glycol, ethylene glycol monobutyl ether, ethylene glycol monoethyl ether, ethylene glycol monomethyl ether, dimethoxy ethane, propylene glycol, diethoxymethane, triethylene glycol monoethyl ether, glycerin, 1,2-hexanediol and derivatives thereof; alcohol-based solvents such as methanol, ethanol, propanol, isopropanol and cyclohexanol; sulfoxide-based solvents such as dimethylsulfoxide; and amide-based solvents such as N-methyl-2-pyrrolidone and N,N-dimethylformamide can be mentioned. These organic solvents may be used alone or in combination of two or more. Of these, in respect of solubility, homogeneity of a coating film, viscosity properties or the like, aromatic hydrocarbon-based solvents, ether-based solvents, aliphatic hydrocarbon-based solvents, ester-based solvents and ketone-based solvents are preferable. Toluene, xylene, ethylbenzene, diethylbenzene, trimethylbenzene, n-propylbenzene, isopropylbenzene, n-butylbenzene, isobutylbenzene, 5-butylbenzene, n-hexylbenzene, cyclohexylbenzene, 1-methylnaphthalene, tetralin, 1,3-dioxane, 1,4-dioxane, 1,3-dioxolane, anisole, ethoxybenzene, cyclohexane, bicyclohexyl, cyclohexeny cyclohexanone, n-heptylcyclohexane, n-hexylcyclohexane, decaline, methyl benzoate, cyclohexanone, 2-propylcyclohexanone, 2-heptanone, 3-heptanone, 4-heptanone, 2-octanone, 2-nonanone, 2-decanone, dicyclohexylketone, acetophenone and benzophenone are more preferable.

<Method for Producing an Organic EL Device>

The organic EL device can be fabricated by forming an anode, optionally a hole-injecting/transporting layer, an emitting layer, and optionally an electron-injecting/transporting layer, and further forming a cathode using the materials and methods exemplified above. The organic EL device can be fabricated in the order reverse to the above, i.e., the order from a cathode to an anode.

EXAMPLES

The invention will be explained below in detail with reference to Examples, which should not be construed as limiting the scope of the invention.

Example

Synthesis of Various Monomers

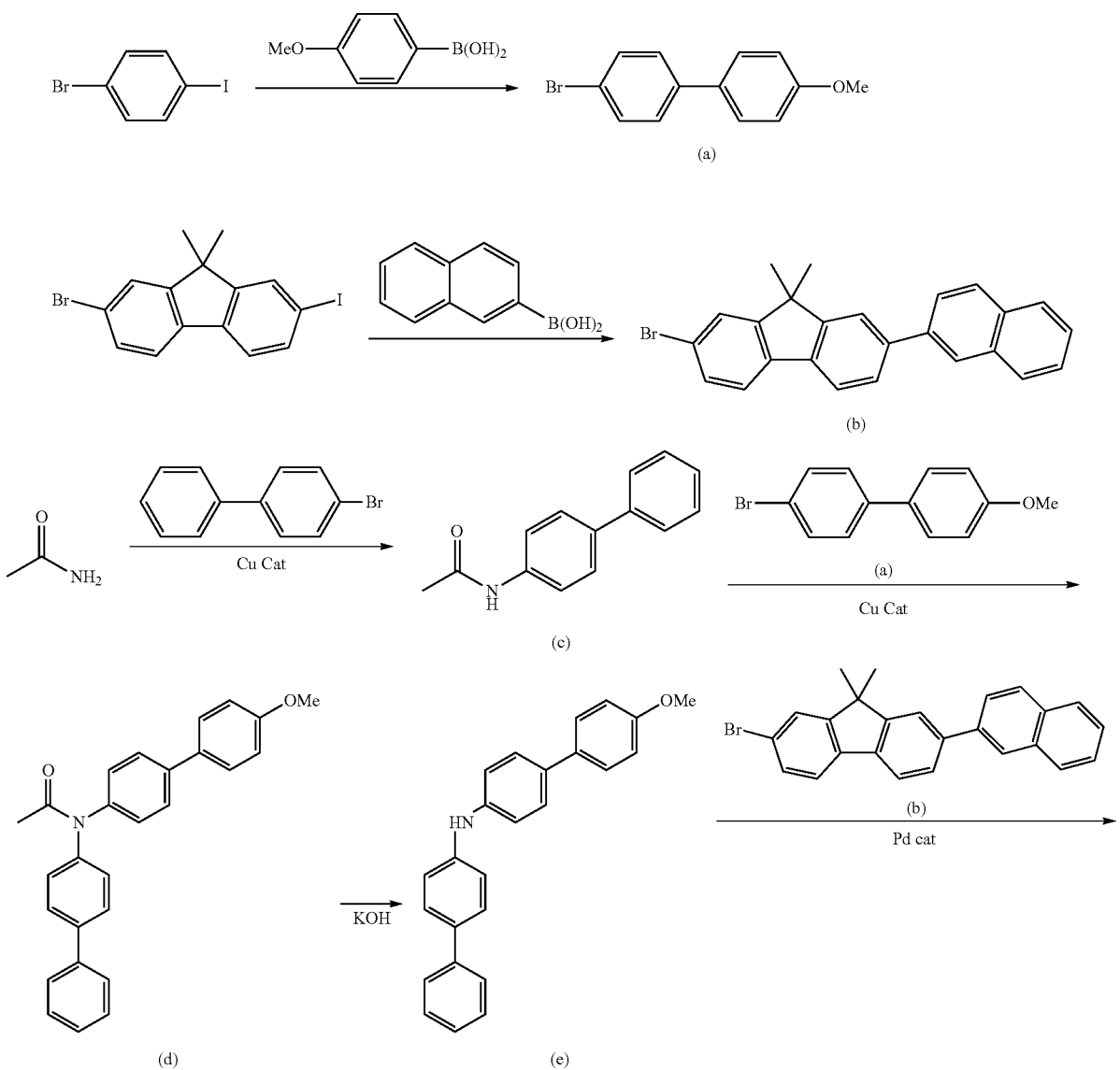

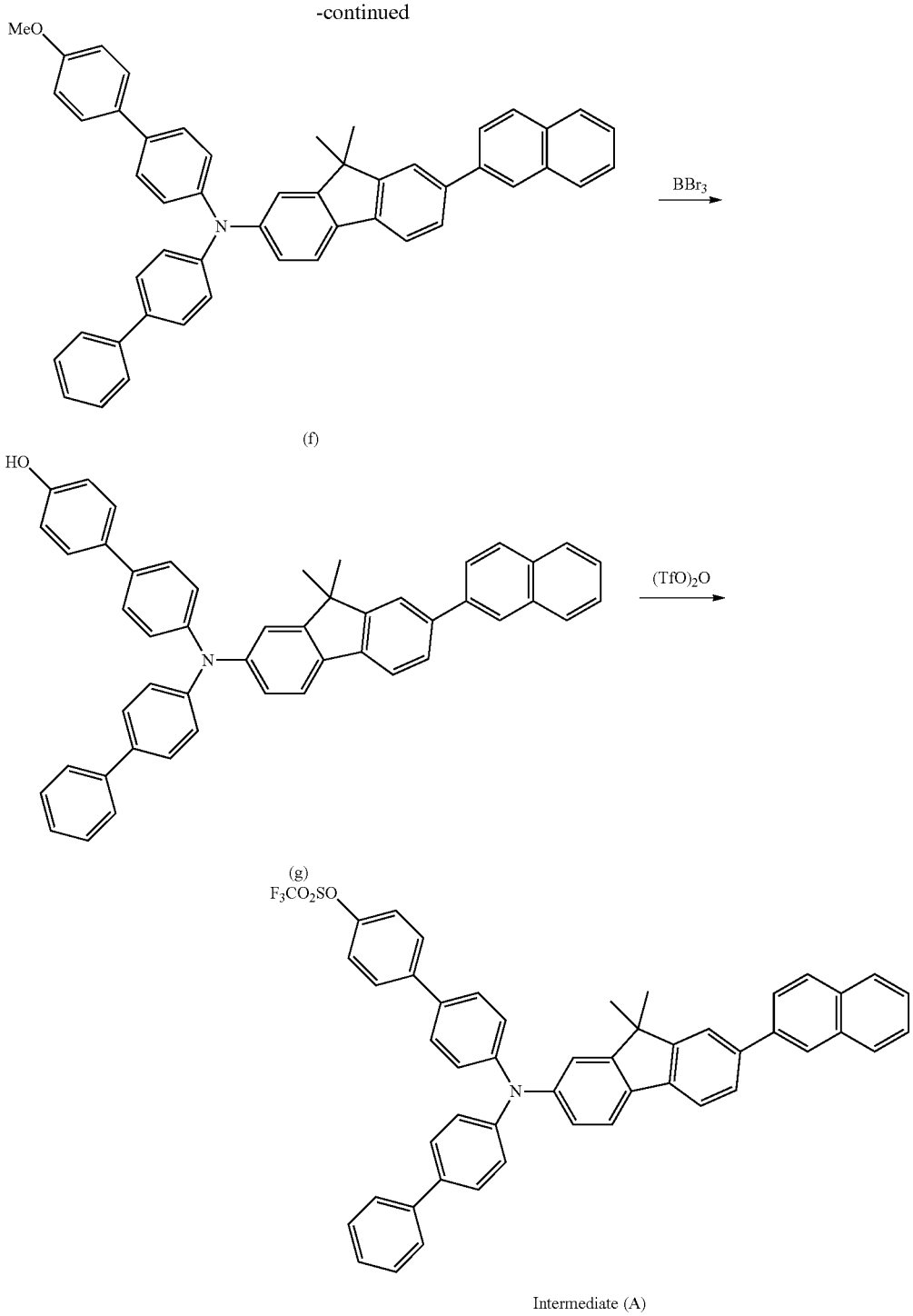

Intermediate (A)

Synthesis of Intermediate (A)
<First Step>

17.0 g (60 mmol) of 4-bromo-iodophenyl, 9.1 g (60 mmol) of 4-methoxyphenylboronic acid, 1.4 g of Pd(PPh$_3$)$_4$, 21.9 g of sodium carbonate, clean water and dimethoxyethane were put, and the resulting mixture was allowed to react for 8 hours under reflux for 8 hours.

After cooling, the reaction solution was filtered, and the filtrate was extracted with dichloromethane. The dichloromethane phase was washed with water to concentrate, and the resulting crude product was purified by means of silica gel chromatography. The solids thus obtained were recrystallized from toluene and methanol, and dried under reduced pressure, whereby 7.9 g of white solids were obtained (yield 50%). By analysis by FD-MS (field desorption mass spectrometry), the white solids were identified as the intermediate (a).

<Second Step>

23.9 g (60 mmol) of 2-bromo-7-iodo-9,9-dimethylfluorene, 10.3 g (60 mmol) of 2-naphthylboronic acid, 1.4 g of Pd(PPh$_3$)$_4$, 21.9 g of sodium carbonate, clean water and dimethoxyethane were put, and the resulting mixture was allowed to react under reflux for 8 hours.

After cooling, the reaction solution was filtered, and the filtrate was extracted with dichloromethane. The dichloromethane phase was washed with water to concentrate, and the resulting crude product was purified by means of silica gel chromatography. The solids thus obtained were re-crystallized from toluene and methanol, and dried under reduced pressure, whereby 10.8 g of white solids were obtained (yield 45%). By analysis by FD-MS (field desorption mass spectrometry), the white solids were identified as the intermediate (b).

<Third Step>

In an argon atmosphere, to a 500 mL-three neck flask provided with a condenser tube, 2.4 g (40 mmol) of acetoamide, 11.2 g (48 mmol) of 4-phenyl-1-bromobenzene, 6.2 g (32 mmol) of copper iodide, 4.3 g (48 mmol) of N,N-dimethylethylenediamine, 22.4 g (160 mol) of potassium carbonate and 200 mL of dehydrated xylene were added. The resultant was stirred with heating at 100° C. overnight. After the reaction was completed, the reaction solution was filtered, and filtrates obtained were washed with water. The xylene phase was concentrated, and crystals deposited were isolated, and washed with 100 mL of toluene and 200 mL of methanol, whereby 4.4 g of pale yellow powder was obtained (Intermediate (c), yield 52%).

<Fourth Step>

In an argon atmosphere, to a 300 mL-three neck flask provided with a condenser tube, 4.2 g (20 mmol) of intermediate (c), 6.3 g (24 mmol) of intermediate (a), 3.1 g (16 mmol) of copper iodide, 2.1 g (24 mmol) of N,N-dimethylethylenediamine, 11.2 g (80 mol) of potassium carbonate and 100 mL of dehydrated xylene were added. The resultant was stirred with heating at 100° C. overnight. After the reaction was completed, the reaction solution was filtered, and the resultant was washed with water. The xylene phase was concentrated, crystals deposited were isolated, and purified by column chromatography by using toluene as a solvent, whereby 4.7 g of pale yellow powder was obtained (Intermediate (d), yield 60%).

<Fifth Step>

To a 300 mL-three neck flask provided with a condenser tube, 5.6 g (14 mmol) of intermediate (d), 5.6 g (100 mmol) of potassium hydroxide, 100 mL of ethanol and 100 mL of toluene were added. The resultant was stirred with heating at 80° C. overnight. After the reaction was completed, the reaction solution was filtered, and the toluene phase which had been washed with water was concentrated, crystals deposited were isolated, and washed with 100 mL of toluene and 100 mL of methanol, whereby 3.7 g of pale yellow powder was obtained (Intermediate (e), yield 75%).

<Sixth Step>

In an argon atmosphere, to a 300 mL-three neck flask provided with a condenser tube, 4.0 g (10 mmol) of intermediate (b), 3.5 g (10 mmol) of intermediate (e), 0.02 g (0.1 mmol) of palladium acetate, 0.1 g (0.5 mmol) of tri-t-butylphosphine, 0.7 g (7 mmol) of t-butoxysodium and 100 mL of dry toluene were added. The resultant was stirred with heating at 100° C. overnight. After the reaction was completed, the deposited crystals were filtered out, and purified by means of column chromatography using toluene as a solvent, whereby 5.4 g of pale yellow powder was obtained (Intermediate (f), yield 80%).

<Seventh Step>

Subsequently, in an argon atmosphere, in a 300 mL-three neck flask, 5.4 g (8 mmol) of the intermediate (f) was dissolved in 100 mL of dehydrated methylene chloride. After cooling at 10° C., a methylene chloride solution of 2.11 g (8.4 mmol) of boron tribromide was added dropwise, and the resultant was stirred at room temperature for 4 hours. After treating the reaction liquid with water, a methylene chloride phase was extracted and concentrated. Column chromatography was conducted using toluene as a solvent, whereby 4.7 g of pale yellow powder was obtained (intermediate (g), yield 90%).

<Eighth Step>

In an argon atmosphere, in a 300 mL-three neck flask, 3.3 g (5.0 mmol) of the intermediate (g) and 1.0 g (10 mmol) of diisopropylamine were dissolved in 100 mL of dehydrated methylene chloride. After cooling at 0° C., a dehydrated methylene chloride solution of 3.1 g (11 mmol) of trifluoromethane sulfonic anhydride was added dropwise, and the resulting mixture was stirred at room temperature for 21 hours. After neutralizing with a 5% aqueous solution of sodium carbonate, the methylene chloride phase was extracted and concentrated. Column chromatography was conducted by using toluene, whereby 3.5 g of pale yellow powder was obtained (intermediate (A), yield 88%).

Monomers (1) to (6) were synthesized according to the following synthesis scheme.

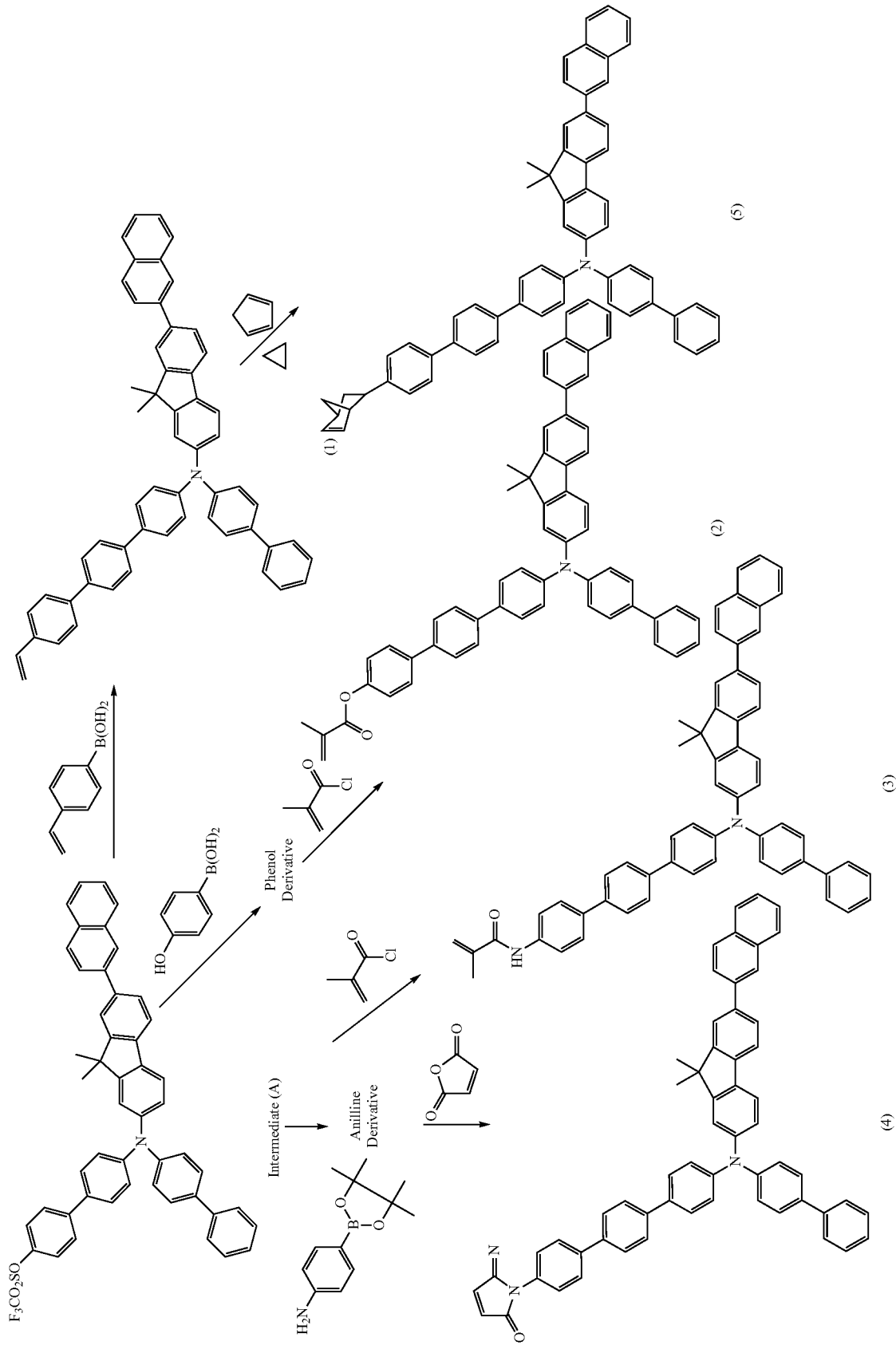

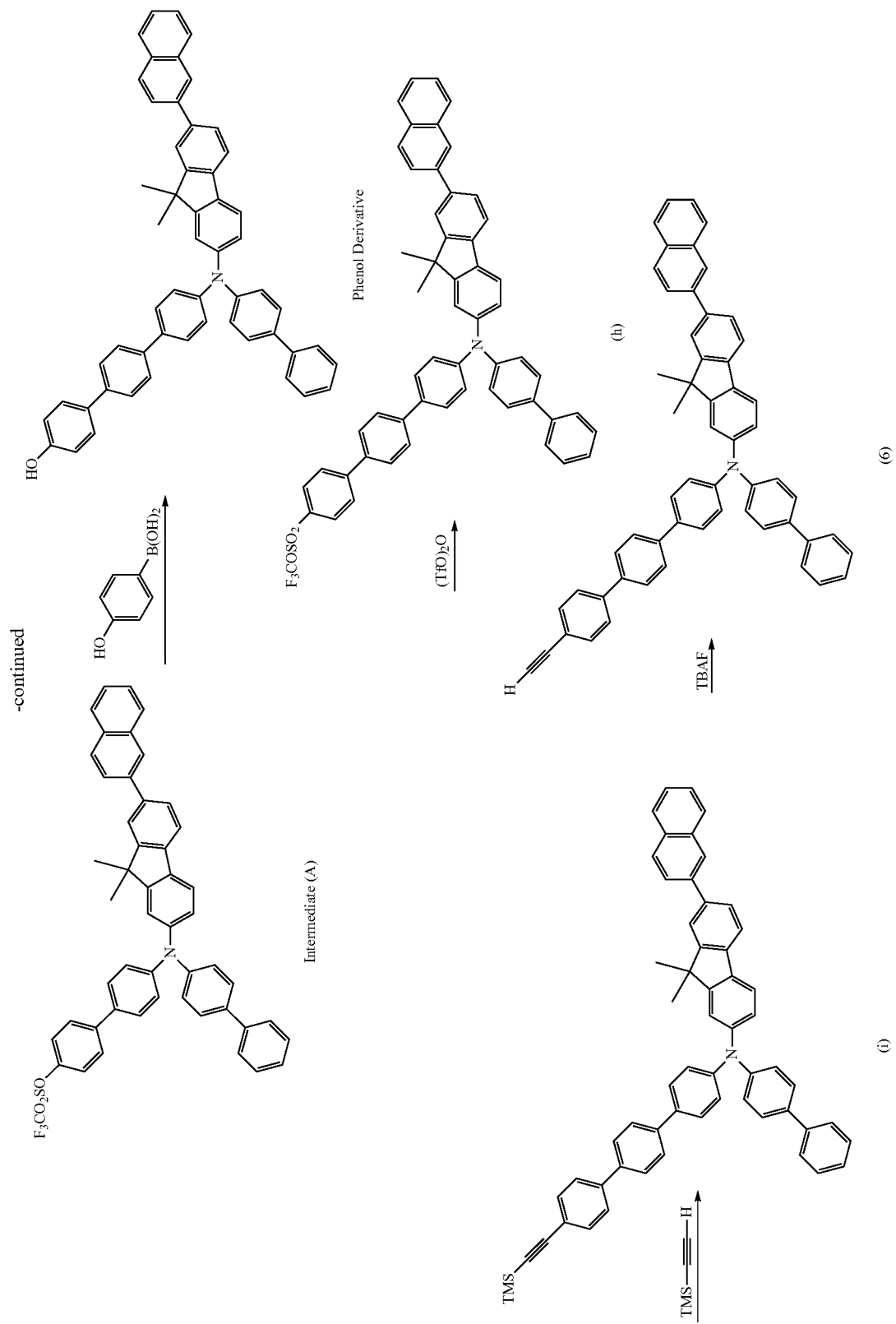

Example 1

In an argon atmosphere, to a 100 mL-three neck flask provided with a condenser tube, 2.4 g (3 mmol) of the intermediate (A), 0.4 g (3 mmol) of 4-vinylphenylboronic acid, 0.7 g (60 µmol) of tetrakistriphenylphosphine palladium (0), 1.0 g (9 mmol) of sodium carbonate and 50 mL of dry toluene were added. The resulting mixture was stirred with heating at 80° C. for 24 hours. After the reaction was completed, the deposited crystals were filtered out, and column chromatography was conducted by using toluene as a solvent, whereby 1.7 g of pale yellow powder was obtained. As a result of NMR, MS or the like, the powder was confirmed to be an intended product (1) (yield 75%).

Example 2

In an argon atmosphere, to a 100 mL-three neck flask provided with a condenser tube, 2.4 g (3 mmol) of the intermediate (A), 0.4 g (3 mmol) of 4-hydroxyphenylboronic acid, 0.7 g (60 µmol) of tetrakistriphenylphosphine palladium (0), 1.0 g (9 mmol) of sodium carbonate and 50 mL of dry toluene were added. The resulting mixture was stirred with heating at 80° C. for 24 hours. After the reaction was completed, the deposited crystals were filtered out, and column chromatography was conducted by using toluene as a solvent, whereby pale yellow powder was obtained (phenol derivative).

Next, in an argon atmosphere, in a 100 mL-three neck flask, the above-mentioned phenol derivative and 0.5 g (5 mmol) of triethylamine were dissolved in 50 mL of dehydrated toluene. After cooling the reaction mixture at 0° C., a dehydrated toluene solution of 0.3 g (3 mmol) of methacrylic chloride was added dropwise, and the resulting mixture was stirred at room temperature for 10 hours. The deposited salts were filtered out, the filtrate was concentrated, and column chromatography was conducted by using toluene as a solvent, whereby 1.5 g of pale yellow powder was obtained (phenol derivative). As a result of NMR, MS or the like, the powder was confirmed to be an intended product (2) (yield 63%).

Example 3

In an argon atmosphere, to a 100 mL-flask provided with a condenser tube, 2.4 g (3 mmol) of the intermediate (A), 0.6 g (3 mmol) of 4-(4,4,5,5-tetramethyl-1,3,2-dioxaborolane-2-yl)aniline, 0.7 g (60 µmol) of tetrakistriphenylphosphine palladium (0), 1.0 g (9 mmol) of sodium carbonate and 50 mL of dry toluene were added. The resulting mixture was stirred with heating at 80° C. for 24 hours. After the reaction was completed, the deposited crystals were filtered out, and column chromatography was conducted by using toluene as a solvent, whereby pale yellow powder was obtained (aniline derivative).

Next, in an argon atmosphere, in a 100 mL-three neck flask, the above-mentioned aniline derivative and 0.5 g (5 mmol) of triethylamine were dissolved in 50 mL of dehydrated toluene. After cooling the reaction mixture at 0° C., a dehydrated toluene solution of 0.3 g (3 mmol) of methacrylic chloride was added dropwise, and the resulting mixture was stirred at room temperature for 10 hours. The deposited salts were filtered out, the filtrate was concentrated and column chromatography was conducted by using toluene as a solvent, whereby 1.5 g of pale yellow powder was obtained. As a result of NMR, MS or the like, the powder was confirmed to be an intended product (3) (yield 62%).

Example 4

In an argon atmosphere, to a 100 mL-three neck flask provided with a condensor, 2.4 g (3 mmol) of the intermediate (A), 0.6 g (3 mmol) of 4-(4,4,5,5-tetramethyl-1,3,2-dioxaborolane-2-yl)aniline, 0.7 g (60 µmol) of tetrakistriphenylphosphine palladium (0), 1.0 g (9 mmol) of sodium carbonate and 50 mL of dry toluene were added. The resulting mixture was stirred with heating at 80° C. for 24 hours. After the reaction was completed, the deposited crystals were filtered out, and column chromatography was conducted by using toluene as a solvent, whereby pale yellow powder was obtained (aniline derivative).

Next, in a 100 mL-three neck flask, the above-mentioned aniline derivative and 0.3 g (3 mmol) of maleic anhydride were dissolved in 50 mL of chloroform. The resulting mixture was allowed to react for 4 hours at room temperature. Next, after distilling the solvent off, 1.2 g (15 mmol) and 50 mL of acetic anhydride were added, and the resulting mixture was allowed to react at 100° C. for 5 hours. The reaction liquid was dropped in the water, and deposited products were filtered out. Next, the deposited products were subjected to column chromatography using toluene as a solvent, whereby 2.0 g of pale yellow powder was obtained. As a result of NMR, MS or the like, the powder was confirmed to be an intended product (4) (yield 80%).

Example 5

Diels-Alder Reaction

All of the reactions were conducted in an argon atmosphere. To a 200 mL-three neck flask provided with a condenser tube, 1.1 g (1.44 mmol) of compound (1) synthesized in the same manner as in Example 1 and 150 mL of toluene as a solvent were added, and the resultant was stirred with heating to allow the compound (1) to be completely dissolved in the toluene. This solution was allowed to stand until the temperature thereof became room temperature. Subsequently, 10 g (150 mmol) of cyclopentadiene which had been distilled immediately before use and a small amount of p-toluenesulfonic acid were added, and the resultant was allowed to react at room temperature for 2 hours. The resultant was then allowed to further react at 75° C. for 5 hours. This reaction liquid was poured to a large amount of hexane (about 1000 mL), and solid components generated were filtered out. The solid components were purified by means of column chromatography by using a methylene chloride/hexane mixed solvent as an eluent, whereby 0.7 g of pale yellow powder (compound (5), yield 63%) was obtained. The powder was confirmed to be an intended product by NMR, MS or the like.

Example 6

In an argon atmosphere, to a 100 mL-three neck flask provided with a condenser tube, 2.4 g (3 mmol) of intermediate (A), 0.4 g (3 mmol) of 4-hydroxyphenylboronic acid, 0.7 g (60 µmol) of tetrakistriphenylphosphine palladium (0), 1.0 g (9 mmol) of sodium carbonate and 50 mL of dry toluene were added. The resultant was stirred with heating at 80° C. for 24 hours. After the completion of the reaction, crystals deposited were filtered out, and column chromatography was conducted by using toluene as a solvent, whereby pale yellow powder was obtained (phenol derivative).

Subsequently, in an argon atmosphere, in a 100 mL-three neck flask, the phenol derivative 2 and 0.6 g (6 mmol) of diisopropylamine were dissolved in 50 mL of dehydrated methylene chloride. After cooling at 0° C., a dehydrated methylene chloride solution of 1.6 g (6 mmol) of trifluoromethanesulfonic anhydride was added dropwise, and the resultant was stirred at room temperature for 21 hours. Next, the reaction solution was neutralized in a 5% aqueous sodium carbonate solution, and the methylene chloride phase was extracted and concentrated. Column chromatography was conducted by using toluene as a solvent, whereby 2.1 g of pale yellow powder was obtained (Intermediate (h), yield 80%).

Next, in an argon atmosphere, in a 100 mL-three neck flask, 2.1 g (2.4 mmol) of the above-mentioned intermediate (h) was dissolved in 50 mL of N,N-dimethylformamide (DMF). To the resulting mixture, 0.24 g (2.4 mmol) of trimethylsilylacetylene, 9.2 mg (0.024 mmol) of bis(benzonitrile)palladium (II) chloride complex, 4.6 mg (0.024 mmol) of copper iodide, 0.24 g (2.4 mmol) of triethylamine and 4.9 mg (0.024 mmol) of tri-tert-butylphosphine were added, and the resulting mixture was stirred with heating at 80° C. for 10 hours. A large amount of ethyl acetate was added to the reaction solution and the resultant was filtered through celite to allow ethyl acetate and DMF to be distilled off under reduced pressure, whereby a crude product of intermediate (i) was obtained.

Subsequently, in a 100 mL-three neck flask, a crude product of this intermediate (i) was dissolved in 100 mL of methylene chloride. To the resulting solution, 0.8 g of TBAF (tetrabutylammonium fluoride) was added, and the resultant was allowed to react at room temperature for 5 hours. The methylene chloride was distilled off under reduced pressure from this reaction liquid. The reaction liquid was purified by column chromatography by using a methylene chloride/hexane mixed solvent as an eluent, whereby 0.53 g of an intended compound (compound (6), yield 30%) was obtained. The compound was confirmed to be the intended product by NMR, MS or the like.

Synthesis of Intermediate (B)

Intermediate (B) was synthesized according to the following scheme, with reference to the synthesis method of the intermediate (A).

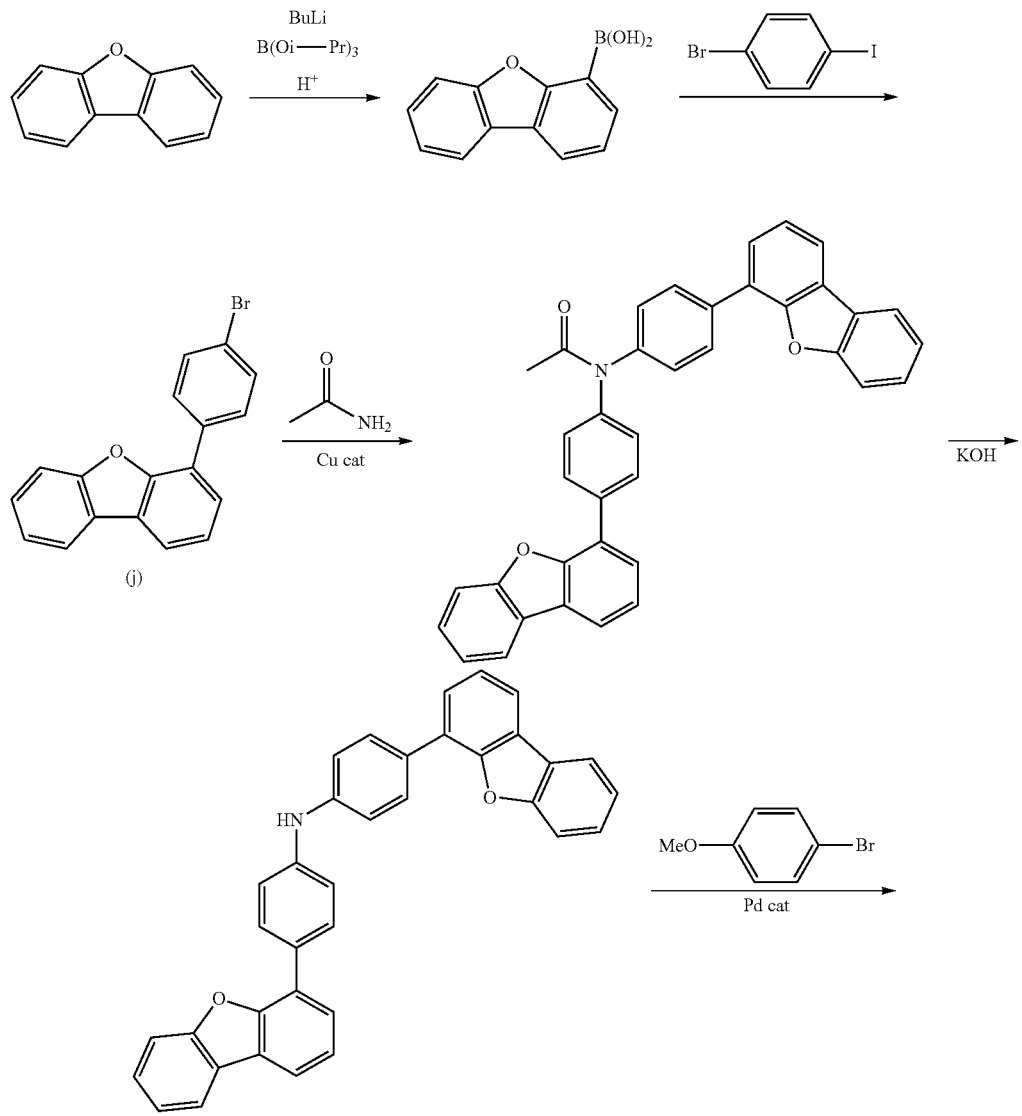

-continued
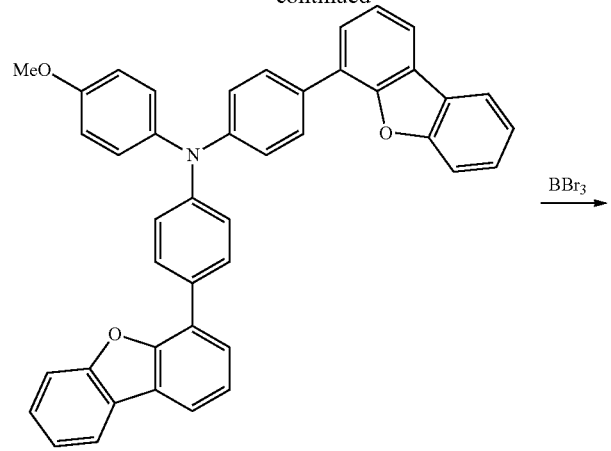
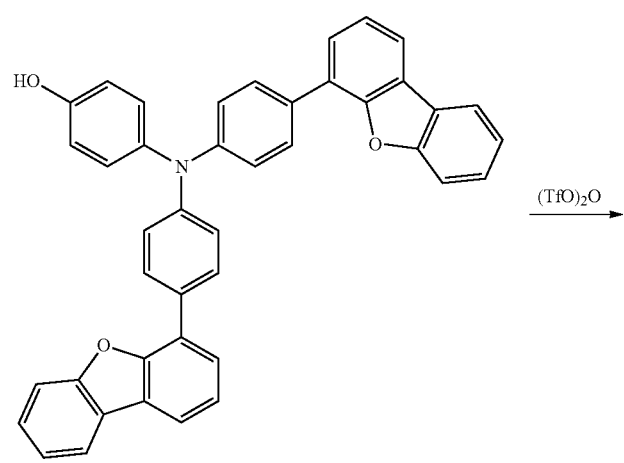
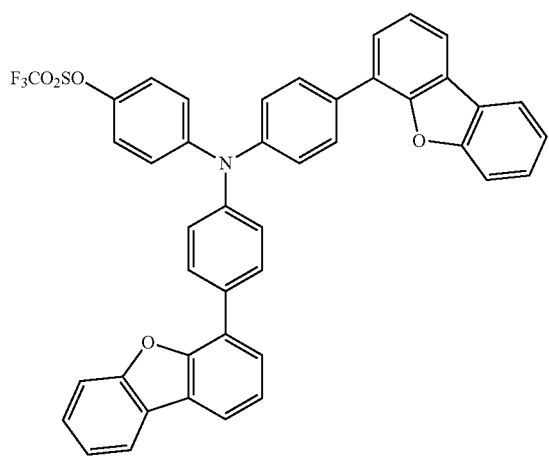
Intermediate (B)
Synthesis of Intermediate (C)
Intermediate (C) was synthesized according to the following scheme, with reference to the synthesis method of the intermediate (A).

107
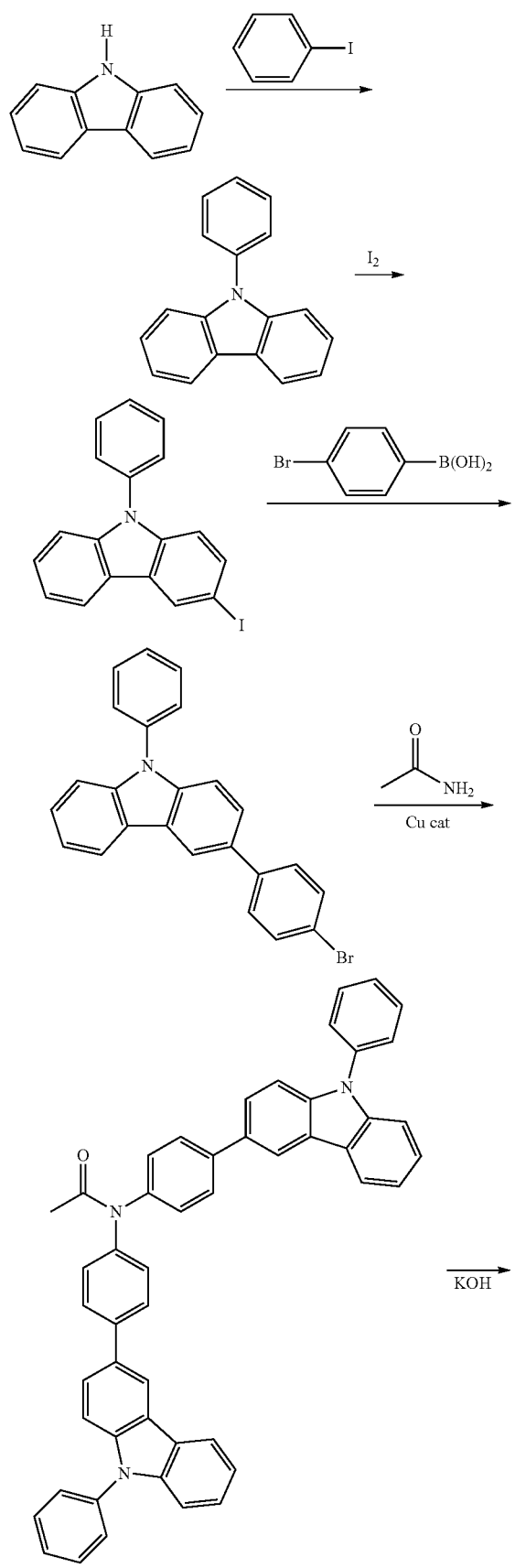
108
-continued
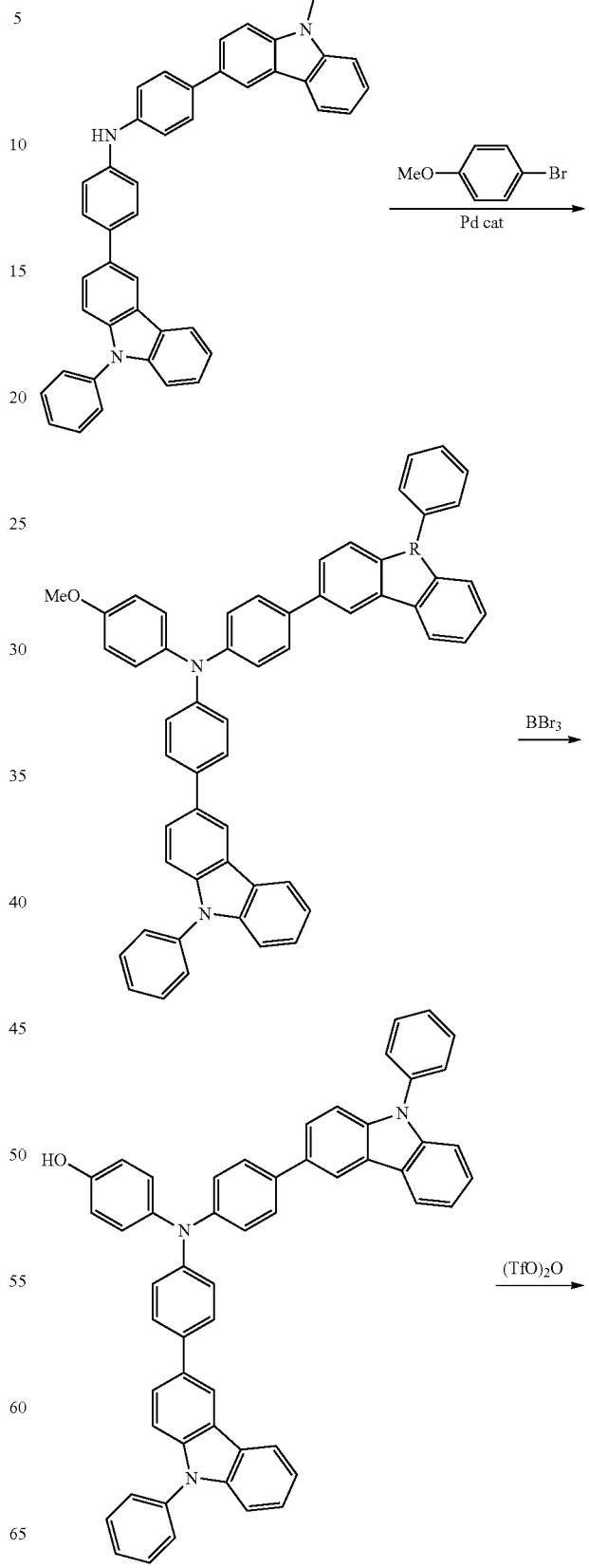

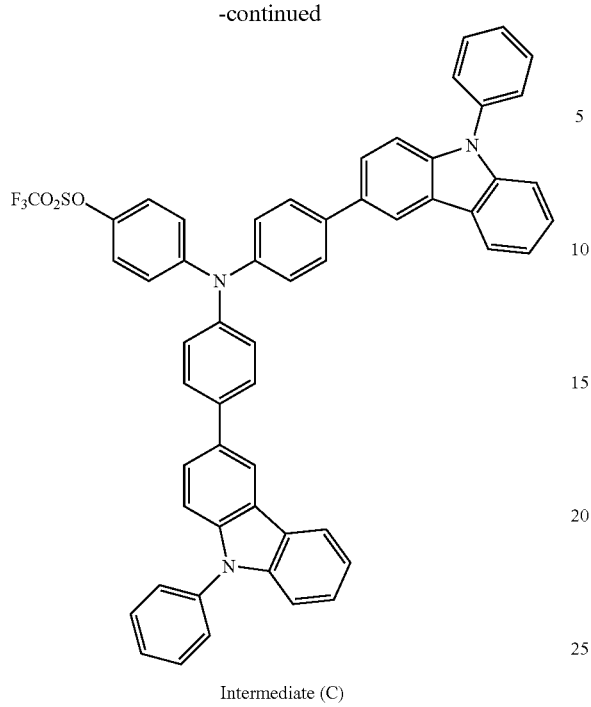
Intermediate (C)
Synthesis of Intermediate (D)
Intermediate (D) was synthesized according to the following scheme with reference to the synthesis method of the intermediate (A).
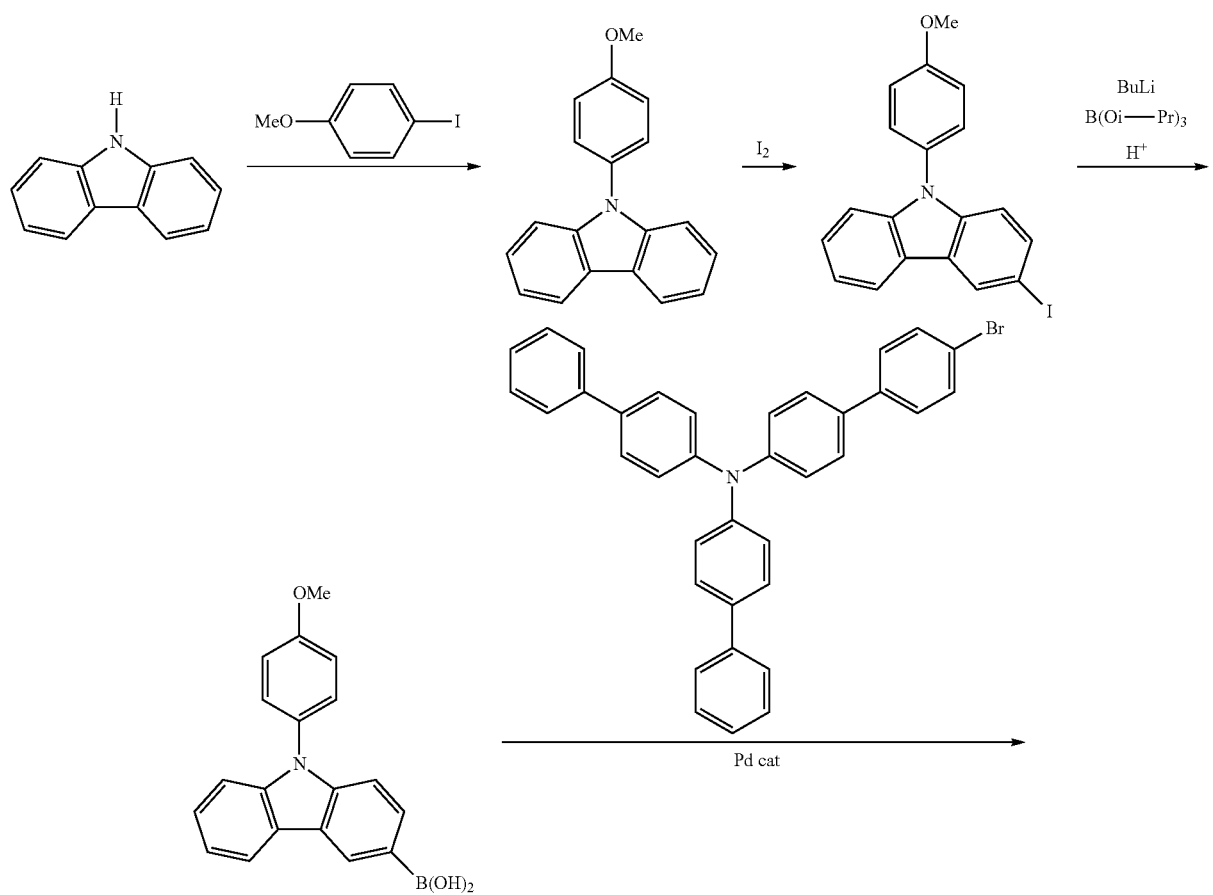

111
-continued
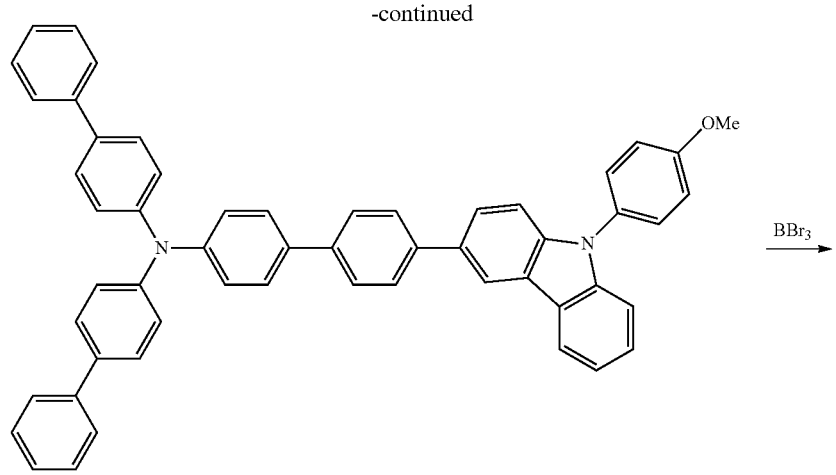
BBr₃ →
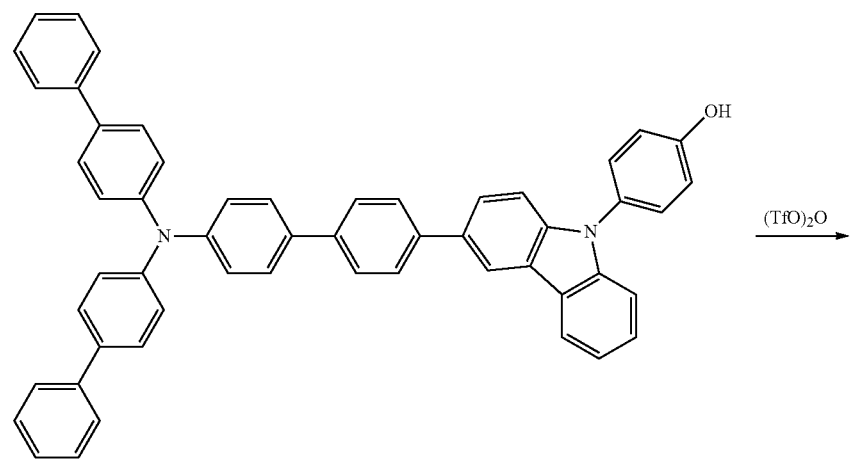
(TfO)₂O →
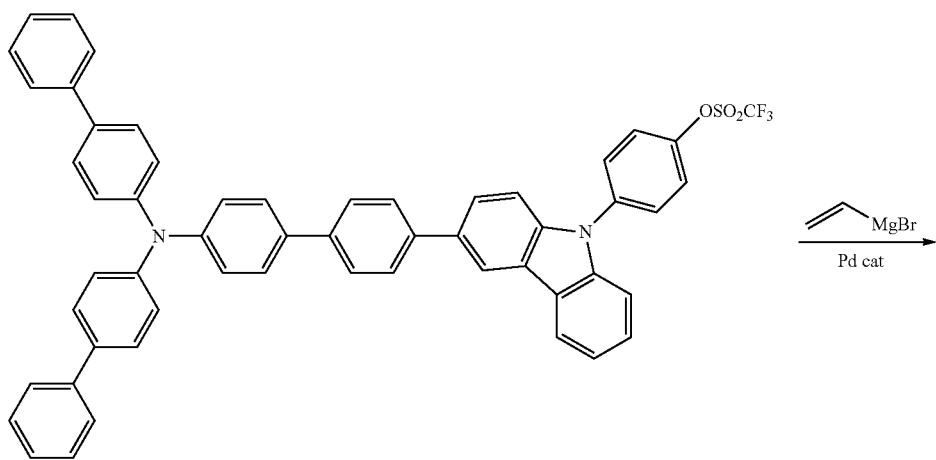
Intermediate (D)
$\overset{\text{MgBr}}{\underset{\text{Pd cat}}{\xrightarrow{\hspace{1cm}}}}$
112

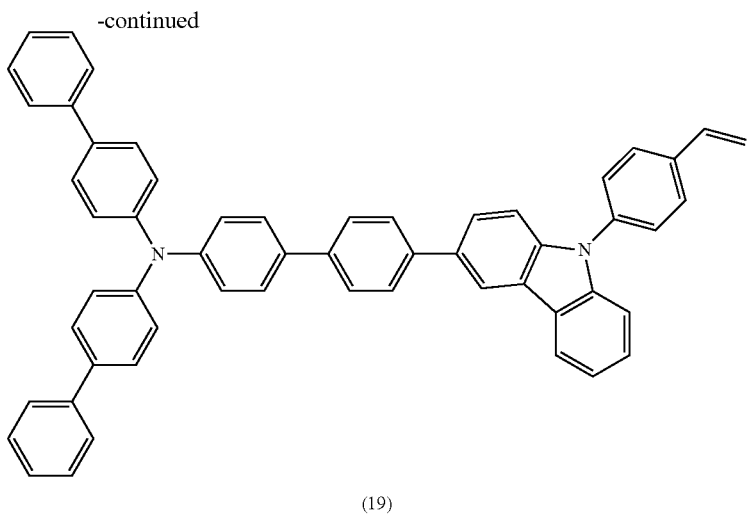
(19)
Example 7
An intended product (7) was obtained in the same manner as in Example 1, except that the intermediate (B) was used instead of the intermediate (A).
Example 8
Synthesis of Intermediate (E)
Intermediate (E) was synthesized according to the following scheme.
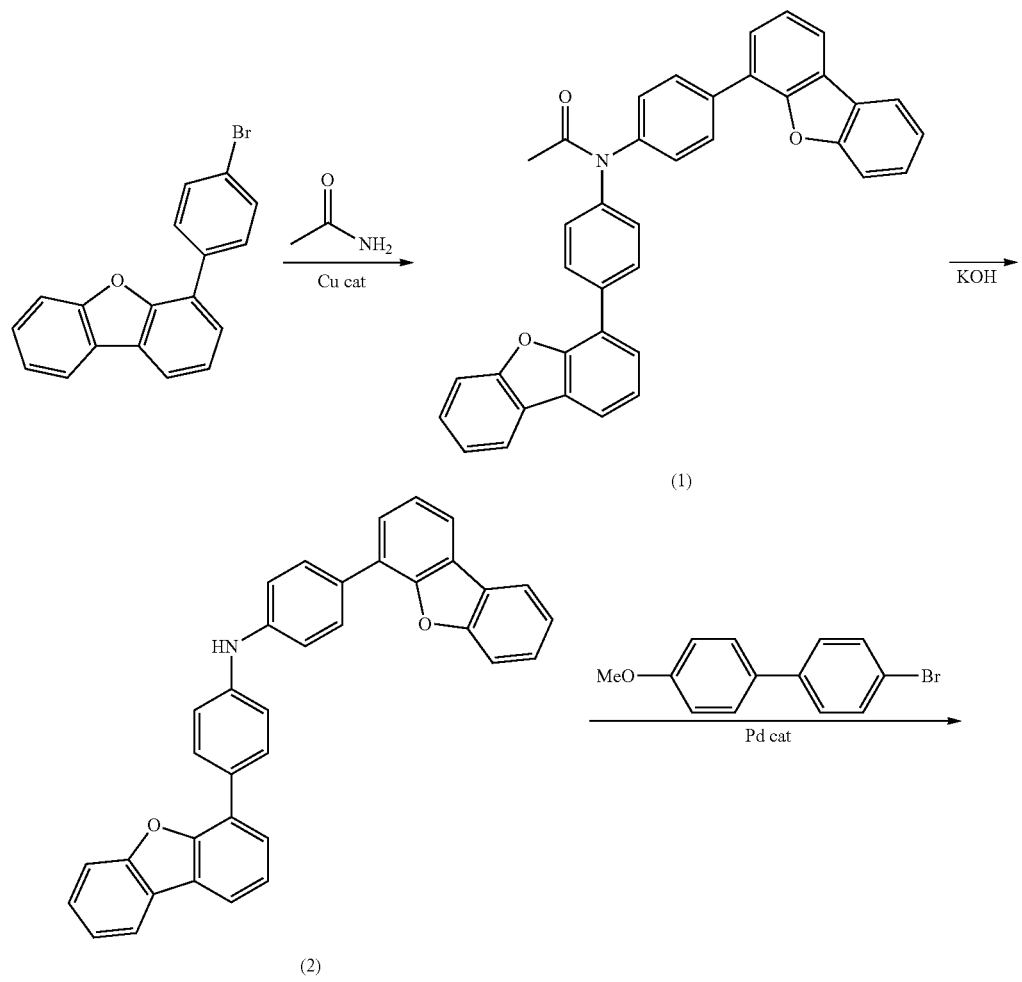

-continued
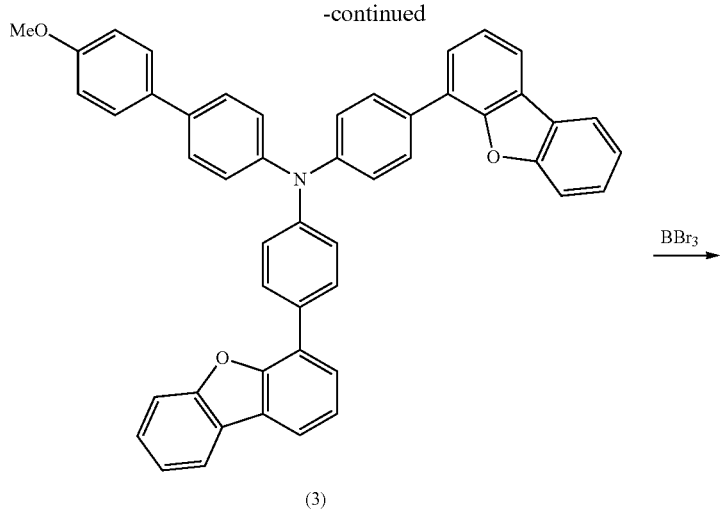
(3)
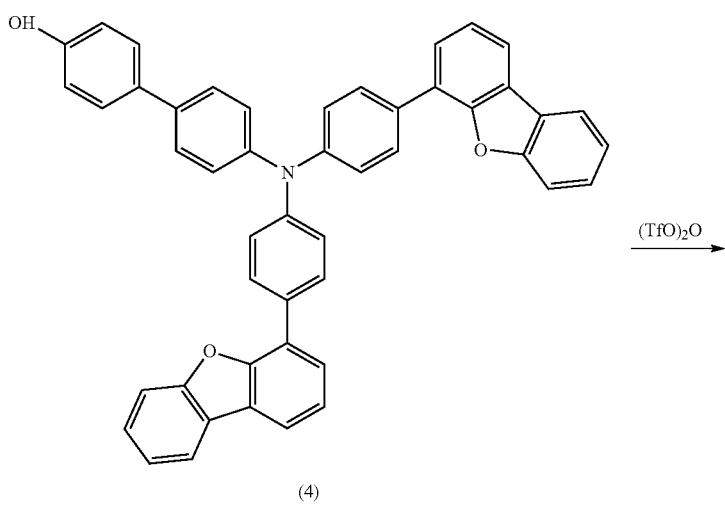
(4)
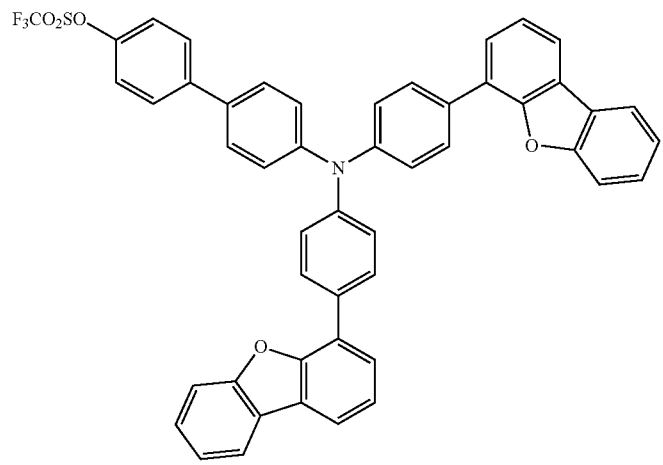
Intermediate (E)

In an argon atmosphere, to a 500 mL-three neck flask provided with a condenser tube, 2.4 g (40 mmol) of acetoamide, 31.0 g (96 mmol) of 4-(p-bromophenyl)dibenzofuran, 6.2 g (32 mmol) of copper iodide, 4.3 g (48 mmol) of N,N-dimethylethylenediamine, 22.4 g (160 mol) of potassium carbonate and 200 mL of dehydrated xylene were added. The resultant was stirred with heating at 100° C. overnight. After the completion of the reaction, filtration and washing with water were conducted. Then, the xylene phase was concentrated and deposited crystals were taken out. The crystals were then washed with 100 mL of toluene and 200 mL of methanol, whereby 12.9 g of pale yellow powder was obtained (intermediate (1), yield 52%).

To a 300 mL-flask provided with a condenser tube, 11.5 g (20 mmol) of the intermediate (1), 5.6 g (100 mmol) of potassium hydroxide, 100 mL of ethanol and 100 mL of toluene were added, and the resulting mixture was stirred with heating at 80° C. overnight. After the completion of the reaction, the toluene phase which had been washed with water was concentrated, deposited crystals were taken out, and washed with 100 mL of toluene and 100 mL of methanol, whereby 8.0 g of pale yellow powder was obtained (intermediate (2), yield 75%).

In an argon atmosphere, to a 300 mL-three neck flask provided with a condenser tube, 4.0 g (10 mmol) of the intermediate (2), 2.6 g (10 mmol) of 4-bromo-4'-methoxybiphenyl, 0.02 g (0.1 mmol) of palladium acetate, 0.1 g (0.5 mmol) of tri-t-butylphoshine, 0.7 g (7 mmol) of t-butoxysodium and 100 mL of dry toluene were added. The resulting solution was stirred with heating at 100° C. overnight. After the completion of the reaction, deposited crystals were filtered out, and purified by means of column chromatography using toluene as an eluent, whereby 5.7 g of pale yellow powder was obtained (intermediate (3), yield 80%).

In an argon atmosphere, in a 300 mL-three neck flask, 5.1 g (7.1 mmol) of the intermediate (3) was dissolved in 100 mL of dehydrated methylene chloride. After cooling at 10° C., a methylene chloride solution of 2.11 g (8.4 mmol) of boron tribromide was added dropwise. The resulting solution was stirred at room temperature for 4 hours. After treating the reaction liquid with water, the methylene chloride phase was extracted, concentrated and column chromatography was conducted using toluene as an eluent, whereby 4.5 g of pale yellow powder was obtained (intermediate (4), yield 90%).

In an argon atmosphere, in a 100 mL-three neck flask, 4.0 g (5.7 mmol) of the intermediate (4) and 0.9 g (9 mmol) of diisopropylamine were dissolved in 50 mL of dehydrated methylene chloride. After cooling at 0° C., a dehydrated methylene chloride solution of 2.4 g (9 mmol) of trifluoromethanesulfonic acid anhydride was added dropwise, followed by stirring at room temperature for 21 hours. Subsequently, after neutralizing with an aqueous 5% sodium carbonate solution, the methylene chloride phase was extracted and concentrated. Column chromatography using toluene as a solvent was conducted, whereby 4.4 g of pale yellow powder was obtained (intermediate (E), yield 92%).

Synthesis of Intended Product (8)

In an argon atmosphere, to a 100 mL-three neck flask provided with a condenser tube, 2.5 g (3 mmol) of the intermediate (X), 0.4 g (3 mmol) of 4-vinylphenylboronic acid, 0.7 g (60 μmol) of tetrakistriphenylphosphine palladium (0), 1.0 g (9 mmol) of sodium carbonate and 50 mL of dry toluene were added, followed by stirring with heating at 80° C. for 24 hours. After the completion of the reaction, deposited crystals were filtered out, and column chromatography was conducted using toluene as a solvent, whereby 1.7 g of pale yellow powder was obtained. The compound was confirmed to be the intended product (8) by NMR, MS or the like (monomer (8), yield 75%).

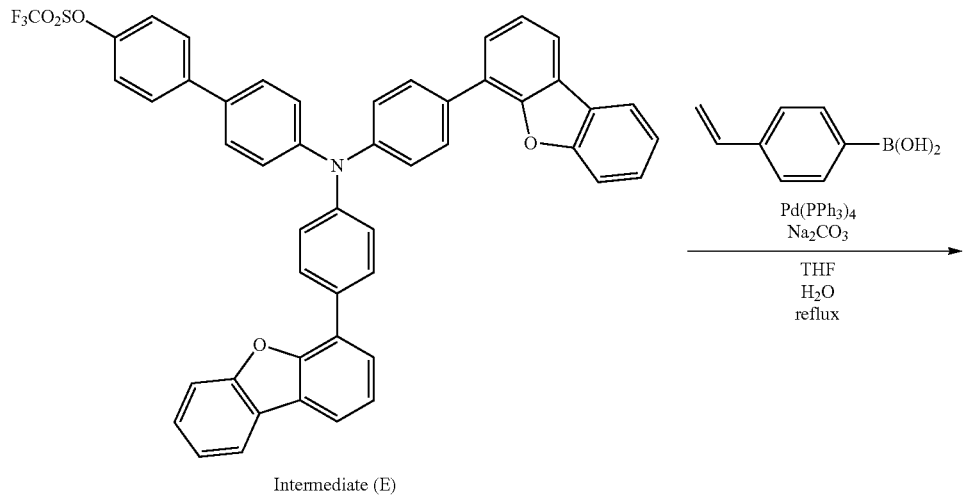

Intermediate (E)

-continued

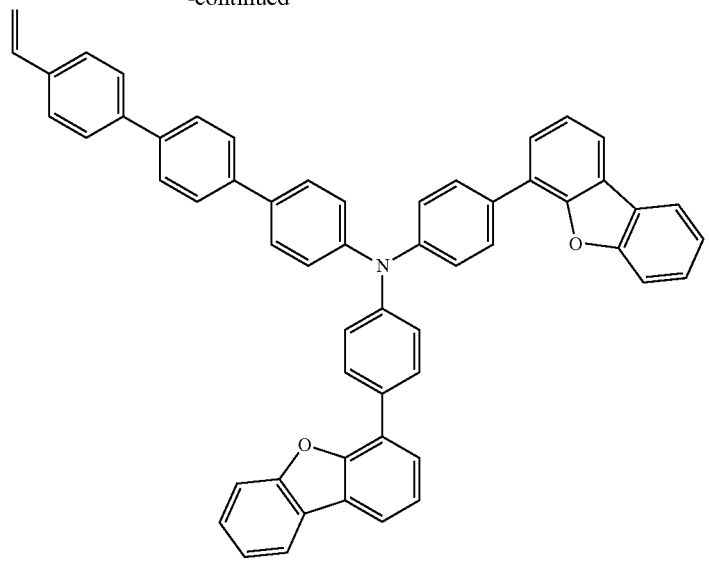

Intended product (8)

Example 9

An intended product (9) was obtained in the same manner as in Example 2, except that the intermediate (B) was used instead of the intermediate (A).

Example 10

An intended product (10) was obtained in the same manner as in Example 3, except that the intermediate (B) was used instead of the intermediate (A).

Example 11

An intended product (11) was obtained in the same manner as in Example 4, except that the intermediate (B) was used instead of the intermediate (A).

Example 12

An intended product (12) was obtained in the same manner as in Example 5, except that the intermediate (B) was used instead of the intermediate (A).

Example 13

An intended product (13) was obtained in the same manner as in Example 1, except that the intermediate (C) was used instead of the intermediate (A).

Example 14

An intended product (14) was obtained in the same manner as in Example 2, except that the intermediate (C) was used instead of the intermediate (A).

Example 15

An intended product (15) was obtained in the same manner as in Example 3, except that the intermediate (C) was used instead of the intermediate (A).

Example 16

An intended product (16) was obtained in the same manner as in Example 4, except that the intermediate (C) was used instead of the intermediate (A).

Example 17

An intended product (17) was obtained in the same manner as in Example 5, except that the intermediate (C) was used instead of the intermediate (A).

Example 18

An intended product (18) was obtained in the same manner as in Example 6, except that the intermediate (C) was used instead of the intermediate (A).

Example 19

In an argon atmosphere, in a 300 mL-three neck flask, 4.8 g (5.6 mmol) of the intermediate (D) and 0.17 g (0.28 mmol) of $PdCl_2$ (dppp) (dppp is a diphenylphosphinopropane ligand) were dissolved in 100 mL of dehydrated THF. After cooling the resulting solution at 0° C., 6.7 cc (equivalent to 6.72 mmol) of 1M vinylmagnesium bromide (a THF solution) was added dropwise, followed by stirring at room temperature for 22 hours. After dropwise addition of 200 mL of toluene and a 2N aqueous solution of hydrochloric acid, the resulting mixture was filtered, the filtrate was concentrated, and column chromatography was conducted using toluene as a solvent, whereby 2.7 g of pale yellow powder was obtained. The compound was confirmed to be the intended product (19) by NMR, MS or the like (yield 65%).

Example 20

An intermediate (F) was synthesized in the same manner as in the synthesis route of the intermediate (B), except that dibenzothiophene was used instead of dibenzofuran as the raw material.

Intermediate (F)

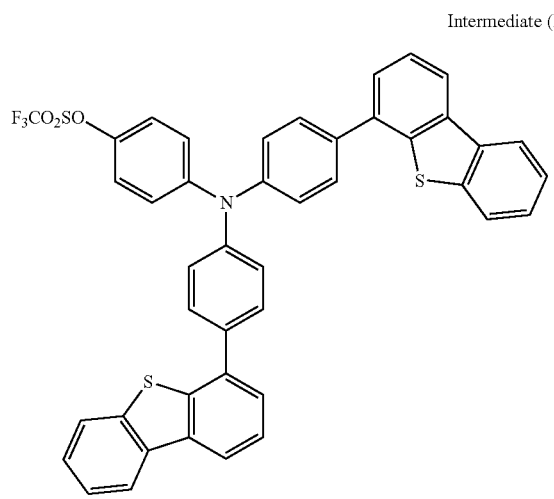

Next, an intended product (20) was obtained in the same manner as in Example 1, except that the intermediate (F) was used instead of the intermediate (A).

Example 21

An intermediate (G) was synthesized in the same manner as in the synthesis route of the intermediate (B), except that the following compound (k) was used instead of the following dibenzofuran derivative (j).

The compound (k) can be synthesized by allowing carbazole to react with 4-iodo-4'-bromo-biphenyl.

An intended product (21) was obtained in the same manner as in Example 1, except that the intermediate (G) was used instead of the intermediate (A).

(j)

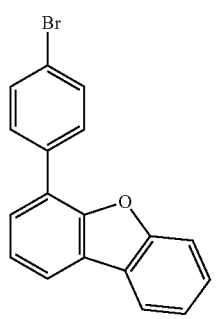

(k)

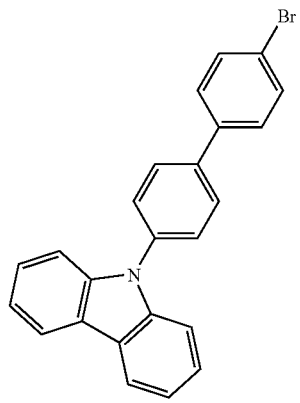

Intermediate (G)

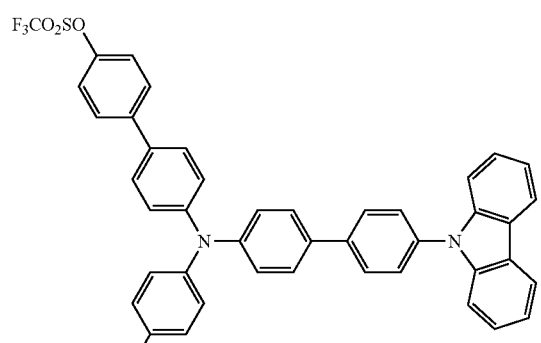

Synthesis of Intermediate (H)

Intermediate (H) was synthesized according to the following scheme, with reference to the synthesis method of the intermediate (A).

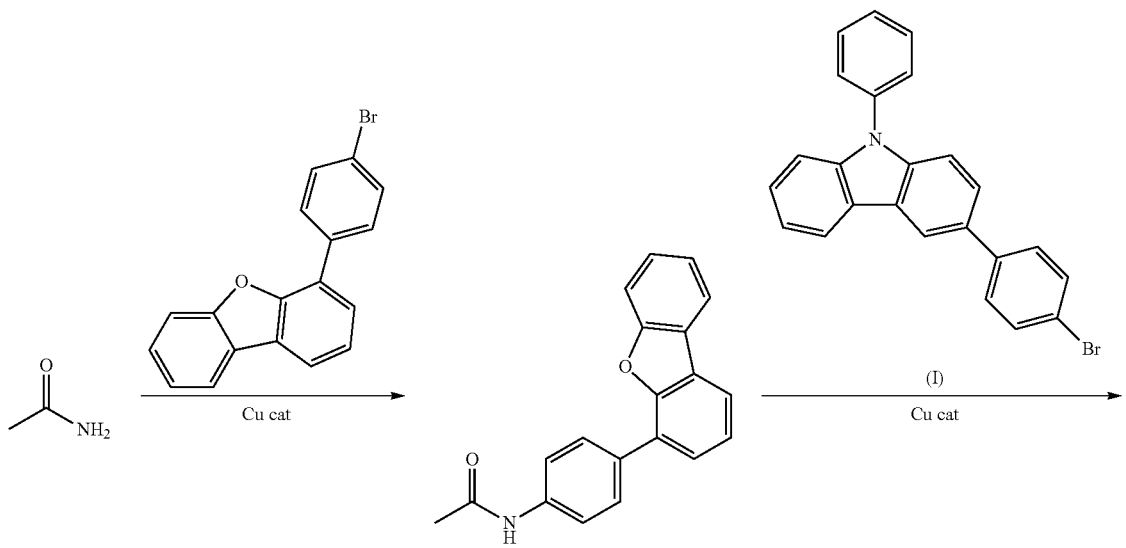

123
124
-continued
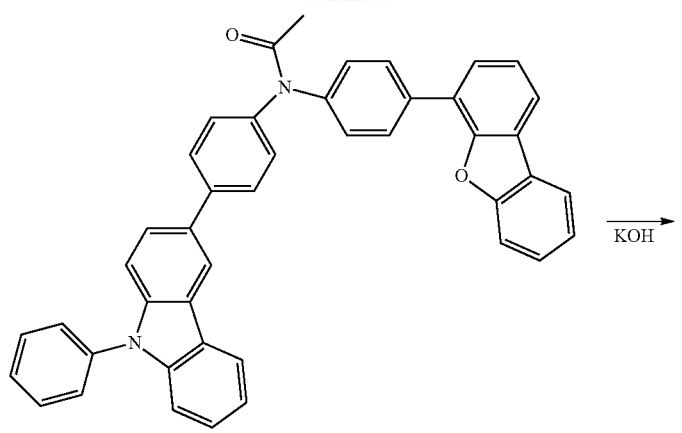
$\xrightarrow{\text{KOH}}$
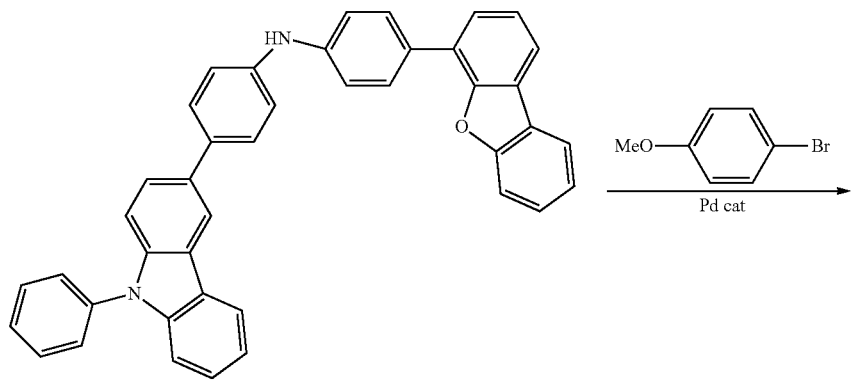
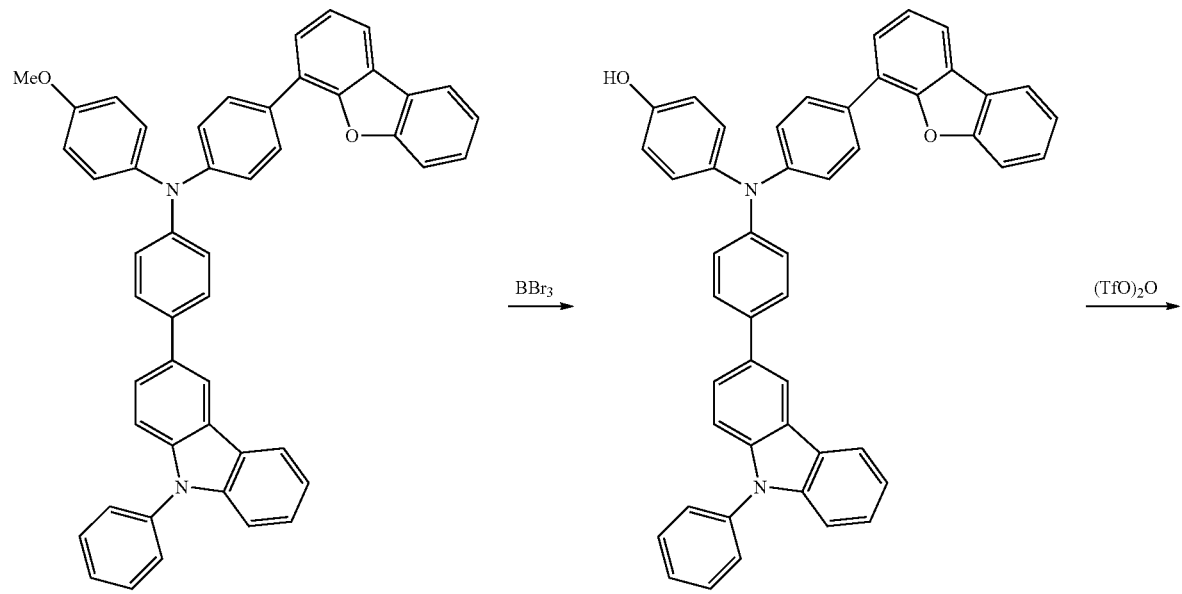

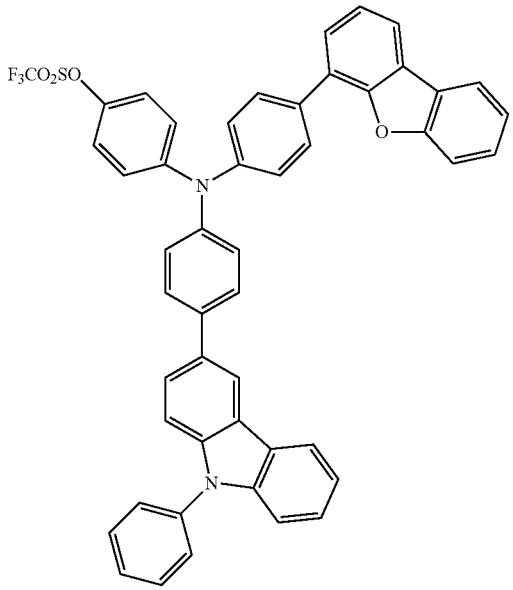

Intermediate (H)

Example 22

An intended product (22) was obtained in the same manner as in Example 1, except that the intermediate (H) was used instead of the intermediate (A).

Example 23

An intermediate (I) was synthesized in the same manner as in the synthesis route of the intermediate (H), except that the following compound (m) was used instead of the following carbazole derivative (I).

Subsequently, an intended product (23) was obtained in the same manner as in Example 1, except that the intermediate (I) was used instead of the intermediate (A).

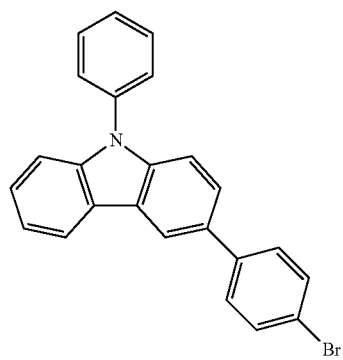

(l)

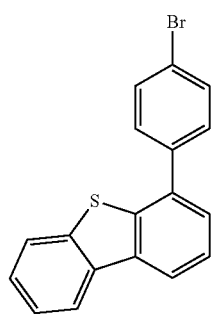

(m)

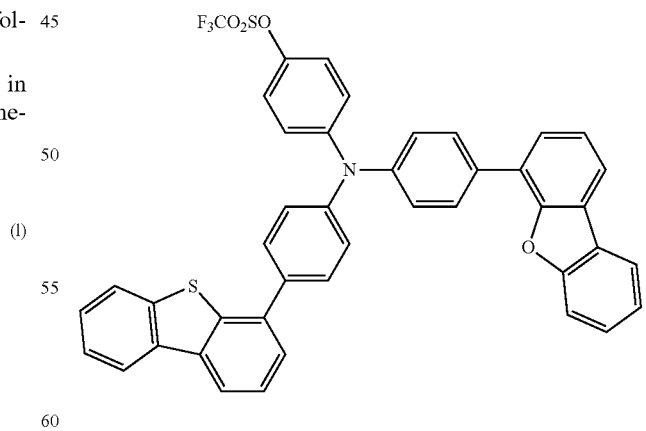

Intermediate (I)

Example 24

An intermediate (J) was synthesized in the same manner as in the synthesis route of the intermediate (H), except that the above compound (k) was used instead of the following dibenzofuran derivative (j).

An intended product (24) was used in the same manner as in Example 1, except that the intermediate (J) was used instead of the intermediate (A).

the above compound (k) was used instead of the above carbazole derivative (I).

An intended product (26) was obtained in the same manner as in Example 1, except that the intermediate (L) was used instead of the intermediate (A).

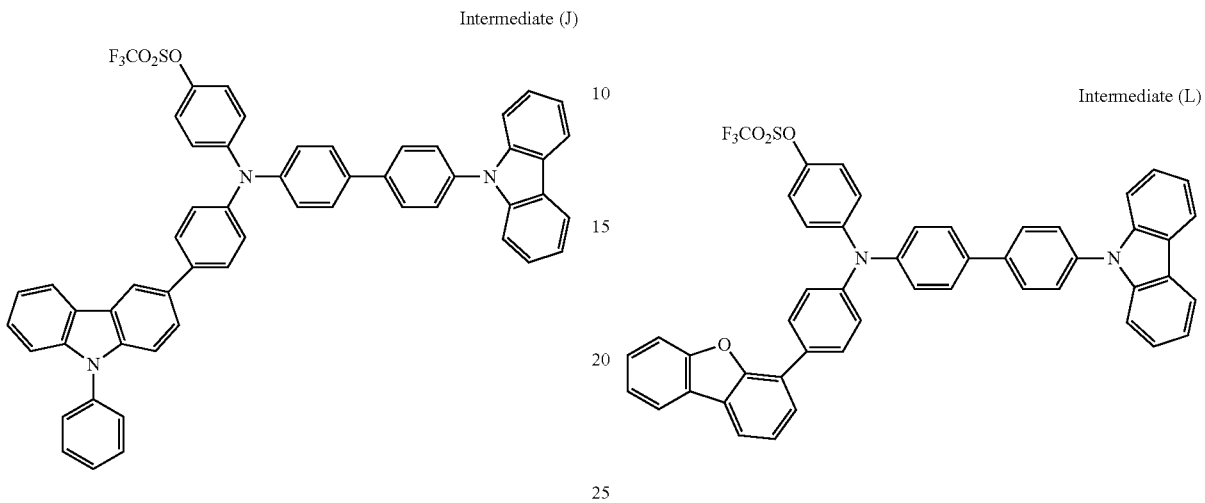

Example 25

An intermediate (K) was synthesized in the same manner as in the synthesis route of the intermediate (H), except that the above compound (m) was used instead of the following dibenzofuran derivative (j).

An intended product (25) was obtained in the same manner as in Example 1, except that the intermediate (K) was used instead of the intermediate (A).

Example 27

An intermediate (M) was synthesized in the same manner as in the synthesis route of the intermediate (H), except that the above compound (k) was used instead of the above carbazole derivative (I), and the above compound (m) was used instead of the above dibenzofuran derivative (j).

An intended product (27) was obtained in the same manner as in Example 1, except that the intermediate (M) was used instead of the intermediate (A).

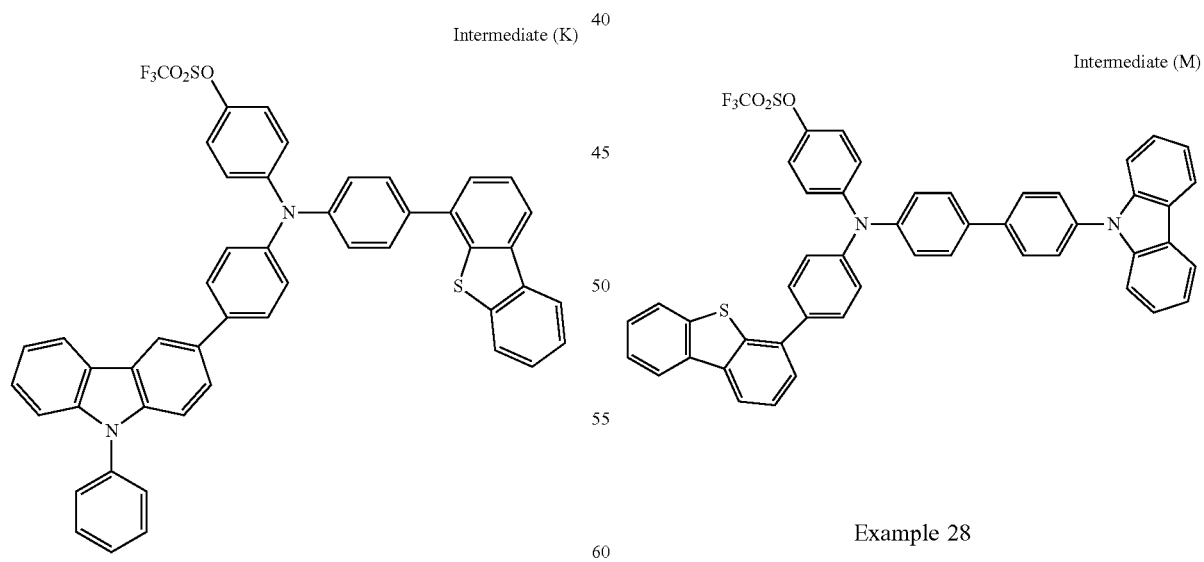

Example 26

An intermediate (L) was synthesized in the same manner as in the synthesis route of the intermediate (H), except that

Example 28

An intermediate (N) was obtained by treating the intermediate (I) obtained in Example 23 by the method which is similar to the synthesis method of the intermediate (h) in Example 6. An intended product (28) was obtained in the same manner as in Example 1, except that the intermediate (N) was used instead of the intermediate (A).

Intermediate (N)
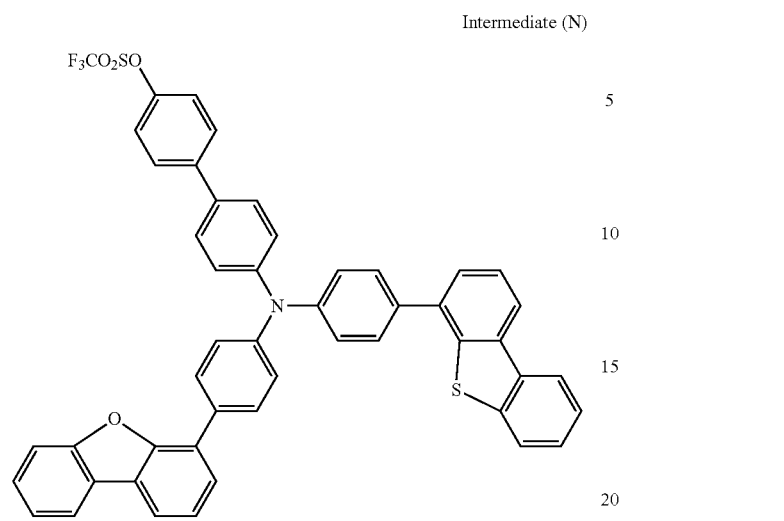
Example 29
An intended product (29) was obtained according to the following scheme.
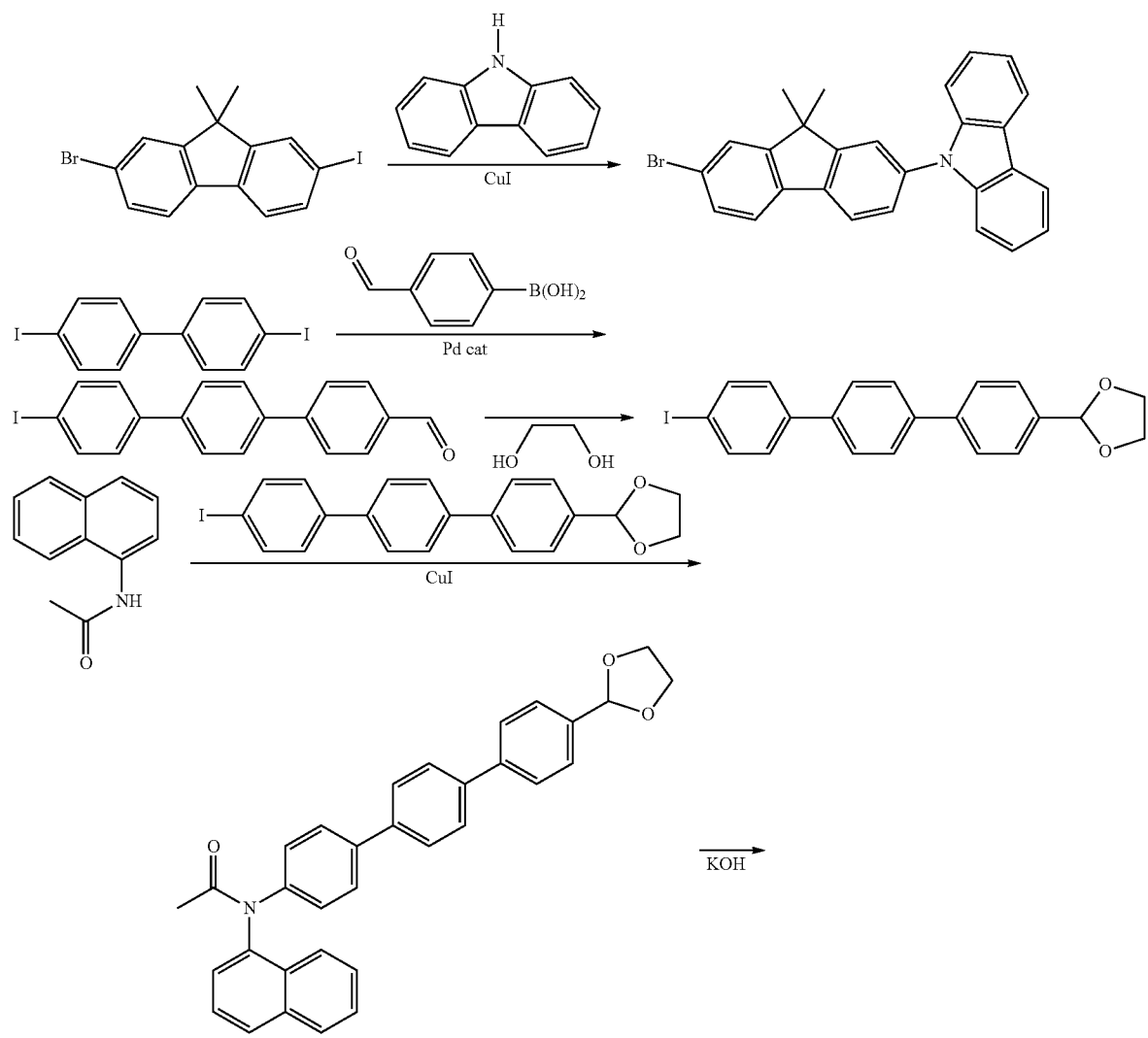

131
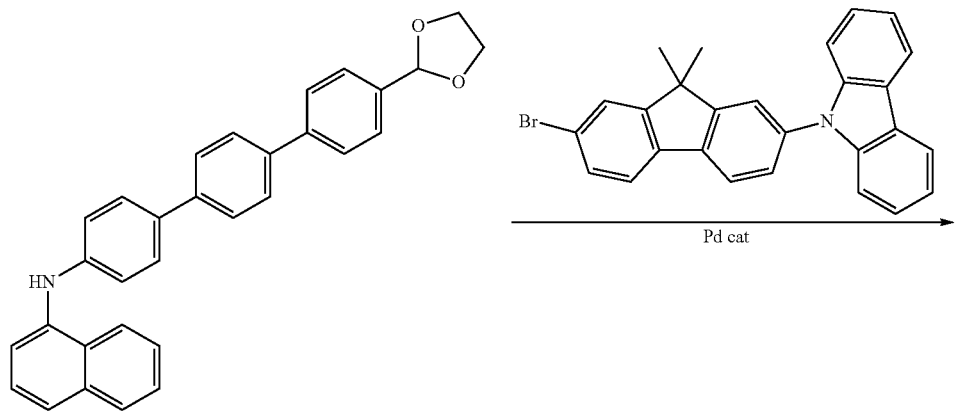
-continued
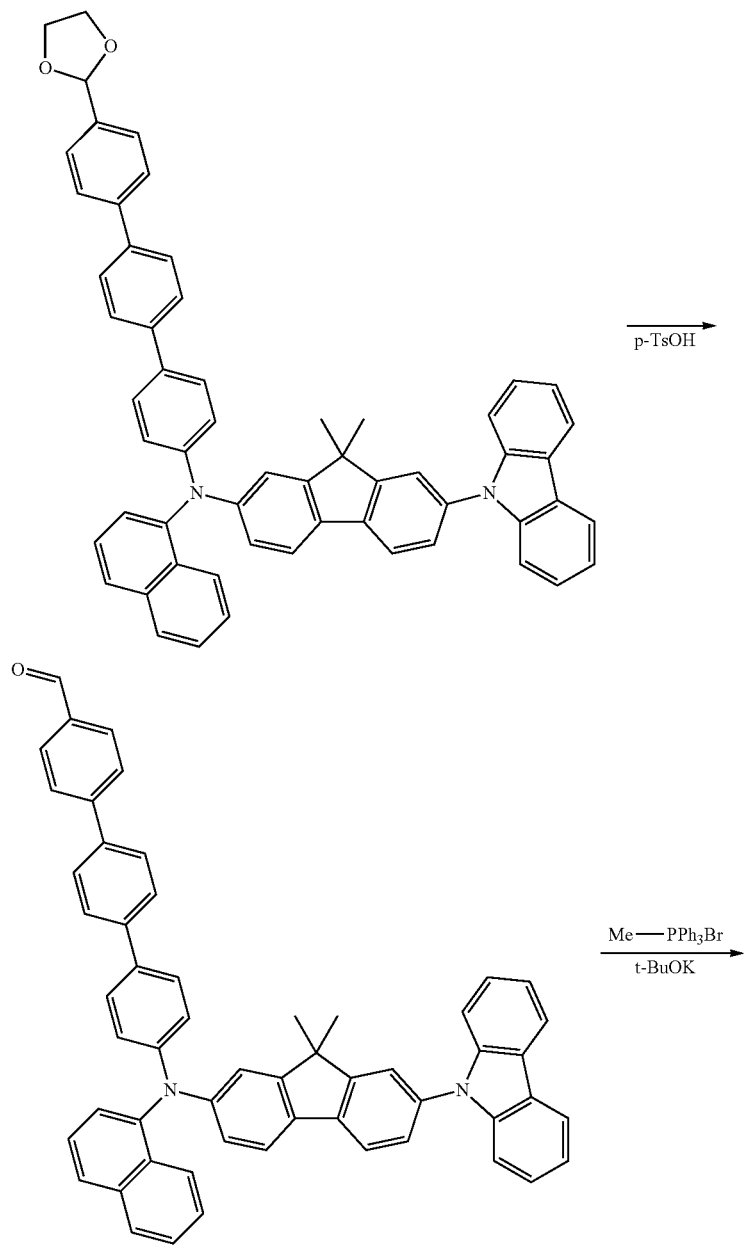

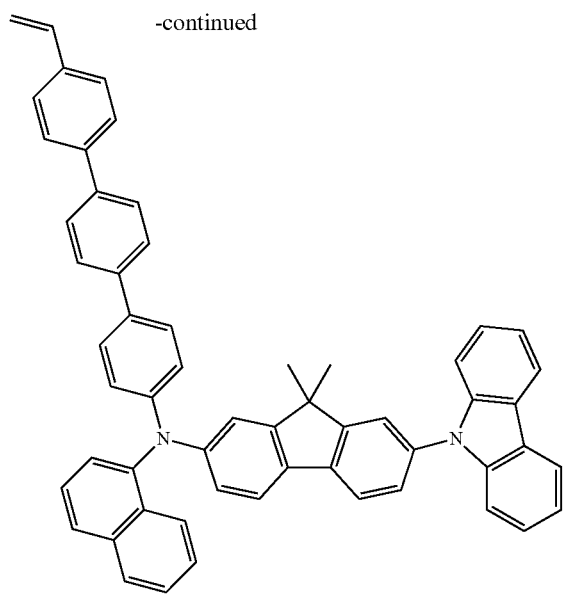
(29)
Example 30
An intended product (30) was obtained according to the following scheme.
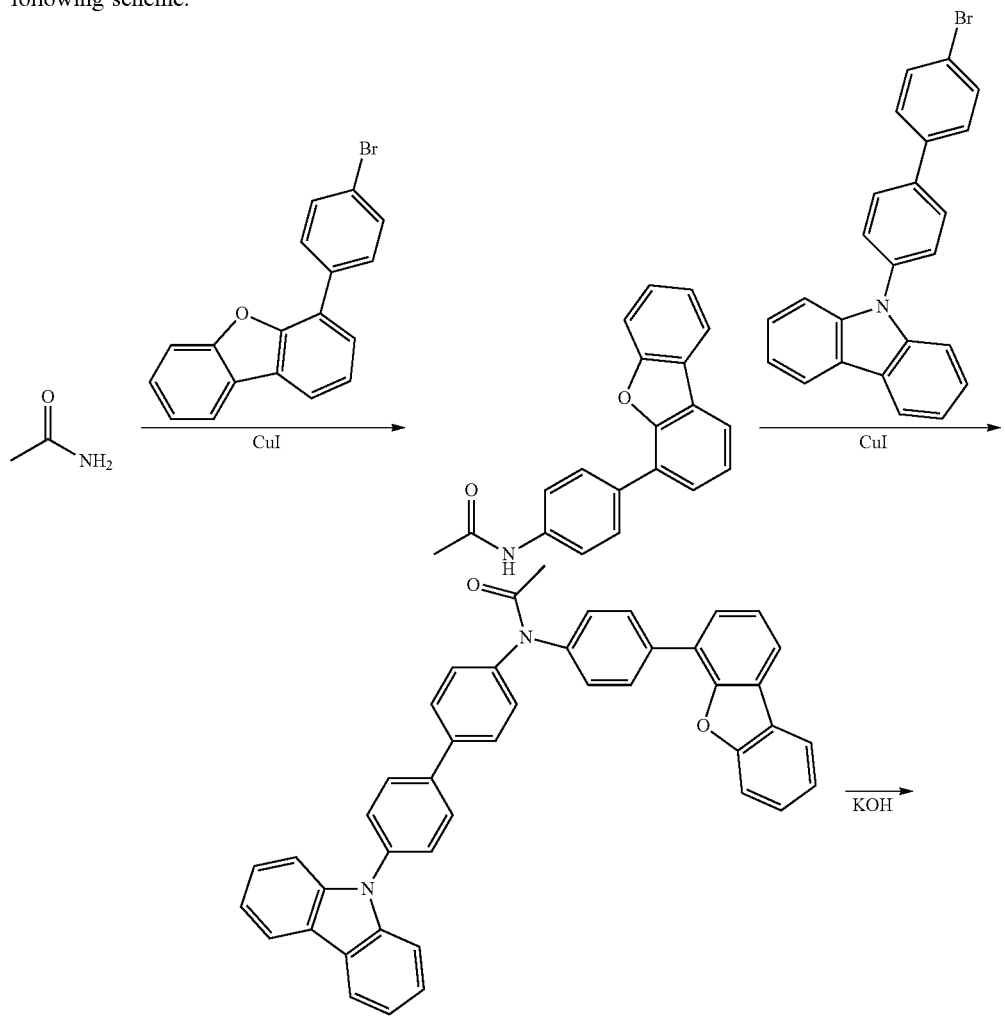

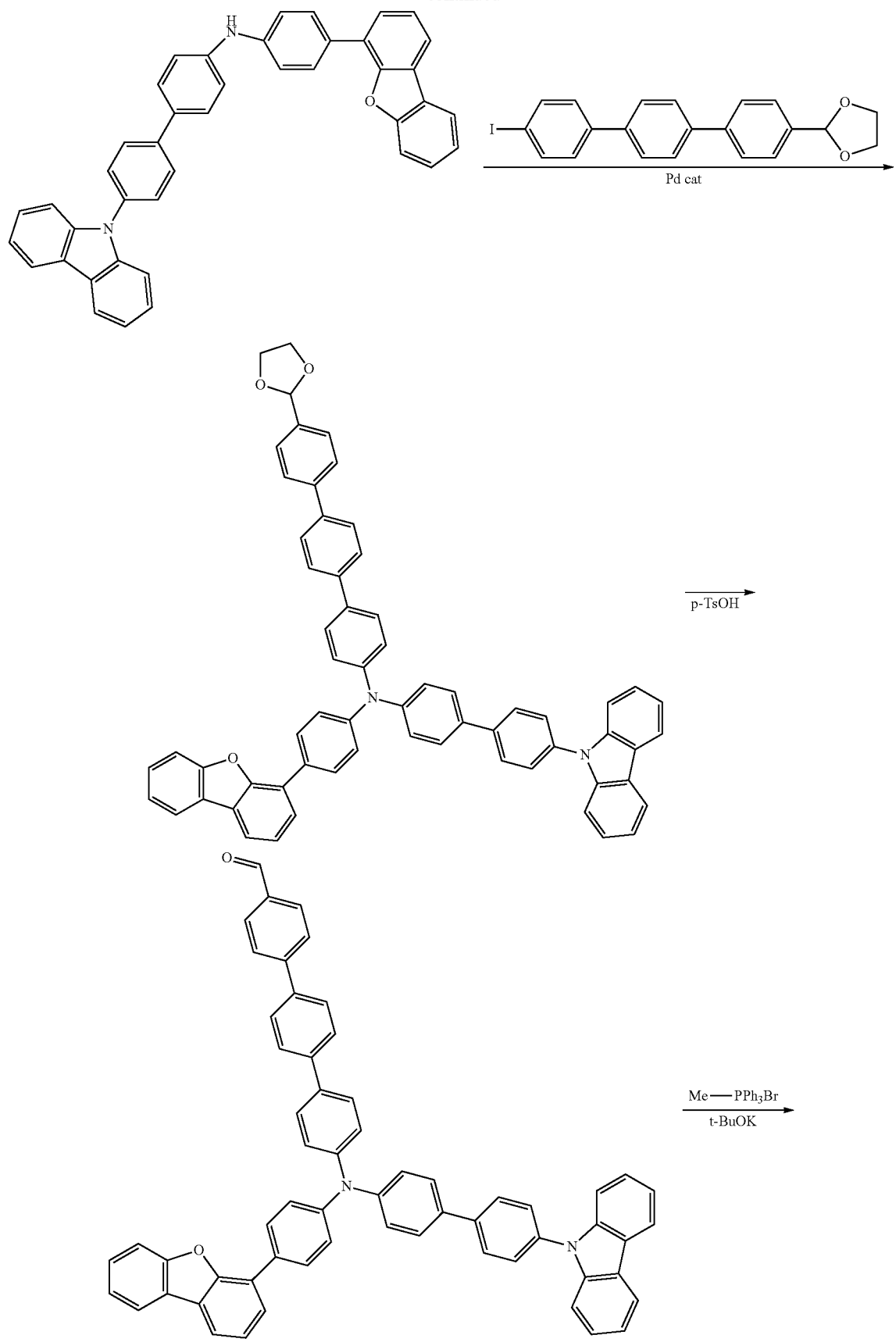

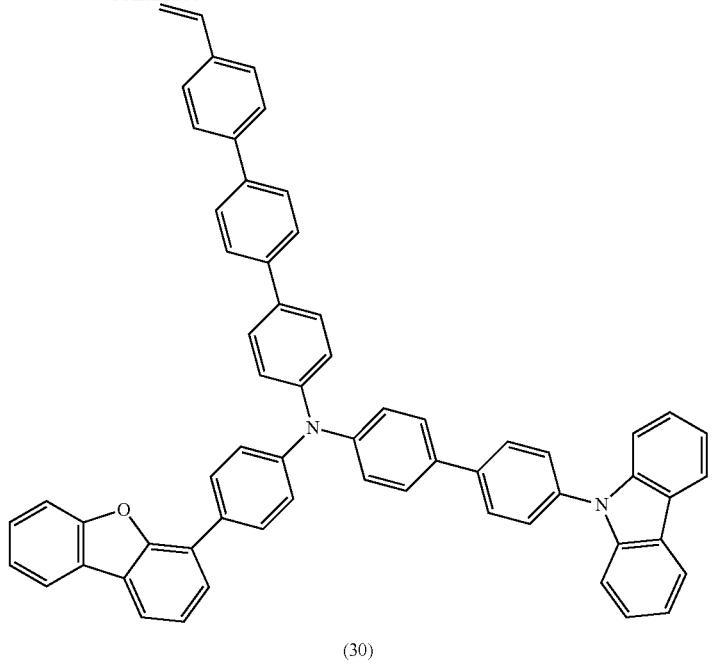
(30)
Example 31
An intended product (31) was obtained according to the following scheme.
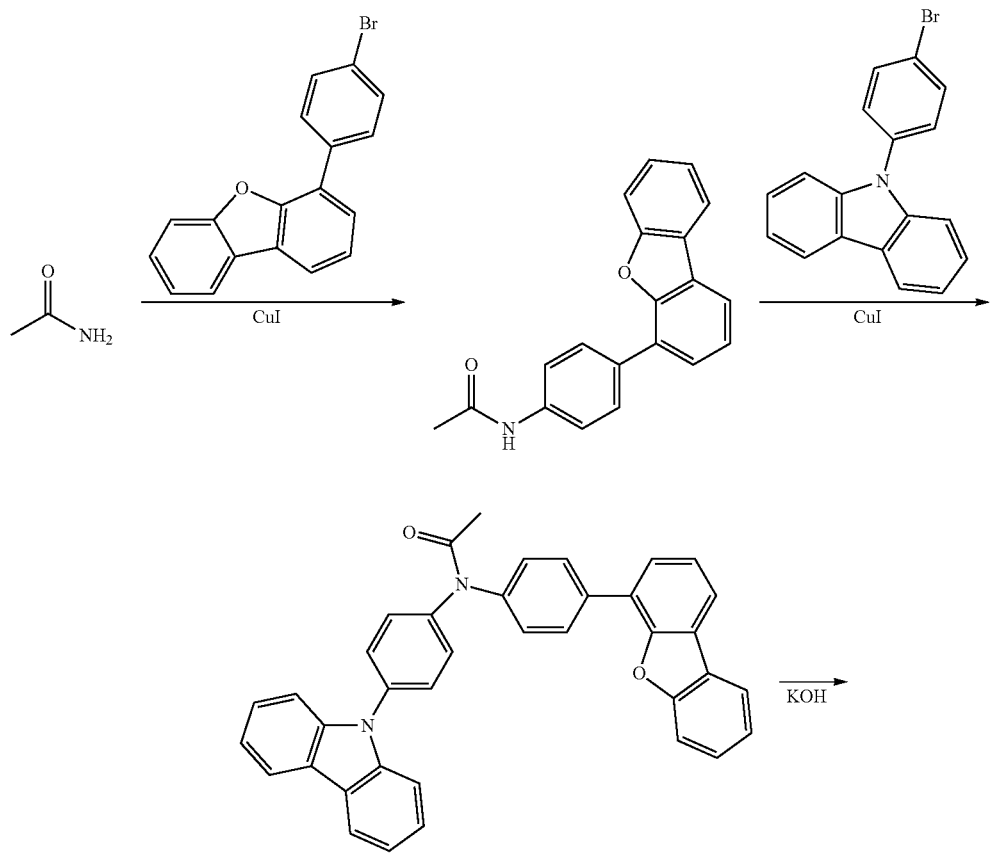

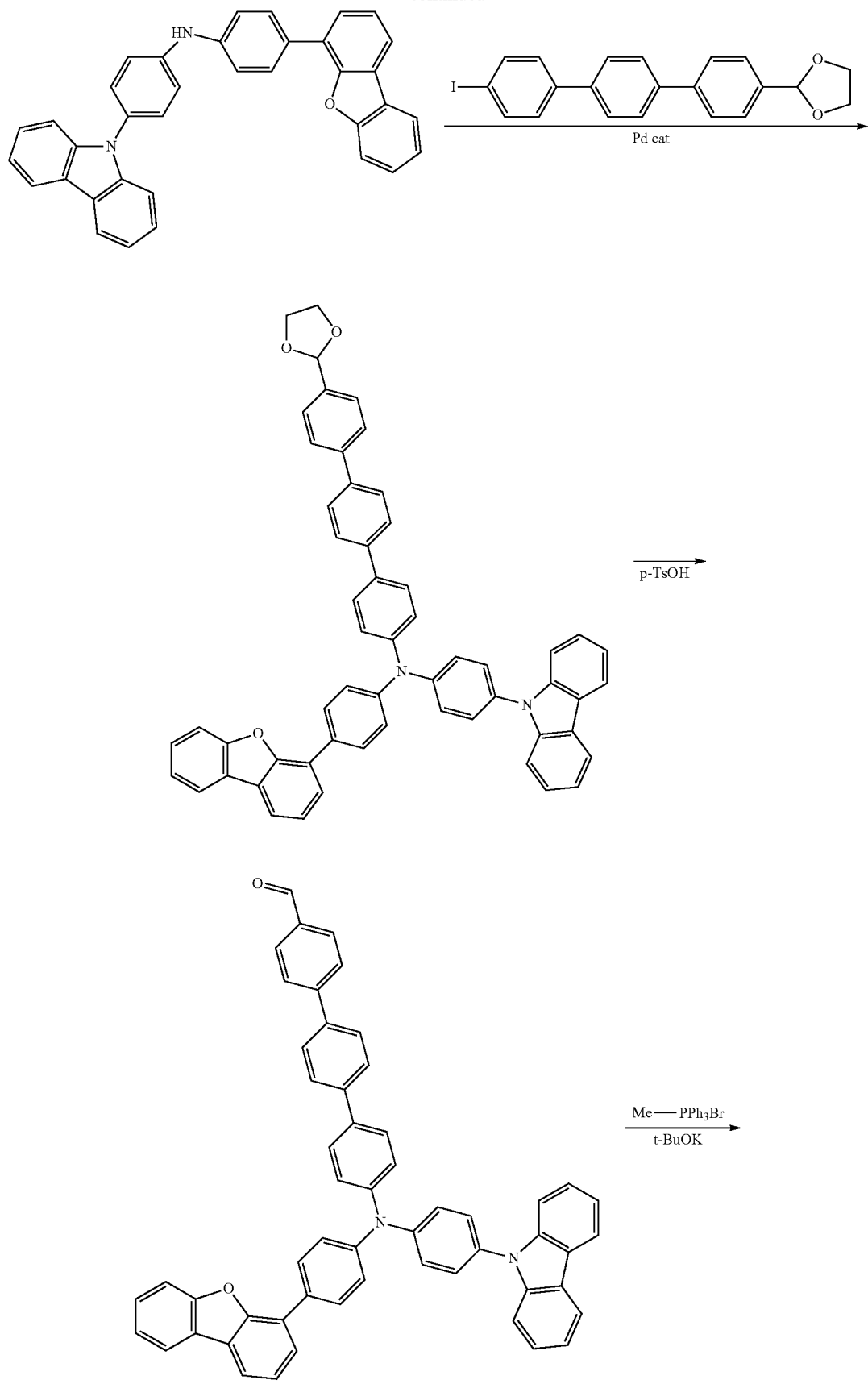

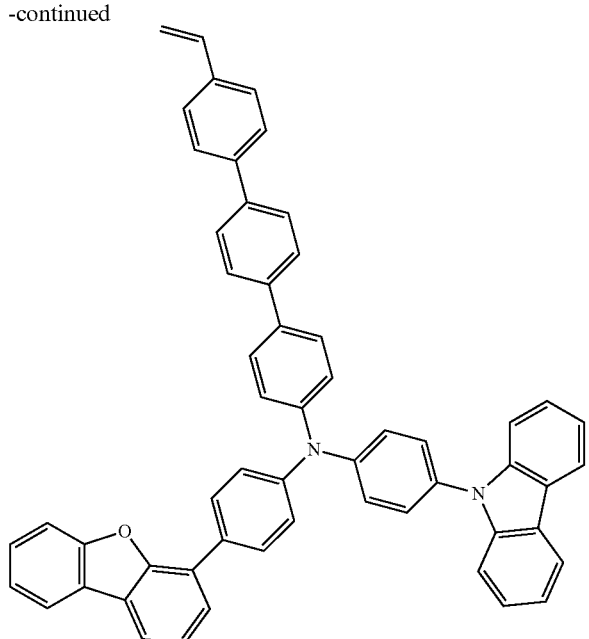
(31)
Example 32
An intended product (32) was obtained according to the following scheme.
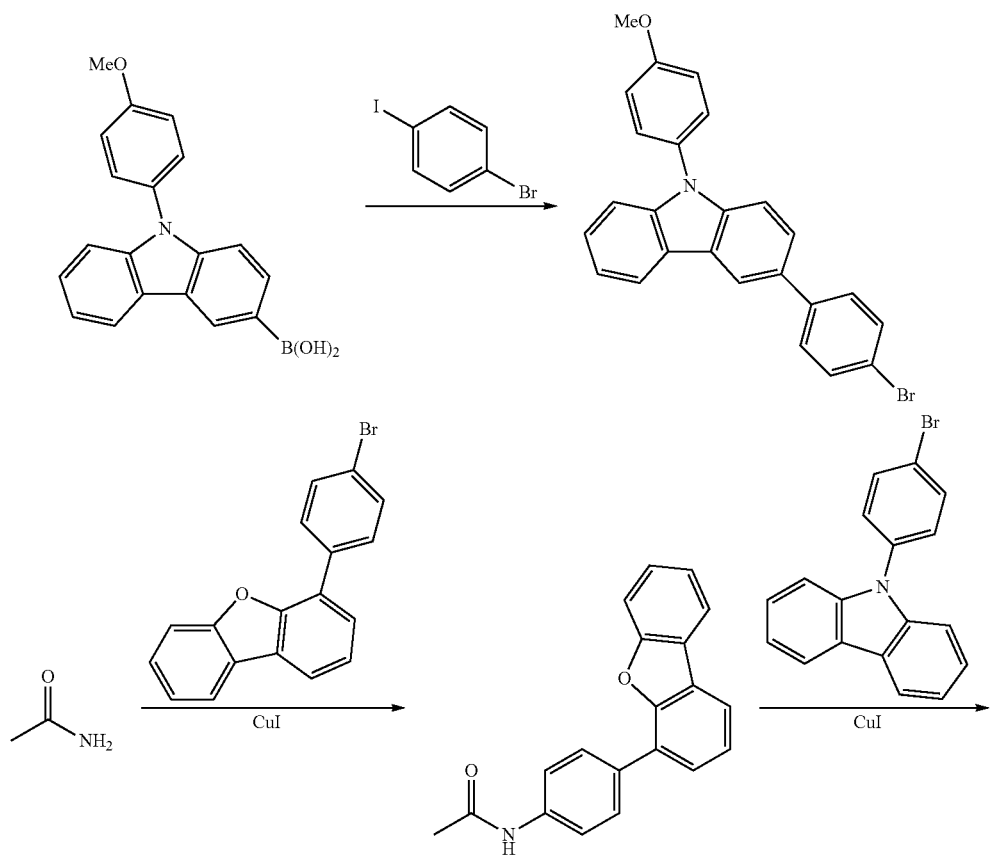

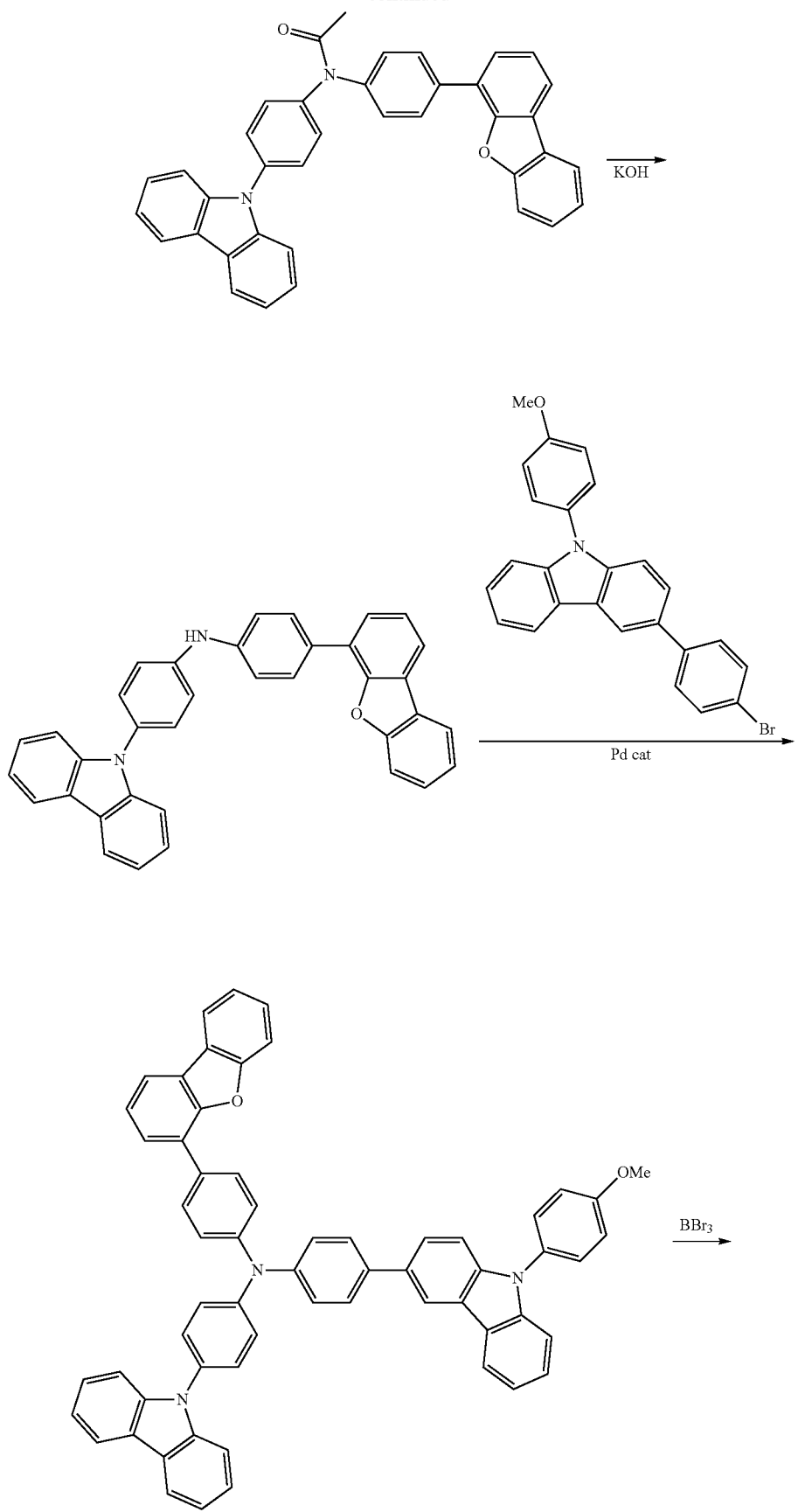

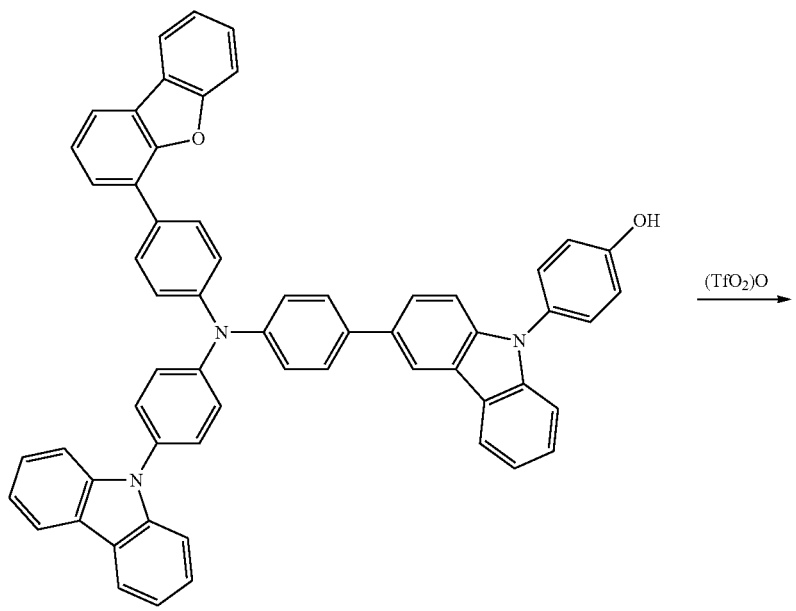
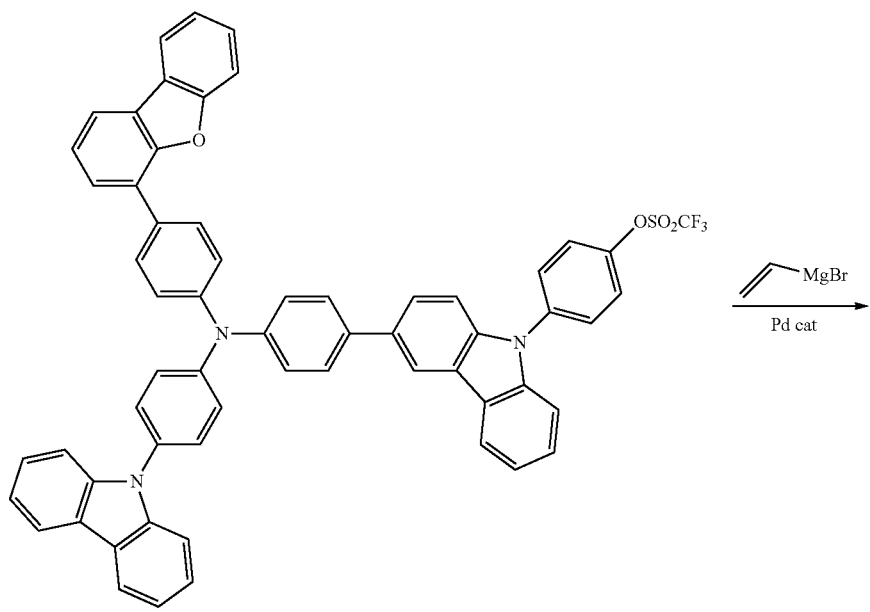

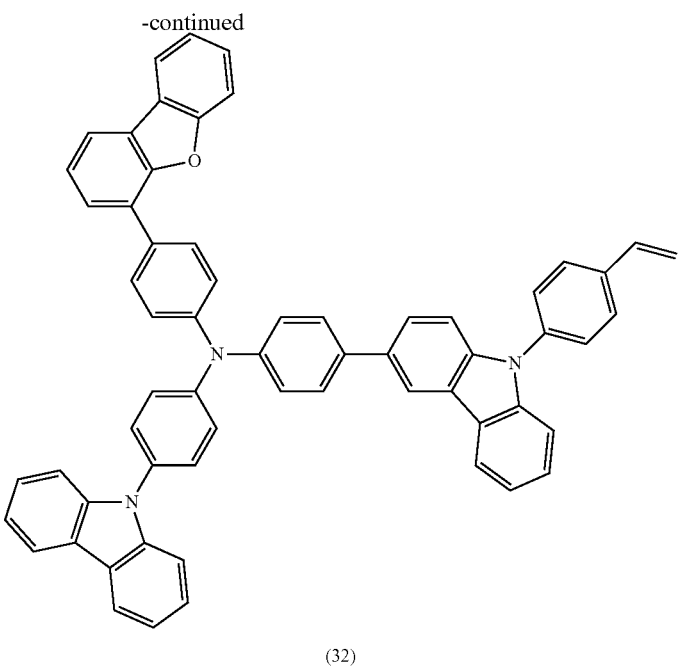

(32)

Synthesis of Polymer

Example 33

Cationic Polymerization (1) Preparation of Trifluoromethanesulfonic Acid Solution In a nitrogen stream, commercially-available trifluoromethanesulfonic acid (25 g, 0.167 mol, molecular weight: 150.08, specific gravity: 1.70) was added to dehydrated methylene chloride, and the concentration thereof was adjusted to 1.0 M (the total amount of the solution: 167 mL). Trifluoromethanesulfonic acid was not mixed completely homogenously with methylene chloride. Therefore, the resulting solution was sufficiently stirred to allow the trifluoromethanesulfonic acid to be suspended in the solution, and the resulting suspension was used in the subsequent reaction.

(2) Polymerization of Compound (1) in Example 1 (Cationic Polymerization)

A 500 mL-three neck flask provided with a reflux tube was fully replaced by nitrogen. In a nitrogen stream, the flask was charged with the monomer compound (1) obtained in Example 1 (1.2 g, 1.44 mmol) and dehydrated methylene chloride (200 mL), and the resultant was stirred under reflux for 1 hour until the monomer compound was completely dissolved. After cooling to room temperature, 4.32 mL (4.32 mmol) of the suspension of trifluoromethanesulfonic acid prepared in (1) above was added. The solution was stirred at room temperature for 4 hours, whereby a polymerization reaction was conducted.

(3) Post Treatment after the Reaction

The reaction liquid was poured to a large amount of methanol (800 mL) with stirring to allow solids (polymer) to be deposited. The solids were separated by filtration. Subsequently, the solids were dissolved in toluene (100 mL) at room temperature, and the resulting solution was poured to a large amount of methanol (800 mL) with stirring, while being filtered by means of filter paper, whereby the solids (polymer) were deposited. Further, methanol was separated by filtration, followed by sufficient drying, thereby to obtain 0.80 g of the polymer. The polymer obtained had a number average molecular weight of 10,000.

Example 34

Radical Polymerization

A 500 mL-three neck flask provided with a reflux tube was fully replaced by nitrogen. In a nitrogen stream, the flask was charged with the monomer compound (2) obtained in Example 2 (1.2 g, 1.44 mmol) and dehydrated methylene chloride (200 mL), and the resultant was stirred under reflux for 1 hour until the monomer compound was completely dissolved. The resultant was cooled to room temperature. Then, a solution obtained by dissolving 20 mg of benzoyl peroxide (BPO) as a radical polymerization initiator in 15 mL of dehydrated methylene chloride was added at room temperature. Subsequently, a polymerization reaction was conducted at 70° C. for 48 hours in nitrogen.

After the completion of the reaction, re-precipitation was conducted three times by using toluene as a good solvent and methanol as a poor solvent, whereby 0.91 g of a polymer was obtained. The resulting polymer had a number average molecular weight of 13,000.

Examples 37 to 39, 43 and 46 to 59

In each example, a polymer was synthesized in the same manner as in Example 33 (cationic polymerization) using the monomer obtained in Examples 5, 7, 8, 13, 17, and 19 to 31, respectively.

Examples 35, 36, 40 to 42, 44, 45 and 60

In each example, a polymer was synthesized in the same manner as in Example 34 (radical polymerization) using the monomer obtained in Examples 3, 4, 9 to 11, 14, 16 and 32 respectively.

The above-mentioned monomers and polymers obtained therefrom and the polymerization method are summarized in Table 1.

TABLE 1-1

| Example | Monomer | Monomer No. | Polymerization Example | Polymerization method | Device fabrication, Evaluation Example |
|---|---|---|---|---|---|
| 1 | 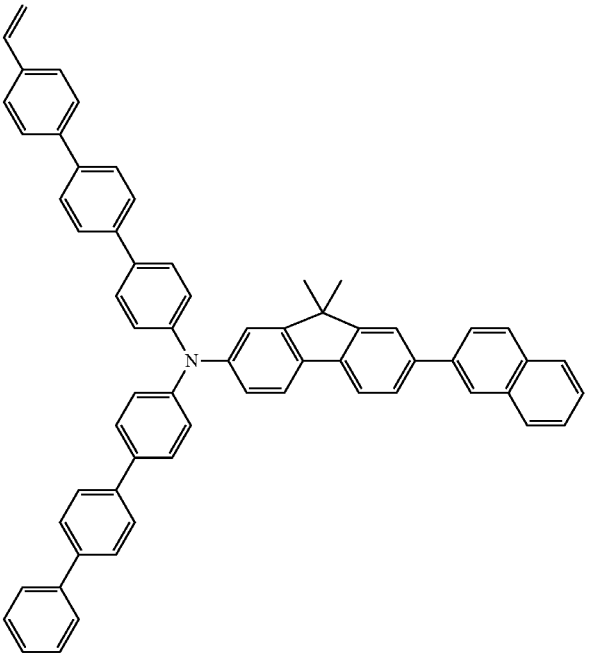 | (1) | 33 | Cationic | 61 |
| 2 | 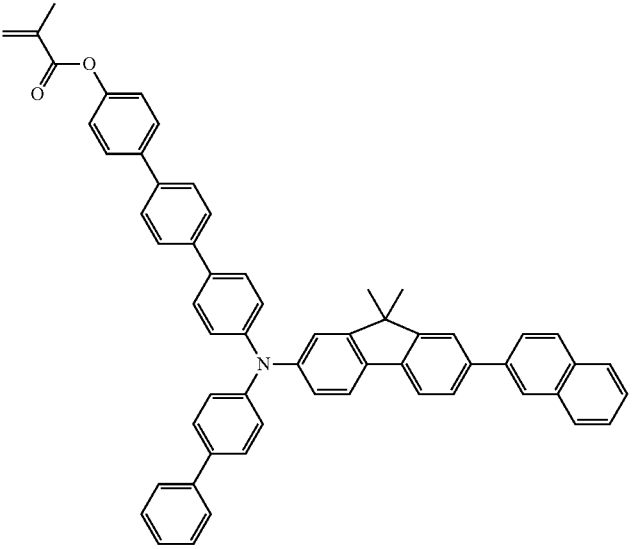 | (2) | 34 | Radical | 62 |

TABLE 1-1-continued

| Example | Monomer | Monomer No. | Polymerization Example | Polymerization method | Device fabrication, Evaluation Example |
|---|---|---|---|---|---|
| 3 | (structure) | (3) | 35 | Radical | 63 |
| 4 | (structure) | (4) | 36 | Radical | 64 |

TABLE 1-1-continued
| Example | Monomer | Monomer No. | Polymerization Example | Polymerization method | Device fabrication, Evaluation Example |
|---|---|---|---|---|---|
| 5 | 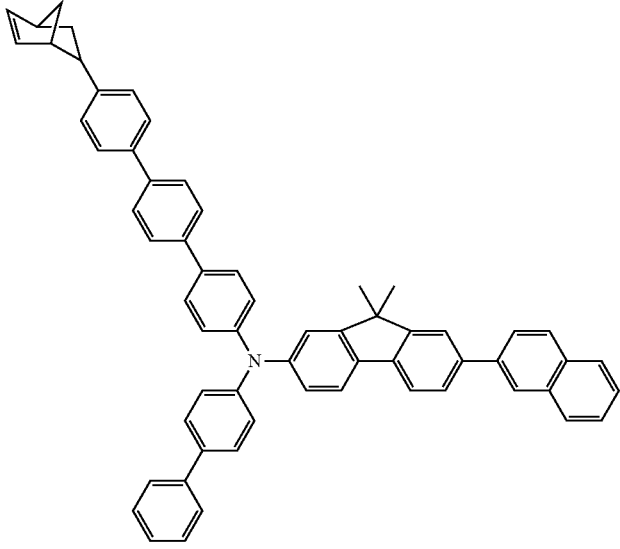 | (5) | 37 | Cationic | 65 |
| 6 | 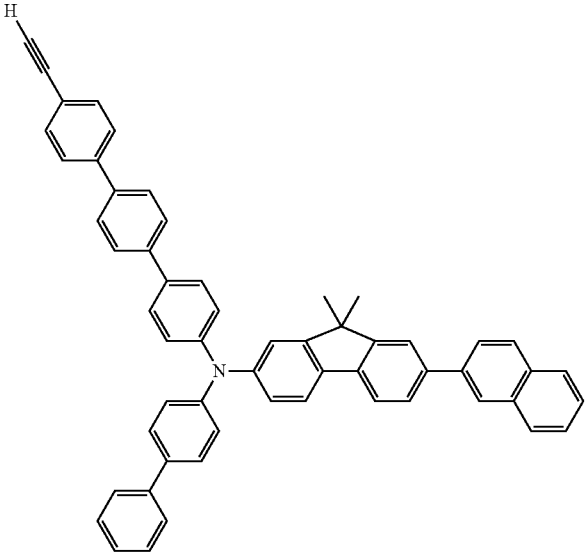 | (6) | — | — | — |

TABLE 1-1-continued

| Example | Monomer | Monomer No. | Polymerization Example | Polymerization method | Device fabrication, Evaluation Example |
|---|---|---|---|---|---|
| 7 | (structure) | (7) | 38 | Cationic | 66 |
| 8 | (structure) | (8) | 39 | Cationic | 67 |

TABLE 1-1-continued

| Example | Monomer | Monomer No. | Polymerization Example | Polymerization method | Device fabrication, Evaluation Example |
|---|---|---|---|---|---|
| 9 | [structure] | (9) | 40 | Radical | 68 |
| 10 | [structure] | (10) | 41 | Radical | 69 |

TABLE 1-1-continued

| Example | Monomer | Monomer No. | Polymerization Example | Polymerization method | Device fabrication, Evaluation Example |
|---------|---------|-------------|------------------------|-----------------------|----------------------------------------|
| 11 | *(structure)* | (11) | 42 | Radical | 70 |
| 12 | *(structure)* | (12) | — | — | — |

TABLE 1-1-continued

| Example | Monomer | Monomer No. | Polymerization Example | Polymerization method | Device fabrication, Evaluation Example |
|---|---|---|---|---|---|
| 13 | | (13) | 43 | Cationic | 71 |
| 14 | | (14) | 44 | Radical | 72 |

TABLE 1-1-continued
| Example | Monomer | Monomer No. | Polymerization Example | Polymerization method | Device fabrication, Evaluation Example |
|---|---|---|---|---|---|
| 15 | 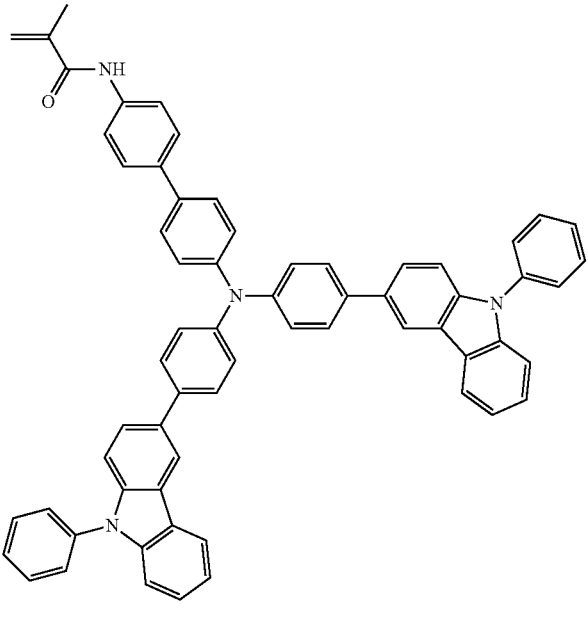 | (15) | — | — | — |
| 16 | 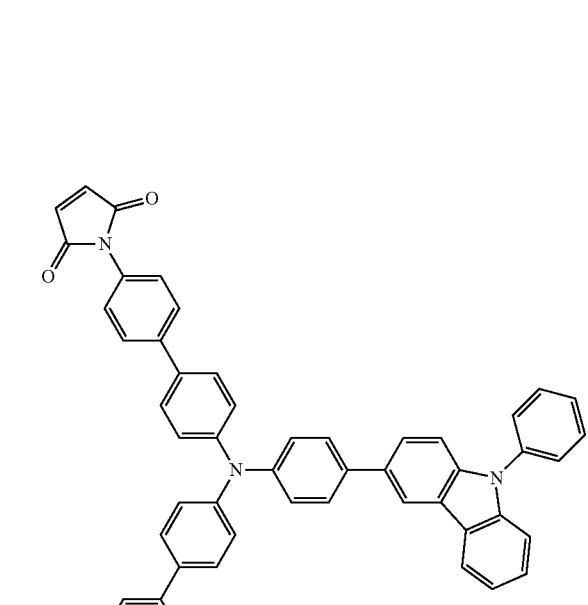 | (16) | 45 | Radical | 73 |

TABLE 1-1-continued

| Example | Monomer | Monomer No. | Polymerization Example | Polymerization method | Device fabrication, Evaluation Example |
|---------|---------|-------------|------------------------|-----------------------|----------------------------------------|
| 17 | *(structure)* | (17) | 46 | Cationic | 74 |
| 18 | *(structure)* | (18) | — | — | — |

TABLE 1-1-continued

| Example | Monomer | Monomer No. | Polymerization Example | Polymerization method | Device fabrication, Evaluation Example |
|---|---|---|---|---|---|
| 19 | | (19) | 47 | Cationic | 75 |
| 20 | | (20) | 48 | Cationic | 76 |
| 21 | | (21) | 49 | Cationic | 77 |

TABLE 1-1-continued
| Example | Monomer | Monomer No. | Polymerization Example | Polymerization method | Device fabrication, Evaluation Example |
|---------|---------|-------------|------------------------|-----------------------|----------------------------------------|
| 22 | 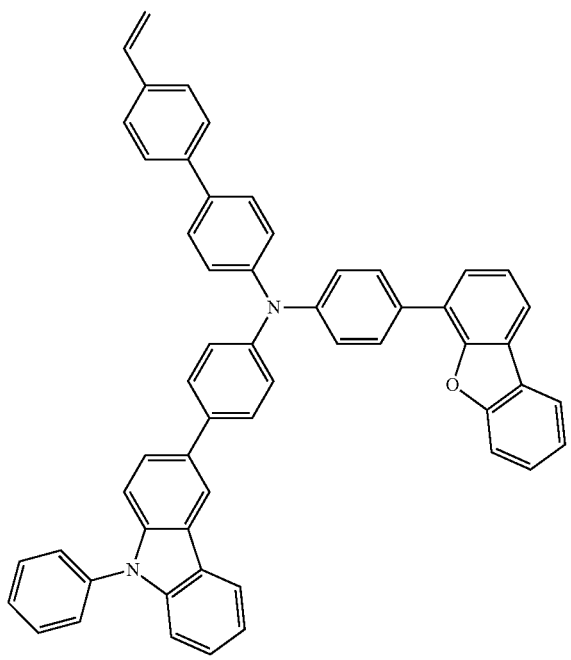 | (22) | 50 | Cationic | 78 |
| 23 | 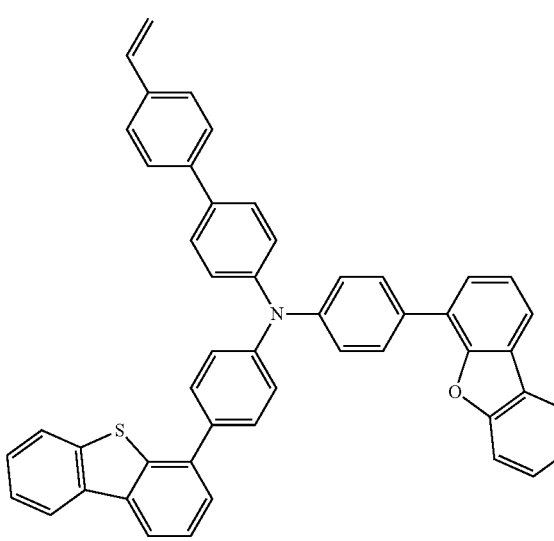 | (23) | 51 | Cationic | 79 |

TABLE 1-1-continued

| Example | Monomer | Monomer No. | Polymerization Example | Polymerization method | Device fabrication, Evaluation Example |
|---|---|---|---|---|---|
| 24 | | (24) | 52 | Cationic | 80 |
| 25 | | (25) | 53 | Cationic | 81 |

TABLE 1-1-continued
| Example | Monomer | Monomer No. | Polymerization Example | Polymerization method | Device fabrication, Evaluation Example |
|---|---|---|---|---|---|
| 26 | 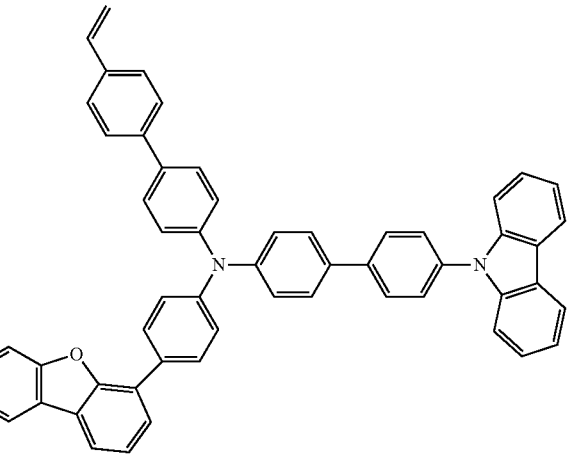 | (26) | 54 | Cationic | 82 |
| 27 | 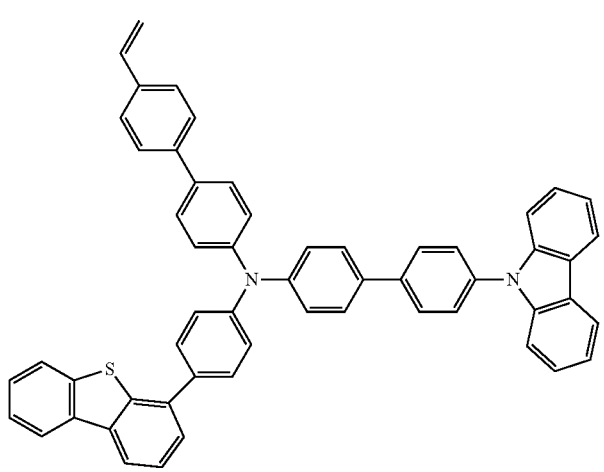 [SMILES: C=Cc1ccc(-c2ccc(N(c3ccc(-c4ccc(-n5c6ccccc6c6ccccc65)cc4)cc3)c3ccc(-c4cccc5c4oc4ccccc45)cc3)cc2)cc1] | (27) | 55 | Cationic | 83 |
| 28 | 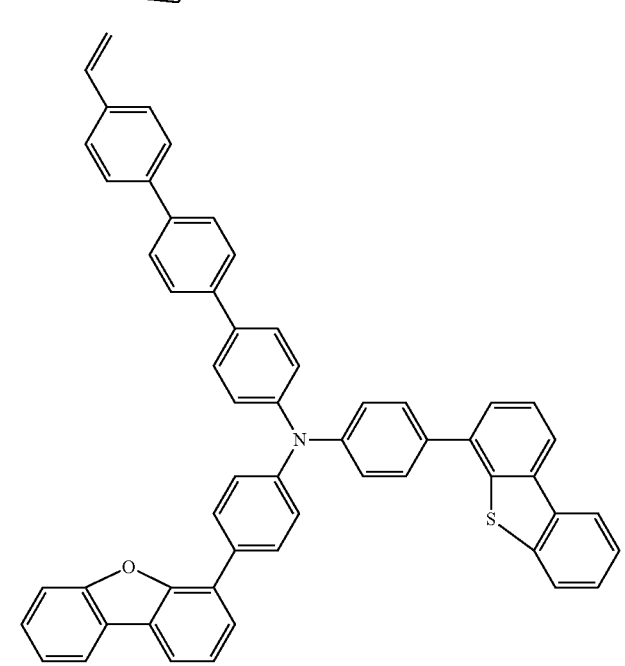 | (28) | 56 | Cationic | 84 |

TABLE 1-1-continued
| Example | Monomer | Monomer No. | Polymerization Example | Polymerization method | Device fabrication, Evaluation Example |
|---|---|---|---|---|---|
| 29 | 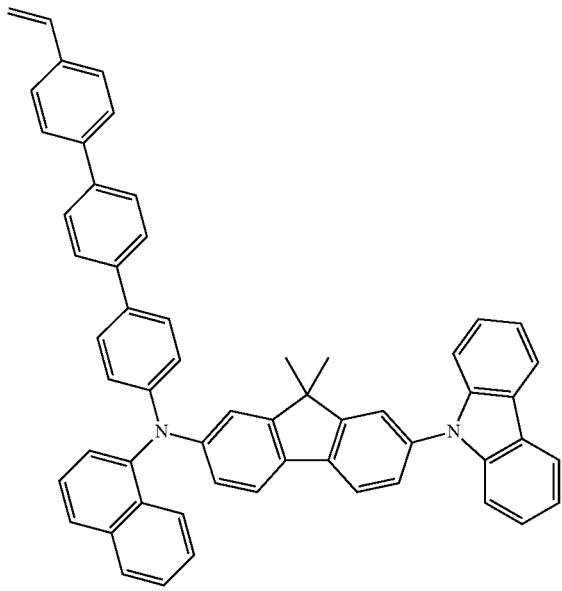 [SMILES: C=Cc1ccc(-c2ccc(-c3ccc(N(c4ccc5c(c4)C(C)(C)c4cc(-n6c7ccccc7c7ccccc76)ccc4-5)c4cccc5ccccc45)cc3)cc2)cc1] | (29) | 57 | Cationic | 85 |
| 30 | 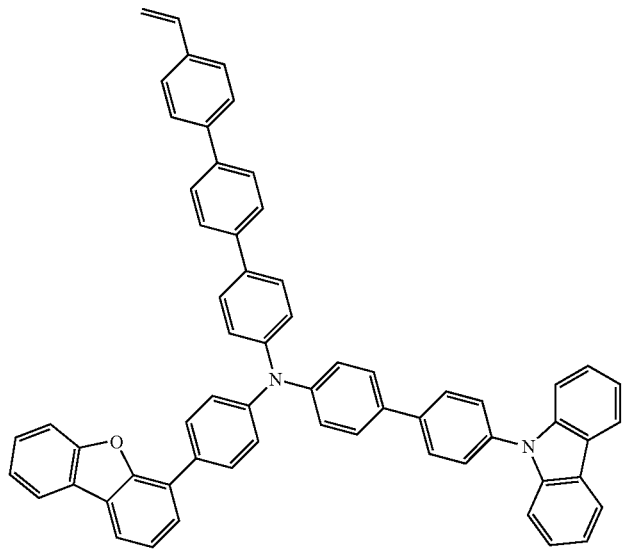 [SMILES: C=Cc1ccc(-c2ccc(-c3ccc(N(c4ccc(-c5ccc(-n6c7ccccc7c7ccccc76)cc5)cc4)c4ccc(-c5cccc6c5oc5ccccc56)cc4)cc3)cc2)cc1] | (30) | 58 | Cationic | 86 |

TABLE 1-1-continued

| Example | Monomer | Monomer No. | Polymerization Example | Polymerization method | Device fabrication, Evaluation Example |
|---|---|---|---|---|---|
| 31 | 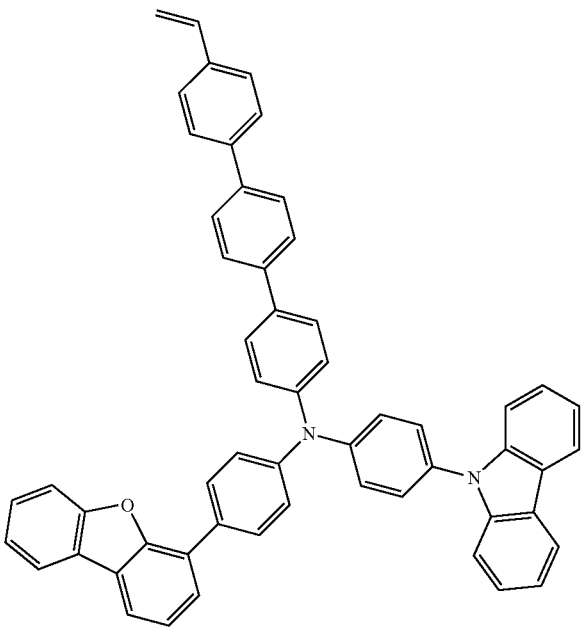 [SMILES: C=Cc1ccc(-c2ccc(-c3ccc(N(c4ccc(-c5cccc6c5oc5ccccc56)cc4)c4ccc(-n5c6ccccc6c6ccccc65)cc4)cc3)cc2)cc1] | (31) | 59 | Cationic | 87 |
| 32 | 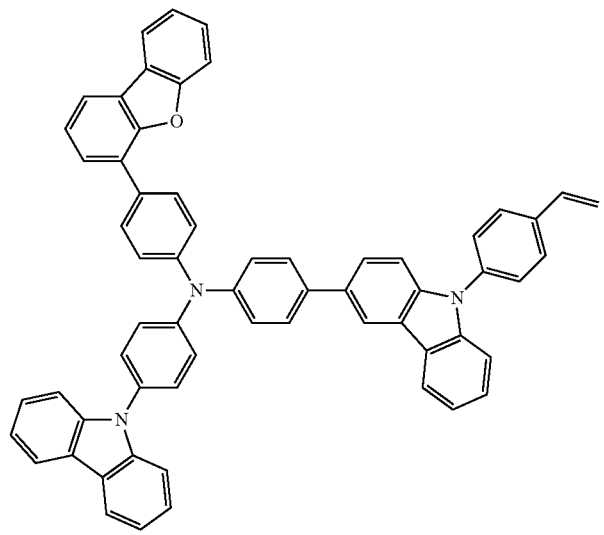 [SMILES: C=Cc1ccc(-n2c3ccccc3c3cc(-c4ccc(N(c5ccc(-c6cccc7c6oc6ccccc67)cc5)c5ccc(-n6c7ccccc7c7ccccc76)cc5)cc4)ccc32)cc1] | (32) | 60 | Radical | 88 |

Example 61

Fabrication and Evaluation of Organic EL Device

A glass substrate (GEOMATEC CO., LTD.) of 25 mm×75 mm×1.1 mm thick with an ITO transparent electrode was subjected to ultrasonic cleaning with isopropyl alcohol for 5 minutes, and cleaned with ultraviolet rays and ozone for 30 minutes.

On the cleaned glass substrate provided with a transparent electrode, a mixture of polyethylene dioxythiophene and polystyrene sulfonic acid (PEDOT:PSS) which is used in the hole-injecting layer was formed into a 10 nm-thick film by the spin coating method (PSS is an acceptor).

Subsequently, as a hole-transporting polymer, the polymer obtained in Example 33 was used, a 1,4-dioxane solution (1.0 wt %) thereof was prepared, and the solution was formed into a 40 nm-thick film by the spin coating method, followed by drying at 100° C. for 30 minutes.

Subsequently, the following compound EM1 was deposited to form a 40 nm-thick emitting layer. Simultaneously, as the material for the emitting layer, the following amine compound D1 having the following styryl group was deposited such that the weight ratio of EM1 and D1 became 40:2.

On this film, the following Alq was formed into a 10 nm-thick film. This layer functions as an electron-injecting layer. Subsequently, Li as a reducing dopant (Li source: manufactured by SAES Getters Co., Ltd.) and Alq were co-deposited, thereby to form an Alq:Li film (film thickness:

10 nm). Metal aluminum was deposited on this Alq:Li film to form a metal cathode, sealed with glass in nitrogen, whereby an organic EL device was fabricated.

Electric current was passed through the device to evaluate the performance thereof. The organic EL device emitted blue light, had a luminous efficiency of 6.8 cd/A and a luminous half life LT50 at room temperature of 3200 hr@1000 cd/m$^2$.

This device was driven in an oven of 60° C. The luminous half life LT50 was 3200 hr@1000 cd/m$^2$.

Therefore, the ratio of the luminous half life at 60° C. to the luminous half life at room temperature was 0.44.

As is apparent from the above, the device of this example was improved in luminous efficiency and life, and the life thereof was lowered only slightly even when it was driven at high temperatures. The results of device evaluation are shown in Table 2.

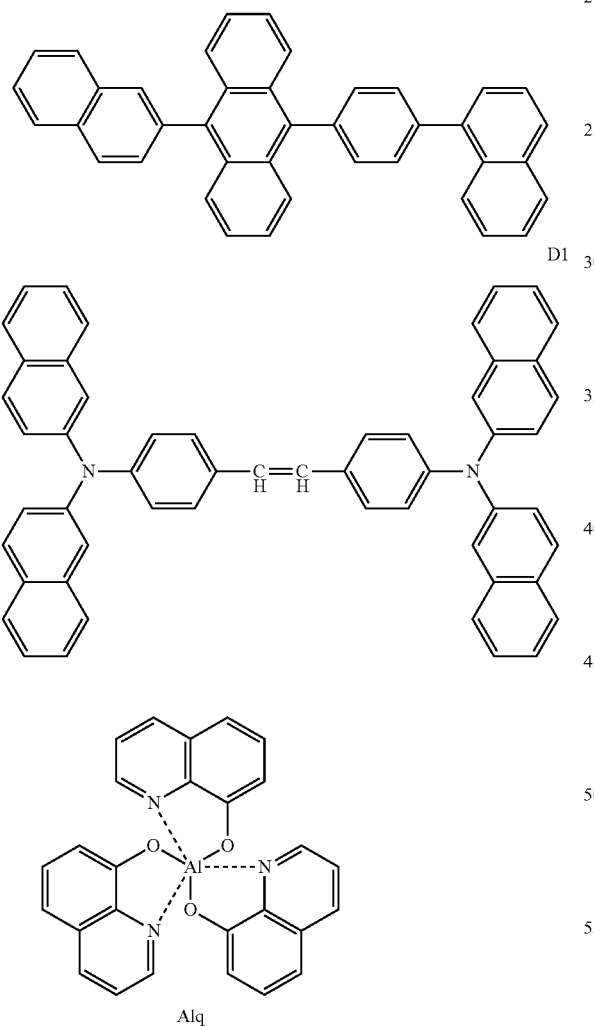

Examples 62 to 88

Organic EL devices were fabricated in the same manner as in Example 61, except that the polymers obtained in Examples 34 to 60 were respectively used as the hole-transporting polymer. Electric current was passed through the device to evaluate the performance thereof. The results are shown in Table 2.

As is apparent from Table 2, the devices of these Examples were improved in luminous efficiency and life, and the life thereof was lowered only slightly even when it was driven at high temperatures.

Example 89

Device Fabrication and Evaluation

An organic EL device was fabricated in the same manner as in Example 61, except that the following arylamine compound D2 was used instead of the amine compound D1 having a styryl group as the material for the emitting layer. Me is a methyl group. The organic EL device was evaluated in the same manner as in Example 61. The results are shown in Table 2.

As is apparent from Table 2, the device of this Example was improved in luminous efficiency and life, and the life thereof was lowered only slightly even when it was driven at high temperatures.

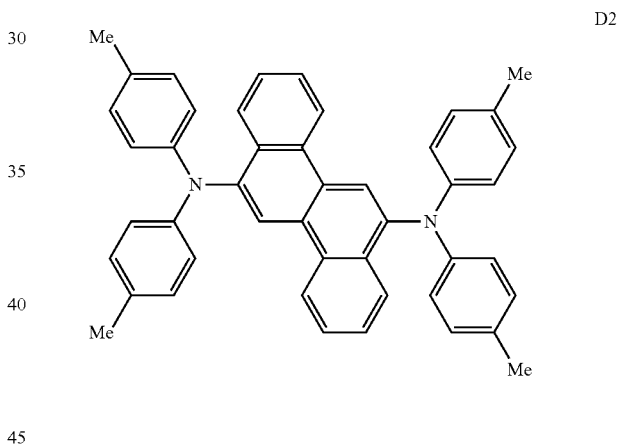

Comparative Example 1

An organic EL device was fabricated and evaluated in the same manner as in Example 61, except that the polymer having the following structural unit which had been synthesized based on the production method given in JP-A-H01-105954 was used as the hole-transporting polymer.

Electric current was passed through the device to evaluate the performance thereof. The organic EL device emitted blue light, had a luminous efficiency of 2.3 cd/A and a luminous half life LT50 at room temperature of 500 hr@1000 cd/m$^2$.

This device was driven in an oven of 60° C. The luminous half life LT50 was 100 hr@1000 cd/m$^2$. Therefore, the ratio of the luminous half life at 60° C. to the luminous half life at room temperature was 0.20.

The device of this Comparative Example was inferior to those of Examples in luminous efficiency and life. In addition, this device suffered a significant lowering in life when it was driven at high temperatures. (see Table 2).

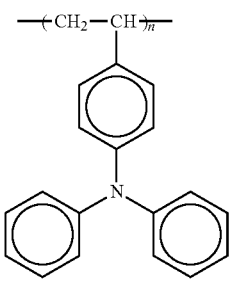

Comparative Example 2

An organic EL device was fabricated and evaluated in the same manner as in Example 61, except that the polymer having the following structural unit which had been synthesized based on the production example given in JP-A-H08-054833 was used as the hole-transporting polymer.

Electric current was passed through the device to evaluate the performance thereof. The organic EL device emitted blue light, had a luminous efficiency of 3.0 cd/A and a luminous half life LT50 at room temperature of 700 hr@1000 cd/m$^2$.

This device was driven in an oven of 60° C. The luminous half life LT50 was 150 hr@1000 cd/m$^2$.

Therefore, the ratio of the luminous half life at 60° C. to the luminous half life at room temperature was 0.21.

The device of this Comparative Example was inferior to those of Examples in luminous efficiency and life. In addition, this device suffered significant lowering in life when it was driven at high temperatures. (see Table 2).

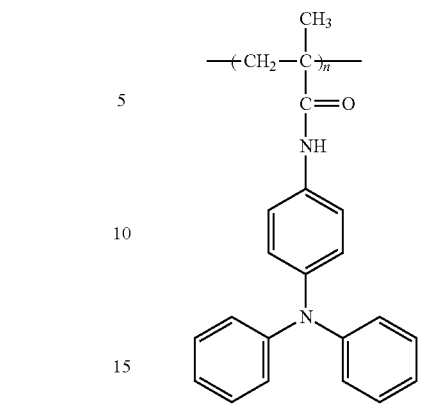

Comparative Example 3

An organic EL device was fabricated and evaluated in the same manner as in Comparative Example 1, except that the dopant was changed to D2 as the material for the emitting layer.

Electric current was passed through the device to evaluate the performance thereof. The organic EL device emitted blue light, had a luminous efficiency of 2.5 cd/A and a luminous half life LT50 at room temperature of 600 hr@1000 cd/m$^2$.

This device was driven in an oven of 60° C. The luminous half life at room temperature LT50 was 150 hr@1000 cd/m$^2$.

Therefore, the ratio of the luminous half life at 60° C. to the luminous half life at room temperature was 0.25.

The device of this Comparative Example was inferior to those of Examples in luminous efficiency and life. In addition, this device suffered significant lowering in life when it was driven at high temperatures. (see Table 2).

TABLE 2

| Example | Hole-translating polymer | Emitting layer host | Emitting layer dopant | Emission color | Luminous efficiency (cd/A) | Luminous half life at room temperature (hr@1000 cd/m$^2$) | Luminance halfe life at 60° C. (hr@1000 cd/m$^2$) | 60° C./Room temperature Lifetime ratio |
|---|---|---|---|---|---|---|---|---|
| Example 61 | Example 33 | EM1 | D1 | Blue | 6.8 | 3,200 | 1,400 | 0.44 |
| Example 62 | Example 34 | EM1 | D1 | Blue | 6.5 | 2,800 | 1,300 | 0.46 |
| Example 63 | Example 35 | EM1 | D1 | Blue | 6.6 | 2,900 | 1,200 | 0.41 |
| Example 64 | Example 36 | EM1 | D1 | Blue | 6.7 | 3,000 | 1,200 | 0.40 |
| Example 65 | Example 37 | EM1 | D1 | Blue | 6.6 | 2,900 | 1,300 | 0.45 |
| Example 66 | Example 38 | EM1 | D1 | Blue | 7.2 | 3,400 | 1,200 | 0.35 |
| Example 67 | Example 39 | EM1 | D1 | Blue | 7.0 | 3,300 | 1,400 | 0.42 |
| Example 68 | Example 40 | EM1 | D1 | Blue | 7.0 | 3,000 | 1,100 | 0.37 |
| Example 69 | Example 41 | EM1 | D1 | Blue | 7.1 | 3,100 | 1,100 | 0.35 |
| Example 70 | Example 42 | EM1 | D1 | Blue | 7.0 | 2,900 | 1,000 | 0.34 |
| Example 71 | Example 43 | EM1 | D1 | Blue | 7.2 | 3,000 | 1,100 | 0.37 |
| Example 72 | Example 44 | EM1 | D1 | Blue | 7.0 | 3,100 | 1,100 | 0.35 |
| Example 73 | Example 45 | EM1 | D1 | Blue | 7.1 | 3,100 | 1,200 | 0.39 |
| Example 74 | Example 46 | EM1 | D1 | Blue | 7.0 | 3,000 | 1,100 | 0.37 |
| Example 75 | Example 47 | EM1 | D1 | Blue | 6.6 | 2,900 | 1,000 | 0.34 |
| Example 76 | Example 48 | EM1 | D1 | Blue | 6.9 | 2,900 | 1,000 | 0.34 |
| Example 77 | Example 49 | EM1 | D1 | Blue | 7.0 | 3,000 | 1,100 | 0.37 |
| Example 78 | Example 50 | EM1 | D1 | Blue | 7.0 | 3,100 | 1,100 | 0.35 |
| Example 79 | Example 51 | EM1 | D1 | Blue | 7.1 | 3,000 | 1,000 | 0.33 |
| Example 80 | Example 52 | EM1 | D1 | Blue | 7.1 | 3,100 | 1,100 | 0.35 |
| Example 81 | Example 53 | EM1 | D1 | Blue | 6.9 | 2,900 | 1,000 | 0.34 |
| Example 82 | Example 54 | EM1 | D1 | Blue | 7.0 | 3,100 | 1,100 | 0.35 |
| Example 83 | Example 55 | EM1 | D1 | Blue | 7.0 | 3,000 | 1,000 | 0.33 |
| Example 84 | Example 56 | EM1 | D1 | Blue | 6.9 | 3,100 | 1,300 | 0.42 |
| Example 85 | Example 57 | EM1 | D1 | Blue | 7.1 | 3,000 | 1,200 | 0.40 |
| Example 86 | Example 58 | EM1 | D1 | Blue | 7.0 | 3,200 | 1,300 | 0.41 |
| Example 87 | Example 59 | EM1 | D1 | Blue | 7.1 | 3,100 | 1,300 | 0.42 |
| Example 88 | Example 60 | EM1 | D1 | Blue | 6.9 | 2,900 | 1,200 | 0.41 |
| Example 89 | Example 33 | EM1 | D2 | Blue | 7.2 | 3,400 | 1,400 | 0.41 |
| Com. Example 1 | TPA Polymer 1 | EM1 | D1 | Blue | 2.3 | 500 | 100 | 0.20 |
| Com. Example 2 | TPA Polymer 2 | EM1 | D1 | Blue | 3.0 | 700 | 150 | 0.21 |
| Com. Example 3 | TPA Polymer 1 | EM1 | D2 | Blue | 2.5 | 600 | 150 | 0.25 |

Example 90

An isopropenyl monomer (90) was obtained according to the following scheme.

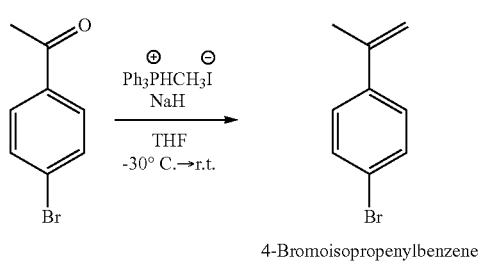

4-Bromoisopropenylbenzene

In a nitrogen stream, to a 500 mL-three neck flask provided with a condenser tube, 60.9 g (150.8 mmol) of methyltriphenylphosphonium iodide and 300 mL of dehydrated THF were added, followed by stirring. The resultant was cooled to −30° C. on a methanol/dry ice bath. After cooling, 3.6 g (150.8 mmol) of sodium hydroxide was slowly added, and the resulting mixture was stirred for 1 hour while cooling. Then, the mixture was heated to room temperature, followed by stirring for 3 hours. The mixture was cooled again to −30° C. on a methanol/dry ice bath. 15 g (75.4 mmol) of 4-bromoacetophenone was added, and stirred for 30 minutes. Then, the mixture was heated to room temperature, followed by stirring for 3 hours. 50 mL of methanol was added, and the reaction was completed. Methylene chloride and water were added, an intended product was extracted, and an organic phase was taken out. MgSO$_4$ was added to this organic phase and dried, and MgSO$_4$ was removed by filtration. The solvent was removed under reduced pressure, and isolation was conducted by means of column chromatography using a mixture of methylene chloride and hexane (1:1) as an eluent, whereby 13.4 g of a transparent liquid was obtained. As a result of NMR, MS or the like, the powder was confirmed to be 4-bromoisopropenylbenzene (yield 90%).

Isopropenylboronic acid was obtained according to the following scheme.

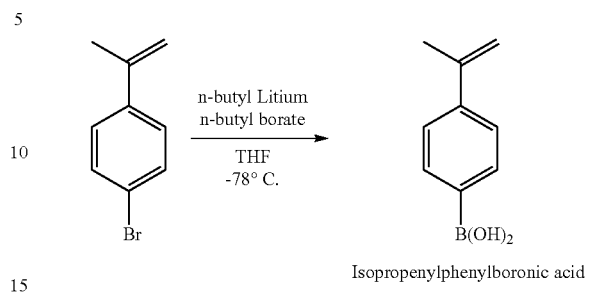

Isopropenylphenylboronic acid

In a nitrogen atmosphere, to a 300 mL-three neck flask provided with a condenser tube, 10 g (50.8 mmol) of 4-bromoisopropenylbenzene, 26.9 g (116.8 mmol) of tributyl borate and 60 mL of dehydrated THF were added, followed by stirring. The resulting mixture was cooled to −78° C. on a methanol/dry ice bath. After cooling, 3.9 g (60.9 mmol) of n-butyllithium was slowly added dropwise. After the dropwise addition, the resulting mixture was stirred for 1 hour while cooling. Then, the mixture was heated to room temperature, followed by stirring for 7 hours. After the completion of the reaction, 10 mL of methanol was added, and 100 mL of a 1N aqueous HCl solution was added dropwise. Methylene chloride and water were added, an intended product was extracted, and an organic phase was taken out. MgSO$_4$ was added to this organic phase and dried, and MgSO$_4$ was removed by filtration. The solvent was removed under reduced pressure, and isolation was conducted by means of column chromatography using a mixture of methylene chloride and ethyl acetate (50:7) as an eluent, whereby 4.91 g of white solids were obtained. As a result of NMR, MS or the like, the solids were confirmed to be isopropenylphenylboronic acid (yield 60%).

An intended product (90) was obtained according to the according to the following scheme.

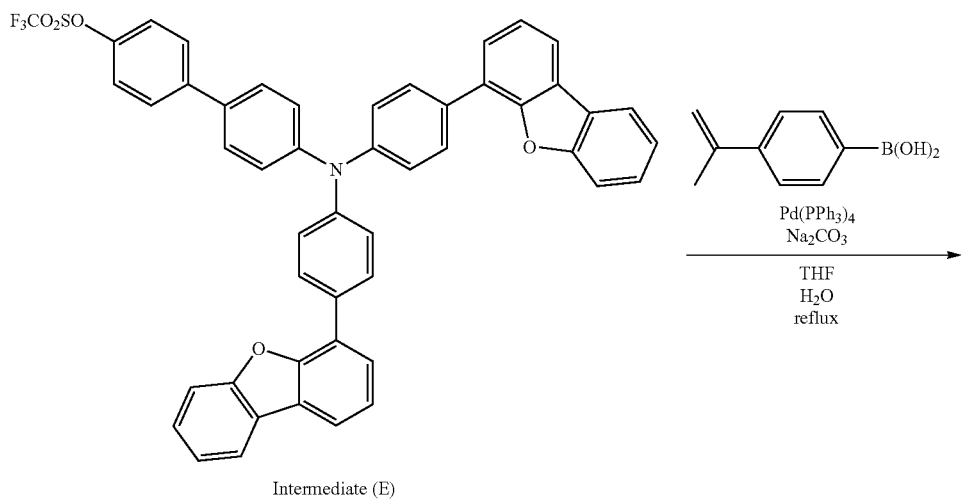

Intermediate (E)

-continued

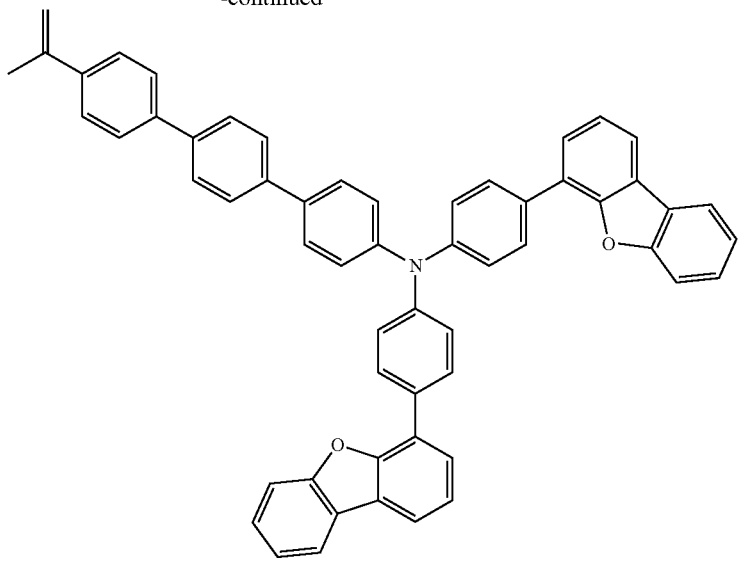

Isopropenyl monomer (90)

In an argon atmosphere, to a 100 mL-three neck flask provided with a condenser tube, 4.2 g (5.0 mmol) of the intermediate (E), 1.21 g (7.5 mmol) of 4-isopropenylphenylboronic acid, 0.12 g (0.1 mol) of tetrakistriphenylphosphine palladium (0), 2.64 g (24.9 mmol) of sodium carbonate, 45 mL of THF and 11 mL of water were added. The resulting mixture was refluxed at 80° C., followed by stirring with heating for 8 hours. After the completion of the reaction, deposited crystals were filtered out, column chromatography was conducted using toluene as a solvent, whereby 3.1 g of white powder was obtained. As a result of NMR, MS or the like, the powder was confirmed to be an intended product (90) (yield 82%).

Polymer: Synthesis of Low-Molecular Polymer

Example 91

A polymer (91) was obtained according to the following scheme.

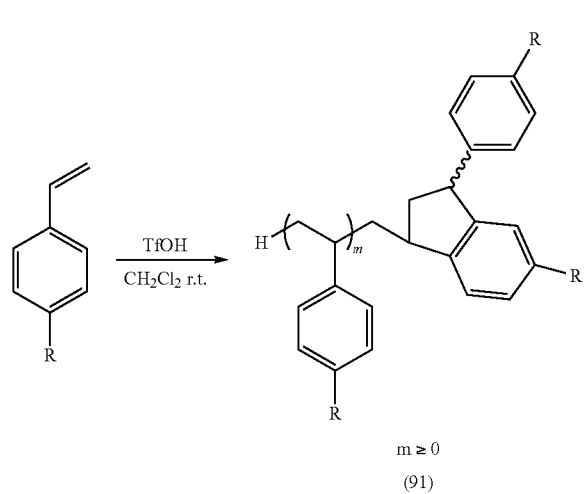

R =

-continued

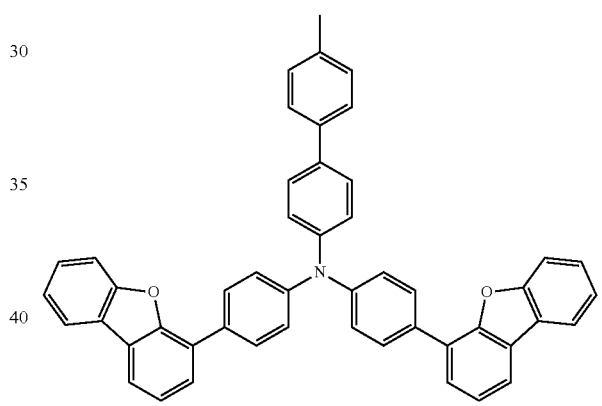

(1) Preparation of a Trifluoromethanesulfonic Acid Solution

A trifluoromethanesulfonic acid solution was prepared in the same manner as in Example 33.

(2) Polymerization (Cationic Polymerization)

A 500 mL-three neck flask provided with a reflux tube was fully replaced by nitrogen. In a nitrogen stream, the flask was charged with 3.27 g (4.33 mmol) of the monomer (8) and dehydrated methylene chloride (1300 mL), and the resultant was stirred under reflux for 1 hour until the monomer compound was completely dissolved. After heating to room temperature, 13 mL (13.0 mmol) of the trifluoromethanesulfonic acid suspension prepared in above (1) was added. The solution was stirred at room temperature for 2 hours, whereby a polymerization reaction was conducted.

(3) Post Treatment after the Reaction

The reaction liquid was poured to a large amount of methanol (2400 mL) with stirring to allow solids (polymer) to be deposited. The solids were separated by filtration. Subsequently, the solids were dissolved in methylene chloride, impurities were removed by silica gel chromatography using methylene chloride as an eluent. Subsequently, the solvent was removed from this solution under reduced pressure. The solids were dissolved in toluene (900 mL) which had been heated, the resulting solution was poured to a large amount of hexane (2400 mL) with stirring, while being filtered by means of filter paper, whereby the solids (polymer) were deposited. Further, hexane was separated by filtration, followed by sufficient drying, thereby to obtain 2.60 g of the polymer (91). The polymer obtained had a number average molecular weight of 2000.

Example 92

Polymer (92) was obtained according to the following scheme.

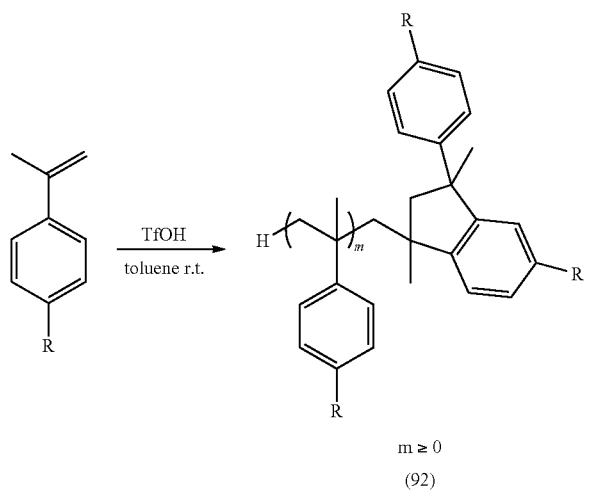

m ≥ 0
(92)

R =

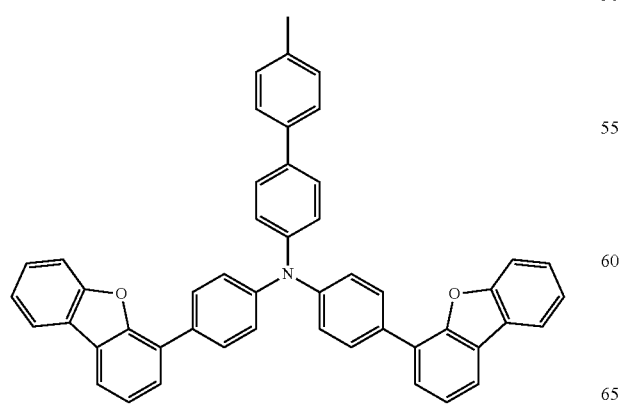

(1) Preparation of a Trifluoromethanesulfonic Acid Solution

In a nitrogen stream, commercially-available trifluoromethanesulfonic acid (10 g, 0.0665 mol, molecular weight: 150.08, specific gravity 1.70) was added to dehydrated toluene to prepare a 0.133 M (total amount of the solution: 500 mL) solution. The trifuloromethanesulfonic acid was mixed with toluene completely homogeneously, and the mixture was used in the following reaction.

(2) Polymerization (Cationic Polymerization)

A 1 L-three neck flask provided with a reflux tube was fully replaced by nitrogen. In a nitrogen stream, 3.00 g (3.90 mmol) of an isopropenyl monomer (90) and dehydrated toluene (800 mL) were placed, and the resulting mixture was completely dissolved at room temperature. To the resultant, 87.9 mL (11.7 mmol) of the trifluoromethanesulfonic acid solution prepared in above (1) was added. This solution was stirred for 6 hours at room temperature, whereby a polymerization reaction was conducted.

(3) Post Treatment after the Reaction

The reaction liquid was washed with water, and an organic phase was extracted. To this organic phase, $MgSO_4$ was added to allow it to be dried. $MgSO_4$ was removed by filtration. The solvent was removed under reduced pressure, and the concentrated liquid was added dropwise to hexane (400 mL), and solids (polymer) were allowed to be deposited by reprecipitation. Further, the polymer was recovered by filtration. Then, in order to remove an unreacted monomer, the polymer was dissolved in 50 mL of toluene. Purification was conducted by column chromatography using a mixture of toluene and hexane (toluene:hexane=1:2) as an eluent. The solvent was removed from the solution which had been recoved under reduced pressure, and fully dried by dying with heating, whereby 2.15 g of the polymer (92) was obtained. The resulting polymer had a number average molecular weight of 1900.

The above-mentioned monomers, the polymers thereof, the polymerization methods thereof are summarized in Table 3.

TABLE 3

| Example | Monomer | Monomer Number | Polymer Example | Polymerization method | Device fabrication, Evaluation Example |
|---|---|---|---|---|---|
| 8 | *[chemical structure]* | (8) | 91 | Cationic | 93 |
| 90 | *[chemical structure]* | (90) | 92 | Cationic | 94 |

Examples 93 and 94

Organic EL devices were fabricated in the same manner as in Example 61, except that the polymer obtained in Examples 91 and 92 were respectively used as the hole-transporting polymer. Electric current was passed through to evaluate the performance thereof. The results obtained are shown in Table 4.

From the results shown in Table 4, it is apparent that the devices obtained in these Examples were superior to those obtained in Comparative Examples and Examples in Table 2 in luminous efficiency and lifetime, and suffered only a slight degree of lowering in life when they were driven at high temperatures.

(Note that, while the number average molecular weight of the polymer of Example 91 was 2000, the number average molecular weight of the polymer of Example 39 was 5700).

TABLE 4

| Example | Hole-transporting polymer | Emitting layer host | Emitting layer dopant | Emission color | Luminous efficiency (cd/A) | Luminous half life at room temperature (hr@1000 cd/m$^2$) | Luminous half life at 60° C. (hr@1000 cd/m$^2$) | 60° C./Room temperature Lifetime ratio |
|---|---|---|---|---|---|---|---|---|
| Example 93 | Example 91 | EM1 | D1 | Blue | 7.5 | 4,500 | 2,200 | 0.49 |
| Example 94 | Example 92 | EM1 | D1 | Blue | 7.7 | 4,300 | 2,100 | 0.49 |

INDUSTRIAL APPLICABILITY

According to the invention, it is possible to provide a novel polymerizable monomer having a polymerizable functional group, as well as a polymer having it as a repeating unit, which is effective as the hole-injecting/transporting material of an organic device, in particular, an organic EL device. The invention can provide an organic EL device which is suited to practical use since it is improved in device properties such as life and luminous efficiency and suffers only a slight degree of deterioration even when subjected to high-temperature driving which is especially practical in applications such as a display and an illuminator.

In addition, since a homogenous hole-injecting/transporting layer can be formed by the coating method, the organic EL device of the invention is effective for a reduction in cost or an increase in screen size in applications of a display or illumination.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated herein by reference in its entirety.

The invention claimed is:

1. A polymerizable monomer represented by the following formula (1) wherein at least one of $Ar^1$ to $Ar^3$ is a group selected from the group consisting of groups represented by the following formulas (4) and (6) and which is substituted by one or more groups comprising a polymerizable functional group:

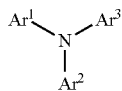
(1)

wherein $Ar^1$ to $Ar^3$ are independently a substituted or unsubstituted aryl group having 6 to 40 ring carbon atoms:

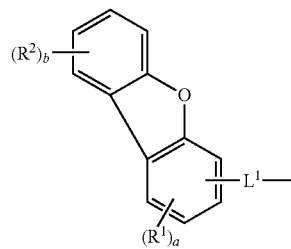
(4)

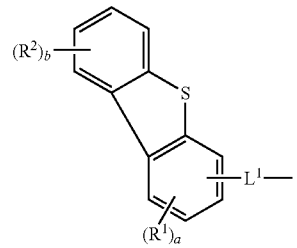
(6)

wherein $L^1$ is a substituted or unsubstituted arylene group having 6 to 50 ring carbon atoms;
the substituents of $L^1$ when it is substituted are one or more groups selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring atoms, a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, triarylsilyl group having 18 to 30 ring carbon atoms, a dialkylarylsilyl group or an alkyldiarylsilyl group having 8 to 30 carbon atoms wherein the aryl part has 6 to 20 ring carbon atoms, an alkylarylamino group having 8 to 30 carbon atoms wherein the aryl part has 6 to 20 ring carbon atoms, a halogen atom, a nitro group, a cyano group and a hydroxyl group;
$R^1$ and $R^2$ are independently a group selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring Carbon atoms, a heterocyclic group having 3 to 30 ring atoms, a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 carbon atoms, an alkylarylamino group having 8 to 30 carbon atoms wherein the aryl part has 6 to 20 ring carbon atoms, a halogen atom, a nitro group, a cyano group and a hydroxyl group;
a is an integer of 0 to 3; and
b is an integer of 0 to 4.

2. A polymerizable monomer represented by the following formula (1) wherein at least one of $Ar^1$ to $Ar^3$ is a group represented by the following formula (7), at least one of the remaining groups of $Ar^1$ to $Ar^3$ is a group represented by the following formula (3) and which is further substituted by one or more groups comprising a polymerizable functional group:

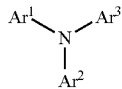
(1)

wherein $Ar^1$ to $Ar^3$ are independently a substituted or unsubstituted aryl group having 6 to 40 ring carbon atoms:

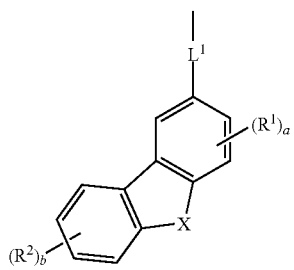
(3)

wherein L is a single bond or a substituted or unsubstituted arylene group having 6 to 50 ring carbon atoms; the substituents of $L^1$ when it is substituted are one or more groups selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring, atoms, a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 ring carbon atoms, an alkylarylamino group having 8 to 30 carbon atoms where the aryl part has 6 to 20 ring carbon atoms, a halogen atom, a nitro group, a cyano group and a hydroxyl group;

X is a substituted or unsubstituted hetero atom; substituents of X when it is substituted are one or more groups selected from the group consisting of a hydrogen atom, an alkyl group having 1 to 20 carbon atoms, a cycloalkyl group having 3 to 10 carbon atoms, an aryl group having 6 to 30 ring carbon atoms, an aralkyl group having 7 to 31 carbon atoms wherein the aryl part has 6 to 30 ring carbon atoms and a heterocyclic group having 3 to 30 ring atoms;

$R^1$ and $R^2$ are independently a group selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring atoms, a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 carbon atoms, an alkylarylamino group having 8 to 30 carbon atoms wherein the aryl part has 6 to 20 ring carbon atoms, a halogen atom, a nitro group, a cyano group and a hydroxyl group;

a is an integer of 0 to 3; and
b is an integer of 0 to 4;

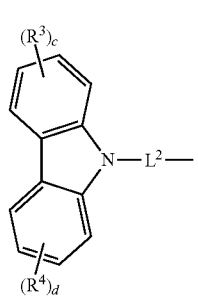
(7)

wherein $R^3$ and $R^4$ are independently a group selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring atoms, a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 ring carbon atoms, an alkylarylamino group having 8 to 30 carbon atoms wherein the aryl part has 6 to 20 ring carbon atoms, a halogen atom, a nitro group, a cyano group and a hydroxyl group;

c and d are independently an integer of 0 to 4;
$L^2$ is a substituted or unsubstituted arylene group having 10 to 50 ring carbon atoms; and
the substituents of $L^2$ when it is substituted are one or more groups selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring atoms, a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 ring carbon atoms, an alkylarylamino group having 8 to 30 carbon atoms wherein the aryl part has 6 to 20 ring carbon atoms, a halogen atom, a nitro group, a cyano group and a hydroxyl group.

3. The polymerizable monomer according to claim 1, wherein, in the formula (1), at least one of the groups of $Ar^1$ to $Ar^3$ is a group represented by the formula (3) and at least one of the remaining groups of $Ar^1$ to $Ar^3$ is a group represented by the following formula (7):

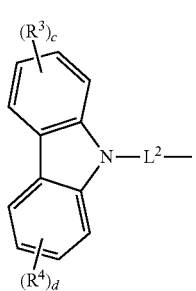

(7)

wherein $R^3$ and $R^4$ are independently a group selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring atoms, a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 ring carbon atoms, an alkylarylamino group having 8 to 30 carbon atoms wherein the aryl part has 6 to 20 ring carbon atoms, a halogen atom, a nitro group, a cyano group and a hydroxyl group;

c and d are independently an integer of 0 to 4;

$L^2$ is a substituted or unsubstituted arylene group having 10 to 50 ring carbon atoms; and the substituents of $L^2$ when it is substituted are one or more groups selected from the group consisting of an alkyl group having 1 to 20 carbon atoms, a cycloalkyl group having 3 to 10 carbon atoms, an aryl group having 6 to 30 ring carbon atoms, alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring atoms, a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 ring carbon atoms, an alkylarylamino group having 8 to 30 carbon atoms wherein the aryl part has 6 to 20 ring carbon atoms, a halogen atom, a nitro group, a cyano group and a hydroxyl group.

4. The polymerizable monomer according to claim 1, wherein $L^1$ is selected from the group consisting of a phenylene group, a naphthylene group, a biphenylene group, a terphenylene group and a fluorenylene group.

5. The polymerizable monomer according to claim 3, wherein $L^2$ is selected from the group consisting of a naphthylene group, a biphenylene group, a terphenylene group and a fluorenylene group.

6. The polymerizable monomer according to claim 1, wherein the number of the at least one group comprising a polymerizable functional group is one.

7. The polymerizable monomer according to claim 1, wherein an aromatic group at the terminal is substituted by the group comprising a polymerizable functional group and the polymerizable functional group and the part other than the terminal aromatic group are bonded to the terminal aromatic group at the para position.

8. The polymerizable monomer according to claim 1, wherein the group comprising a polymerizable functional group is a group selected from the groups of the following formulas (i) to (v):

(i) a group comprising a vinyl group or a vinylidene group shown below:

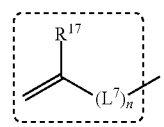

wherein $R^{17}$ is a hydrogen atom, an alkyl group having 1 to 50 carbon atoms or a substituted or unsubstituted aryl group having 6 to 40 ring carbon atoms; $L^7$ is a divalent linking group; and n is an integer of 0 or 1:

(ii) a group comprising a N-maleimide group shown below:

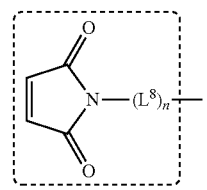

wherein $L^8$ is a divalent linking group and n is an integer of 0 or 1:

(iii) a group comprising a norbornenyl group shown below:

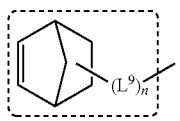

wherein $L^9$ is a divalent linking group and n is an integer of 0 or 1:
(iv) a group comprising an acetylenyl group shown below:

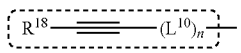

wherein $R^{18}$ is a hydrogen atom, an alkyl group having 1 to 50 carbon atoms or a substituted or unsubstituted aryl group having 6 to 40 ring carbon atoms; $L^{10}$ is a divalent linking group; and n is an integer of 0 or 1: and
(v) a group comprising a cyclopolymerizable or ring-opening polymerizable functional group selected from the group consisting of a group having a substituted or unsubstituted norbornene skeleton other than the group (iii), a group having a substituted or unsubstituted epoxy group or a substituted or unsubstituted oxetane group; a functional group having a lactone structure or a lactum structure; a cyclooctatetraene group or a 1,5-cyclooctadiene group; and 1,ω-diene group, an o-divinylbenzene group and a 1,ω-diyne group.

9. The polymerizable monomer according to claim 8, wherein $L^7$ to $L^{10}$ comprise one linking group or a linking group formed by bonding, in an arbitral order, of two or more linking groups, the linking group being selected from the following divalent linking groups:

-$L^{11}$-, —O—, —C(=O)—, —C(=O)O—, —OC(=O)—, —C(=O)NR$^{19}$—, —NR$^{20}$C(=O)—, —NR$^{21}$—, —S—, —C(=S)— wherein $L^{11}$ is one group or a group formed by bonding, in an arbitral order, of two or more groups, the group being selected from the group consisting of a substituted or unsubstituted arylene group having 6 to 40 ring carbon atoms, a substituted or unsubstituted divalent heterocyclic group having 3 to 40 ring atoms, a substituted or unsubstituted alkylene group having 1 to 50 carbon atoms, a substituted or unsubstituted vinylene group, a substituted or unsubstituted vinylidene group and an ethynylene group; and $R^{19}$ to $R^{21}$ are independently selected from the group consisting of a hydrogen atom, an alkyl group having 1 to 50 carbon atoms and a substituted or unsubstituted aryl group having 6 to 40 ring carbon atoms.

10. A polymer comprising a repeating unit derived from one or two or more selected from the group consisting of the polymerizable monomers according to claim 1.

11. The polymer according to claim 10 which has a number average molecular weight (Mn) or a weight average molecular weight (Mw) of $1.0 \times 10^3$ to $5 \times 10^3$.

12. A material for an organic device comprising the polymer according to claim 10.

13. A hole-injecting/transporting material comprising the polymer according to claim 10.

14. A material for an organic electroluminescence EL device comprising the polymer according to claim 10.

15. An organic electroluminescence device comprising one or a plurality of organic thin film layers comprising an emitting layer between a cathode and an anode and at least one layer of the organic thin film layers comprising the polymer according to claim 10.

16. An organic electroluminescence device comprising one or a plurality of organic thin film layers, comprising an emitting layer between a cathode and an anode and at least one layer of the organic thin film layers comprising the polymer according to claim 10,
wherein the organic thin film layers comprise one or both of a hole-transporting layer and a hole-injecting layer, and one or both of the hole-transporting layer and the hole-injecting layer comprises the polymer according to claim 10.

17. An organic electroluminescence device comprising one or a plurality of organic thin film layers comprising an emitting layer between a cathode and an anode and at least one layer of the organic thin film layers comprising the polymer according to claim 10,
wherein the organic thin film layers comprise one or both of a hole-transporting layer and a hole-injecting layer, and one or both of the hole-transporting layer and the hole-injecting layer comprises the polymer according to claim 10,
wherein one or both of the hole-transporting layer and the hole-injecting layer comprises the polymer according to claim 10 as a main component.

18. The organic electroluminescence device according to claim 15 wherein the emitting layer comprises one or both of a styrylamine compound and on arylamine compound.

19. The organic electroluminescence device according to claim 16 wherein the organic thin film layers comprise one or both of the hole-injecting layer and the hole-transporting layer and one or both of the hole-injecting layer and the hole-transporting layer comprises an acceptor material.

20. The organic electroluminescence device according to claim 15 which can emit blue light.

21. The polymerizable monomer according to claim 2 wherein the group represented by the formula (3) is a group selected from the group consisting of groups represented by the following formulas (4) to (6):

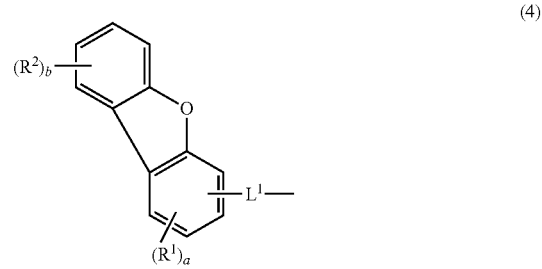

(4)

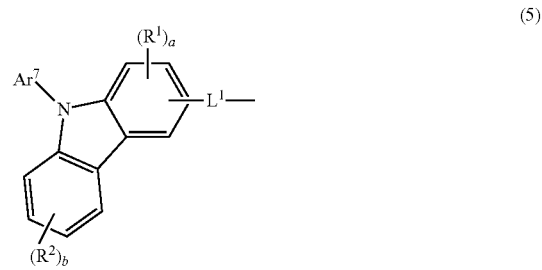

(5)

-continued

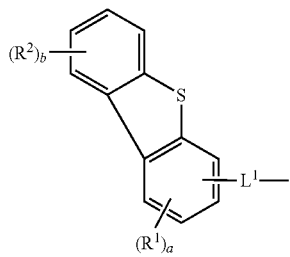
(6)

wherein $L^1$, $R^1$, $R^2$, a and b are as defined in claim 2; and $Ar^7$ is a group selected from the group consisting of a hydrogen atom, an alkyl group having 1 to 20 carbon atoms, a cycloalkyl group having 3 to 10 carbon atoms, an aryl group having 6 to 30 ring carbon atoms, an aralkyl group having 7 to 31 carbon atoms wherein the aryl part has 6 to 30 ring carbon atoms and a heterocyclic group having 3 to 30 ring atoms.

22. A polymerizable monomer represented by the following formula (1) wherein at least one of $Ar^1$ to $Ar^3$ is a group represented by the following formula (3), at least one of the remaining groups of $Ar^1$ to $Ar^3$ is a substituted or unsubstituted biphenylyl group and which is substituted by one or more groups comprising a polymerizable functional group:

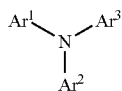
(1)

wherein $Ar^1$ to $Ar^3$ are independently a substituted or unsubstituted aryl group having 6 to 40 ring carbon atoms:

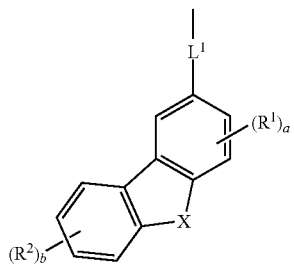
(3)

wherein $L^1$ is a substituted or unsubstituted arylene group having 6 to 50 ring carbon atoms;
the substituents of $L^1$ when it is substituted are one or more groups selected from the group consisting of an alkyl group having 1 to 20 carbon atoms, cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring atoms, a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 ring carbon atoms, an alkylarylamino group having 8 to 30 carbon atoms wherein the aryl part has 6 to 20 ring carbon atoms, a halogen atom, a nitro group, a cyano group and a hydroxyl group;
X is a substituted or unsubstituted hetero atom;
the substituents of X when it is substituted are one or more groups selected from the group consisting of a hydrogen atom, an alkyl group having 1 to 20 carbon atoms, a cycloalkyl group having 3 to 10 carbon atoms, an aryl group having 6 to 30 ring carbon atoms, an aralkyl group having 7 to 31 carbon atoms wherein the aryl part has 6 to 30 ring carbon atoms and a heterocyclic group having 3 to 30 ring atoms;
$R^1$ and $R^2$ are independently a group selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring atoms, a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 ring carbon atoms, an alkylarylamino group having 8 to 30 carbon atoms wherein the aryl part has 6 to 20 ring carbon atoms, a halogen atom, a nitro group, a cyano group and a hydroxyl group;
a is an integer of 0 to 3; and
b is an integer of 0 to 4.

23. The polymerizable monomer according to claim 22, wherein the group represented by the formula (3) is a group represented by the following formula (5):

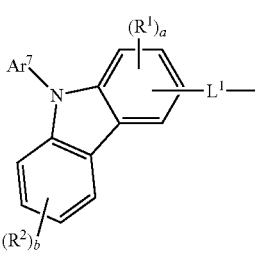
(5)

wherein $L^1$ is a substituted or unsubstituted arylene group having 6 to 50 ring carbon atoms;
the substituents of $L^1$ when it is substituted are one or more groups selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring atoms, a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 ring carbon atoms, an alkylarylamino group having 8 to 30 carbon atoms wherein the aryl part has 6 to 20 ring carbon atoms, a halogen atom, a nitro group, a cyano group and a hydroxyl group;

$R^1$ and $R^2$ are independently a group selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring atoms, a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 carbon atoms, an alkylarylamino group having 8 to 30 carbon atoms wherein the aryl part has 6 to 20 ring carbon atoms, a halogen atom, a nitro group, a cyano group and a hydroxy group;

a is an integer of 0 to 3;
b) is an integer of 0 to 4; and
$Ar^7$ is a group selected from the group consisting of an alkyl group having 1 to 20 carbon atoms, a cycloalkyl group having 3 to 10 carbon atoms, an aryl group having 6 to 30 ring carbon atoms, an aralkyl group having 7 to 31 carbon atoms wherein the aryl part has 6 to 30 ring carbon atoms and a heterocyclic group having 3 to 30 ring atoms, and having a polymerizable functional group.

24. A polymerizable monomer represented by the following formula (1) wherein at least one of $Ar^1$ to $Ar^3$ is a group represented by the following formula (7), at least one of the remaining groups of $Ar^1$ to $Ar^3$ is a substituted or unsubstituted biphenylyl group or a substituted or unsubstituted terphenylyl group and which is further substituted by one or more groups comprising a polymerizable functional group:

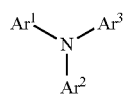

(1)

wherein $Ar^1$ to $Ar^3$ are independently a substituted or unsubstituted aryl group having 6 to 40 ring carbon atoms:

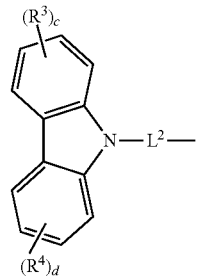

(7)

wherein $R^3$ and $R^4$ are independently a group selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring atoms, a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the part has 6 to 20 ring carbon atoms, an alkylarylamino group having 8 to 30 carbon atoms wherein the aryl part has 6 to 20 ring carbon atoms, a halogen atom, a nitro group, a cyano group and a hydroxyl group;

c and d are independently an integer of 0 to 4;
$L^2$ is a substituted or unsubstituted arylene group having 10 to 50 ring carbon atoms; and
the substituents of $L^2$ when it is substituted are one or more groups selected from the group consisting of an alkyl group having 1 to 20 carbon atoms, a cycloalkyl group having 3 to 10 carbon atoms, an aryl group having 6 to 30 ring carbon atoms, an alkoxy group having 1 to 20 carbon atoms, a cycloalkoxy group having 3 to 10 carbon atoms, an aryloxy group having 6 to 30 ring carbon atoms, an aralkyl group having 7 to 31 carbon atoms wherein the aryl part has 6 to 30 ring carbon atoms, a heterocyclic group having 3 to 30 ring atoms, a mono- or dialkylamino group having an alkyl group having 1 to 20 carbon atoms, a mono- or diarylamino group having an aryl group having 6 to 30 ring carbon atoms, a trialkylsilyl group having 3 to 20 carbon atoms, a triarylsilyl group having 18 to 30 ring carbon atoms, a dialkylarylsilyl group or an alkyldiarylsilyl group having 8 to 30 carbon atoms wherein the aryl part has 6 to 20 ring carbon atoms, an alkylarylamino group having 8 to 30 carbon atoms wherein the aryl part has 6 to 20 ring carbon atoms, a halogen atom, a nitro group, a cyano group and a hydroxyl group.

25. The polymerizable monomer according to claim 24, wherein two of $Ar^1$ to $Ar^3$ are the group represented by formula (7).

26. The polymerizable monomer according to claim 24, wherein at least one of the remaining groups of $Ar^1$ to $Ar^3$ is a substituted or unsubstituted terphenylyl group, and
$L^2$ is a unsubstituted fluorenylene group.

* * * * *